US007871605B2

(12) United States Patent  
Hampson et al.

(10) Patent No.: US 7,871,605 B2  
(45) Date of Patent: Jan. 18, 2011

(54) MIXED CELL POPULATIONS FOR TISSUE REPAIR AND SEPARATION TECHNIQUE FOR CELL PROCESSING

(75) Inventors: Brian Hampson, Canton, MI (US); Kristin Goltry, Milan, MI (US); Doug Smith, Ann Arbor, MI (US); Jonathan A. Rowley, Ann Arbor, MI (US); Naia Venturi, Ypsilanti, MI (US)

(73) Assignee: Aastrom Bioscience, Inc., Ann Arbor, MI (US)

( * ) Notice: Subject to any disclaimer, the term of this patent is extended or adjusted under 35 U.S.C. 154(b) by 708 days.

(21) Appl. No.: 11/983,008

(22) Filed: Nov. 5, 2007

(65) Prior Publication Data

US 2008/0175825 A1    Jul. 24, 2008

Related U.S. Application Data

(60) Provisional application No. 60/856,504, filed on Nov. 3, 2006, provisional application No. 60/932,702, filed on Jun. 1, 2007.

(51) Int. Cl.
*C12N 5/0775* (2010.01)
*C12N 5/074* (2010.01)
*C12N 5/0789* (2010.01)

(52) U.S. Cl. .................... 424/93.7; 435/347
(58) Field of Classification Search ................ None
See application file for complete search history.

(56) References Cited

U.S. PATENT DOCUMENTS

| | | | |
|---|---|---|---|
| 4,839,292 A | 6/1989 | Cremonese | 435/313 |
| 5,437,994 A | 8/1995 | Emerson et al. | 435/240.2 |
| 5,459,069 A | 10/1995 | Palsson et al. | 435/289.1 |
| 5,486,359 A | 1/1996 | Caplan et al. | 424/93.7 |
| 5,605,822 A | 2/1997 | Emerson et al. | 435/172.3 |
| 5,635,386 A | 6/1997 | Palsson et al. | 435/372 |
| 5,646,043 A | 7/1997 | Emerson et al. | 435/373 |
| 5,670,147 A | 9/1997 | Emerson et al. | 424/93.1 |
| 5,670,351 A | 9/1997 | Emerson et al. | 435/172.3 |
| 5,688,687 A | 11/1997 | Palsson et al. | 435/293.2 |
| 5,763,266 A | 6/1998 | Palsson et al. | 435/289.1 |
| 5,811,094 A | 9/1998 | Caplan et al. | 424/93.7 |
| 5,888,807 A | 3/1999 | Palsson et al. | 435/293.2 |
| 5,914,108 A | 6/1999 | Tsukamoto et al. | 424/93.7 |
| 5,985,653 A | 11/1999 | Armstrong et al. | 435/303.1 |
| 5,994,129 A | 11/1999 | Armstrong et al. | 435/325 |
| 6,048,721 A | 4/2000 | Armstrong et al. | 435/286.5 |
| 6,096,532 A | 8/2000 | Armstrong et al. | 435/286.5 |
| 6,228,635 B1 | 5/2001 | Armstrong et al. | 435/286.5 |
| 6,238,908 B1 | 5/2001 | Armstrong et al. | 435/286.5 |
| 6,326,198 B1 | 12/2001 | Emerson et al. | 435/373 |
| 6,328,960 B1 | 12/2001 | McIntosh et al. | 424/93.71 |
| 6,355,239 B1 | 3/2002 | Bruder et al. | 424/93.1 |
| 6,368,636 B1 | 4/2002 | McIntosh et al. | 424/577 |
| 6,387,367 B1 | 5/2002 | Davis-Sproul et al. | 424/93.1 |
| 6,387,369 B1 | 5/2002 | Pittenger et al. | 424/93.7 |
| 6,541,024 B1 | 4/2003 | Kadiyala et al. | 424/426 |
| 6,667,034 B2 | 12/2003 | Palsson et al. | 424/93.7 |
| 6,676,937 B1 | 1/2004 | Isner et al. | 424/93.7 |
| 6,777,231 B1 | 8/2004 | Katz et al. | 435/325 |
| 6,797,269 B2 | 9/2004 | Mosca et al. | 424/184.1 |
| 6,835,566 B2 | 12/2004 | Smith et al. | 435/355 |
| 6,863,900 B2 | 3/2005 | Kadiyala et al. | 424/426 |
| 6,875,430 B2 | 4/2005 | McIntosh et al. | 424/93.7 |
| 6,878,371 B2 | 4/2005 | Ueno et al. | 424/93.1 |
| 7,015,037 B1 | 3/2006 | Furcht et al. | 435/372 |
| 7,029,666 B2 | 4/2006 | Bruder et al. | 424/93.1 |
| 7,097,832 B1 | 8/2006 | Kornowski et al. | 424/93.7 |
| 7,101,704 B1 | 9/2006 | Mosca | 435/325 |
| 7,122,178 B1 | 10/2006 | Simmons et al. | 424/93.1 |
| 2003/0022210 A1 | 1/2003 | Bonyhadi et al. | 435/6 |
| 2003/0170238 A1 | 9/2003 | Gruenberg et al. | 424/144.1 |
| 2006/0073124 A1 | 4/2006 | Garcia Castro et al. | 424/93.21 |

FOREIGN PATENT DOCUMENTS

| | | |
|---|---|---|
| WO | WO 2006/053629 A1 | 5/2006 |
| WO | WO 2006/086716 A2 | 8/2006 |
| WO | WO 2006/105219 A2 | 10/2006 |

OTHER PUBLICATIONS

Aggarwal et al., "Human mesenchymal stem cells modulate allogeneic immune cell responses", *Blood*, 105(4):1815-1822 (2005).

(Continued)

*Primary Examiner*—Allison M Ford
(74) *Attorney, Agent, or Firm*—Ivor R. Elrifi; Cynthia A. Kozakiewicz

(57) ABSTRACT

The present invention provides a fluid exchange cell culture technique and tissue repair cells (TRCs) made by these methods, as well as methods using these cells. The method includes a new wash step which increases the tissue repair properties of the TRCs of the invention. This wash step allows for the production of TRC populations with greater tissue repair and anti-inflammatory capabilities. Embodiments of the present invention include a post-culture process for cultured cells that preferably includes the steps of: a wash process for removing unwanted residual culture components, a volume reduction process, and a harvesting process to remove cultured cells. Preferably, all these steps are performed within a aseptically closed cell culture chamber by implementing a separation method that minimizes mechanical disruption of the cells and is simple to automate. The harvested cells may then be concentrated to a final volume for the intended use. In such embodiments, the final composition is a substantially purified and concentrated cell mixture suspended in a physiologic solution suitable for immediate use in humans without further washing, volume reduction, or processing. Embodiments are also applicable to harvesting (and/or washing) particles within a liquid or solution within a chamber.

11 Claims, 32 Drawing Sheets

OTHER PUBLICATIONS

Armstrong et al., "Continuous medium perfusion during ex vivo expansion of human CD8+ T-cells produces high density cultures and enhances proliferation potential and lymphokine release", *Exp. Hematol.*, Abstract #549, 25:886 (1997).

D'Arc et al., "Micro macroporous biphasic ceramics and fibrin sealant as a moldable material for bone reconstruction in chronic otitis media surgery. A 15 years experience", *J. Mater. Sci. Mater. Med.*, 14:229-233 (2003).

Betz, R.R., "Limitations of Autograft and Allograft: New Synthetic Solutions", *Orthopedics*, 25(5/Suppl.):s561-s570 (2002).

Caldwell et al., "Culture Perfusion Schedules Influence the Metabolic Activity and Granulocyte-Macrophage Colony-Stimulating Factor Production Rates of Human Bone Marrow Stromal Cells", *J. Cell. Physiol.*, 147:344-353 (1991).

Carreno et al., "The B7 Family of Ligands and Its Receptors: New Pathways for Costimulation and Inhibition of Immune Responses", *Annu. Rev. Immunol.*, 20:29-53 (2002).

Colnot et al., "Mechanisms of Action of Demineralized Bone Matrix in the Repair of Cortical Bone Defects", *Clin. Orthop. Rel. Res.*, 435:69-78 (2005).

"Content and Review of Chemistry, Manufacturing, and Control (CMC) Information for Human Gene Therapy Investigational New Drug Applications (INDs)", in *Guidance for FDA Reviewers and Sponsors*, pp. 1-41, U.S. Dept of Health & Human Services FDA Center for Biologics Evaluation & Res. (2008).

Deans et al., "Mesenchymal stem cells: Biology and potential clinical uses", *Exp. Hematol.*, 28:875-884 (2000).

Dennis et al., "*In Vivo* Bone Formation of Marrow-Derived Cells Correlates With CD105, CD166, and Thyl Cell Surface Markers", *J. Bone Min. Res.*, Abstract only, 19(Suppl. 1):S266 (2004).

Dennis et al., "Optimizing Bone Marrow-Derived Osteogenic Progenitor Cell Expansion Using the Replicell® Bioreactor System", *J. Bone Min. Res.*, Abstract only, 20:S247 (2005).

Devine, S.M., "Mesenchymal Stem Cells: Will They Have a Role in the Clinic?", *J. Cell. Biochem.*, 38(Suppl.):73-79 (2002).

Diehl et al., "Induction of NFATc2 Expression by Interleukin 6 Promotes T Helper Type 2 Differentiation", *J. Exp. Med.*, 196(1):39-49 (2002).

Diehl et al., "The two faces of IL-6 on Th1/Th2 differentiation", *Mol. Immunol.*, 39:531-536 (2002).

Duffield, J.S., "The inflammatory macrophage: a story of Jekyll and Hyde", *Clin. Sci. (Lond)*, 104:27-38 (2003).

Ermann et al., "Only the $CD62L^+$ subpopulation of $CD4^+CD25^+$ regulatory T cells protects from lethal acute GVHD", *Blood*, 105(5):2220-2226 (2005).

Fändrich et al., "Future Strategies for Tolerance Induction: A Comparative Study Between Hematopoietic Stem Cells and Macrophages", *Hum. Immunol.*, 63:805-812 (2002).

Freeman et al., "Engagement of the PD-1 Immunoinhibitory Receptor by a Novel B7 Family Member Leads to Negative Regulation of Lymphocyte Activation", *J. Exp. Med.*, 192(7):1027-1034 (2000).

Gabrilovich et al., "Vascular Endothelial Growth Factor Inhibits the Development of Dendritic Cells and Dramatically Affects the Differentiation of Multiple Hematopoietic Lineages In Vivo", *Blood*, 92(11):4150-4166 (1998).

Gordon, S., "Alternative Activation of Macrophages", *Nat. Rev. Immunol.*, 3:23-35 (2003).

Graca et al., "Both $CD4^+CD25^+$ and $CD4^+CD25^-$ Regulatory Cells Mediate Dominant Transplantation Tolerance", *J. Immunol.*, 168:5558-5565 (2002).

Gratchev et al., "Alternatively Activated Antigen-Presenting Cells: Molecular Repertoire, Immune Regulation, and Healing", *Skin Pharmacol. Appl. Skin Physiol.*, 14:272-279 (2001).

Gronthos et al., "Surface Protein Characterization of Human Adipose Tissue-Derived Stromal Cells", J. Cell. Physiol., 189:54-63 (2001).

Guardino et al., "Production of myeloid dendritic cells (DC) pulsed with tumor-specific idiotype protein for vaccination of patients with multiple myeloma", *Cytotherapy*, 8(3):277-289 (2006).

Hoffmann et al., "$CD4^+CD25^+$ Regulatory T Cells in Hematopoietic Stem Cell Transplantation", *Curr. Top. Microbiol. Immunol.*, 293:265-285 (2005).

Hofmann et al., "The influence of bone allograft processing on osteoblast attachment and function", *J. Orthop. Res.*, 23:846-854 (2005).

Jaroscak et al., "Augmentation of umbilical cord blood (UCB) transplantation with ex vivo-expanded UCB cells: results of a phase 1 trial using the AastromReplicell System", *Blood*, 101(12):5061-5067 (2003).

Jegoux et al., "In vivo biological performance of composites combining micro-macroporous biphasic calcium phosphate granules and fibrin sealant", *Arch. Orthop. Trauma Surg.*, 125:153-159 (2005).

Jensen et al., "No effect of platelet-rich plasma with frozen or processed bone allograft around noncemented implants", *Int. Orthop.*, 29:67-72 (2005).

Jimenez et al., "Stem and progenitor cell therapy for management of refractory long bone nonunions: a multicenter clinical feasibility study", *American Academy of Orthopaedic Surgeons Annual Meeting*, San Diego, CA (2007) (Abstract Only).

Kalka et al., "Transplantation of *ex vivo* expanded endothelial progenitor cells for therapeutic neovascularization", *Proc. Natl. Acad. Sci. U.S.A.*, 97(7):3422-3427 (2000).

Karpus et al., "MIP-1α and MCP-1 differentially regulate acute and relapsing autoimmune encephalomyelitis as well as Th1/Th2 lymphocyte differentiation", *J. Leukoc. Biol.*, 62:681-687 (1997).

Kasten et al., "Comparison of human bone marrow stromal cells seeded on calcium-deficient hydroxyapatite, β-tricalcium phosphate and demineralized bone matrix", *Biomaterials*, 24:2593-2603 (2003).

Katz et al., "Cell Surface and Transcriptional Characterization of Human Adipose-Derived Adherent Stromal (hADAS) Cells", *Stem Cells*, 23:412-423 (2005).

Kawamoto et al., "Therapeutic potential of ex vivo expanded endothelial progenitor cells for myocardial ischemia", *Circulation*, 103:634-637 (2001).

Kinglsey, et al., "$CD25^+CD4^+$ regulatory T cells prevent graft rejection: CTLA-4- and IL-10-dependent immunoregulation of alloresponses", *J. Immunol.*, 168:1080-1086 (2002).

Kirana et al., "Autologous tissue repair cells in the treatment of ischemia induced chronic tissue ulcers of diabetic foot patients without option of revascularisation: First experiences", *19th World Diabetes Congress IDF*, Cape Town, South Africa (2006) (Abstract Only).

Kneser et al., "Fibrin gel-immobilized primary osteoblasts in calcium phosphate bone cement: in vivo evaluation with regard to application as injectable biological bone substitute", *Cells Tissues Organs*, 179:158-169 (2005).

Koller et al., "Clinical-scale human umbilical cord cell expansion in a novel automated perfusion culture system", *Bone Marrow Transplant.*, 21:653-663 (1998).

Koller et al., "Different measures of human hematopoietic cell culture performance are optimized under vastly different conditions", *Biotechnol. Bioeng.*, 50:505-513 (1996).

Kopp et al., "Contribution of endothelial progenitors and proangiogenic hematopoietic cells to vascularization of tumor and ischemic tissue", *Curr. Opin. Hematol.*, 13:175-181 (2006).

Krampera et al., Role for Interferon-γ in the Immunomodulatory Activity of Human Bone Marrow Mesenchymal Stem Cells, *Stem Cells*, 24:386-398 (2006).

Kruyt et al., "Towards injectable cell-based tissue-engineered bone: the effect of different calcium phosphate microparticles and pre-culturing", *Tissue Eng*, 12(2):309-317 (2006).

Laxmanan et al., "Vascular endothelial growth factor impairs the functional ability of dendritic cells through Id pathways", Biochem. Biophys. Res. Commun., 334:193-198 (2005).

Le Guehennec et al., "A Review of Bioceramics and Fibrin Sealant", *Eur. Cells Mat.*, 8:1-11 (2004).

Le Guehennec et al., "MBCP® biphasic calcium phosphate granules and tissucol® fibrin sealant in rabbit femoral defects: The effect of fibrin on bone ingrowth", *J. Mat. Sci.: Mat. Med.*, 16:29-35 (2005).

Lundell et al., "Cutting Edge Communication, Clinical Scale Expansion of Cryopreserved Small Volume Whole Bone Marrow Aspirates Produces Sufficient Cells for Clinical Use", *J. Hematother.*, 8:115-127 (1999).

Mandalam et al., "*Ex Vivo* Hematopoietic Cell Expansion for Bone Marrow Transplantation," Chapter 13, *Ex Vivo Cell Therapy*, San Diego: Academic Press, pp. 273-291 (1999).

Mankani et al., "In Vivo Bone Formation by Human Bone Marrow Stromal Cells: Effect of Carrier Particle Size and Shape", *Biotechnol. Bioeng.*, 72(1):96-107 (2001).

Mantovani et al., "Decoy receptors: a strategy to regulate inflammatory cytokines and chemokines", *Trends Immunol.*, 22(6):328-336 (2001).

Mauney et al., "In vitro and in vivo evaluation of differentially demineralized cancellous bone scaffolds combined with human marrow stromal cells for tissue engineering", *Biomaterials*, 26:3173-3185 (2005).

Meisel et al., "Human bone marrow stromal cells inhibit allogeneic T-cell responses by indoleamine 2,3-dioxygenase-mediated tryptophan degradation", *Blood*, 103(12):4619-4621 (2004).

Mellor et al., "Tryptophan Catabolism and Regulation of Adaptive Immunity", *J. Immunol.*, 170:5809-5813 (2003).

Mooney et al., "Actively regulating bioengineered tissue and organ formation", *Orthod. Craniofacial Res.*, 8:141-144 (2005).

Moore et al., "Interleukin-10 and the Interleukin-10 Receptor", *Annu. Rev. Immunol.*, 19:683-765 (2001).

Mosser, D.M., "The many faces of macrophage activation", *J. Leukoc. Biol.*, 73:209-212 (2003).

Munn et al., "Inhibition of T Cell Proliferation by Macrophage Tryptophan Catabolism", *J. Exp. Med.*, 189(9):1363-1372 (1999).

Munn et al., "Macrophages and the Regulation of Self-Reactive T cells", *Curr. Pharm. Des.*, 9(3):257-264 (2003).

Munn et al., "Selective Activation-Induced Apoptosis of Peripheral T Cells Imposed by Macrophages, A Potential Mechanism of Antigen-Specific Peripheral Lymphocyte Deletion", *J. Immunol.*, 156:523-532 (1996).

Murohara et al., "Transplanted cord blood-derived endothelial precursor cells augment postnatal neovascularization", *J. Clin. Invest*, 105(11):1527-1536 (2000).

Murphy et al., "$CD4^+CD25^+$ Regulatory T Cells Control Innate Immune Reactivity after Injury", *J. Immunol.*, 174:2957-2963 (2005).

Muschler et al., "Engineering Principles of Clinical Cell-Based Tissue Engineering", *J. Bone Joint Surg.*, 86-A(7):1541-1558 (2004).

Muschler et al., "Selective Retention of Bone Marrow-Derived Cells to Enhance Spinal Fusion", *Clin. Orthop. Rel. Res.*, 432:242-251 (2005).

O'Garra et al., "Regulatory T cells and mechanisms of immune system control", *Nat. Med.*, 10(8):801-805 (2004).

Ohm et al., "VEGF inhibits T-cell development and may contribute to tumor-induced immune suppression", *Blood*, 101(12):4878-4886 (2003).

Okunishi et al., "A Novel Role of Hepatocyte Growth Factor as an Immune Regulator through Suppressing Dendritic Cell Function", *J. Immunol.*, 175:4745-4753 (2005).

Okunishi et al., "Hepatocyte Growth Factor Significantly Suppresses Collagen-Induced Arthritis in Mice", *J. Immunol.*, 179:5504-5513 (2007).

Pecora et al., "A phase II trial evaluating the safety and effectiveness of the AastromReplicell system for augmentation of low-dose blood stem cell transplantation", *Bone Marrow Transplant.*, 28:295-303 (2001).

Pecora et al., "Prompt and durable engraftment in two older adult patients with high risk chronic myelogenous leukemia (CML) using *ex vivo* expanded and unmanipulated unrelated umbilical cord blood", *Bone Marrow Transplant.*, 25:797-799 (2000).

Peterson et al., "Osteoinductivity of commercially available demineralized bone matrix. Preparations in a spine fusion model", *J. Bone Joint Surg.*, 86-A(10):2243-2250 (2004).

Philippidis et al., "Hemoglobin Scavenger Receptor CD163 Mediates Interleukin-10 Release and Heme Oxygenase-1 Synthesis: Antiinflammatory Monocyte-Macrophage Responses In Vitro, in Resolving Skin Blisters In Vivo, and After Cardiopulmonary Bypass Surgery", *Circ. Res.*, 94:119-126 (2004).

Rincon et al., "Interleukin (IL)-6 Directs the Differentiation of IL-4-producing $CD4^+$ T Cells", *J. Exp. Med.*, 185(3):461-469 (1997).

Rochet et al., "Modification of gene expression induced in human osteogenic and osteosarcoma cells by culture on a biphasic calcium phosphate bone substitute", *Bone*, 32:602-610 (2003).

Rutella et al., "Hepatocyte growth factor favors monocyte differentiation into regulatory interleukin $(IL)-10^{++}IL-12^{low/neg}$ accessory cells with dendritic-cell features", *Blood*, 108(1):218-227 (2006).

Sakaguchi et al., "Immunologic tolerance maintained by $CD25^+$ $CD4^+$ regulatory T cells: their common role in controlling autoimmunity, tumor immunity, and transplantation tolerance", *Immunol. Rev.*, 182:18-32 (2001).

Savarino et al., "Evaluation of Bone Healing Enhancement by Lyophilized Bone Grafts Supplemented with Platelet Gel: A Standardized Methodology in Patients with Tibial Osteomy for Genu Varus", *J. Biomed. Mater. Res. B: Appl. Biomater,*, 76(B):364-372 (2006).

Schwartz et al., "Rapid medium perfusion rate significantly increases the productivity and longevity of human bone marrow cultures", *Proc. Natl. Acad. Sci. U.S.A.*, 88(15):6760-6764 (1991).

Smith et al., "Enhanced Yield and Antigen Presenting Function of Human Dendritic Cells Produced Under Perfusion Culture Conditions in a Unique Clinical-Scale Bioreactor System", *Keystone Symposia: Dendritic Cells: Interfaces with Immunobiology and Medicine*, Mar. 12-18, 2001, Taos, New Mexico (2001) (Abstract Only).

Stiff et al., "Autologous transplantation of ex vivo expanded bone marrow cells grown from small aliquots after high-dose chemotherapy for breast cancer", *Blood*, 95(6):2169-2174 (2000).

Szpalski et al., "Applications of Calcium Phosphate-Based Cancellous Bone Void Fillers in Trauma Surgery", *Orthopedics*, 25(5 Suppl.):s601-s609 (2002).

Tang et al., "In vitro-expanded Antigen-specific Regulatory T cells Suppress Autoimmune Diabetes", *J. Exp. Med.*, 199(11):1455-1465 (2004).

Taylor et al., "L-Selectin$^{hi}$ but not the L-selectin$^{lo}$ $CD4^+25^+$ T-regulatory cells are potent inhibitors of GVHD and BM graft rejection", *Blood*, 104(12):3804-3812 (2004).

Xing et al., "IL-6 an Antiinflammatory Cytokine Required for Controlling Local or Systemic Acute Inflammatory Responses", *J. Clin. Invest.*, 101(2):311-320 (1998).

Zuk et al., "Human Adipose Tissue Is a Source of Multipotent Stem Cells", *Mol. Biol. Cell*, 13:4279-4295 (2002).

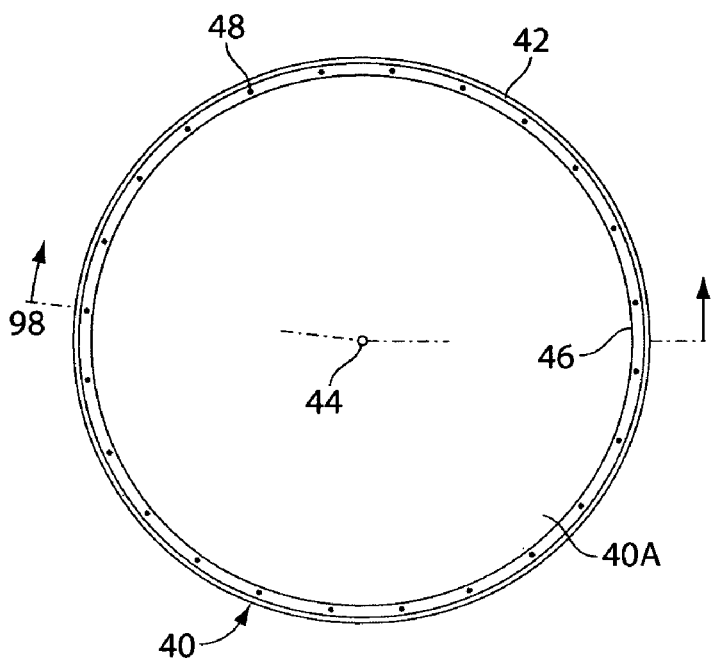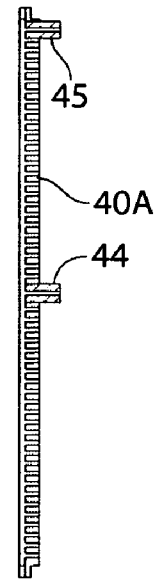
Fig. 9A　　　　Fig. 9B
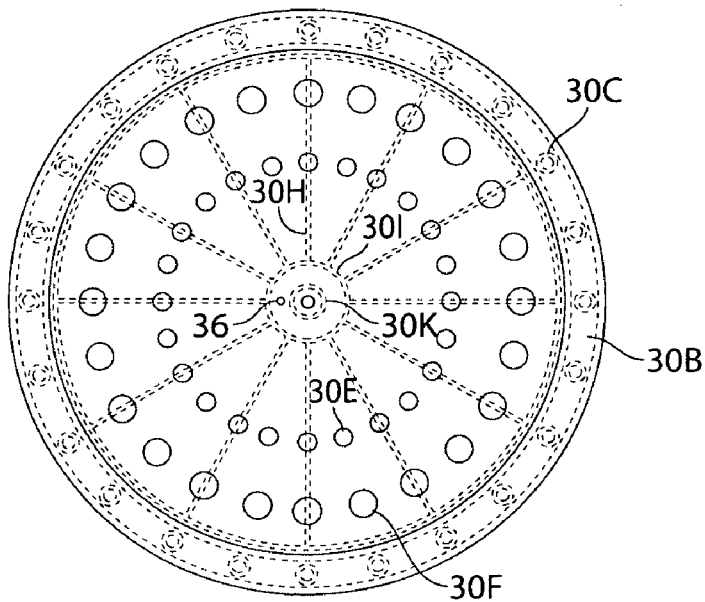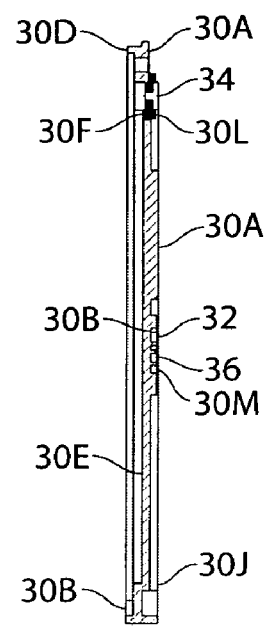
Fig. 10A　　　　Fig. 10B

PRE-TRC TREATMENT     48 WEEKS POST-TRC TREATMENT

US 7,871,605 B2

MIXED CELL POPULATIONS FOR TISSUE REPAIR AND SEPARATION TECHNIQUE FOR CELL PROCESSING

RELATED APPLICATIONS

This application claims the benefit of U.S. Ser. No. 60/856,504 filed Nov. 3, 2006 and to U.S. Ser. No. 60/932,702 filed, Jun. 1, 2007 the contents of which are incorporated by reference in their entireties.

FIELD OF THE INVENTION

The present invention relates to compositions of mixed cell populations, their subsequent use in vivo for tissue repair and processes, devices, and systems for the preparation of the mixed cell populations. The processes of the invention are also applicable at separating any type of cell (adherent, non-adherent or a mixture thereof) or small particles (e.g., cell sized) from a containing liquid or solution.

BACKGROUND OF THE INVENTION

Regenerative medicine harnesses, in a clinically targeted manner, the ability of regenerative cells, e.g., stem cells and/or progenitor cells (i.e., the unspecialized master cells of the body), to renew themselves indefinitely and develop into mature specialized cells. Stem cells are found in embryos during early stages of development, in fetal tissue and in some adult organs and tissue. Embryonic stem cells (hereinafter referred to as "ESCs") are known to become many if not all of the cell and tissue types of the body. ESCs not only contain all the genetic information of the individual but also contain the nascent capacity to become any of the 200+ cells and tissues of the body. Thus, these cells have tremendous potential for regenerative medicine. For example, ESCs can be grown into specific tissues such as heart, lung or kidney which could then be used to repair damaged and diseased organs. However, ESC derived tissues have clinical limitations. Since ESCs are necessarily derived from another individual, i.e., an embryo, there is a risk that the recipient's immune system will reject the new biological material. Although immunosuppressive drugs to prevent such rejection are available, such drugs are also known to block desirable immune responses such as those against bacterial infections and viruses.

Moreover, the ethical debate over the source of ESCs, i.e., embryos, is well-chronicled and presents an additional and, perhaps, insurmountable obstacle for the foreseeable future.

Adult stem cells (hereinafter interchangeably referred to as "ASCs") represent an alternative to the use of ESCs. ASCs reside quietly in many non-embryonic tissues, presumably waiting to respond to trauma or other destructive disease processes so that they can heal the injured tissue. Notably, emerging scientific evidence indicates that each individual carries a pool of ASCs that may share with ESCs the ability to become many if not all types of cells and tissues. Thus, ASCs, like ESCs, have tremendous potential for clinical applications of regenerative medicine.

ASC populations have been shown to be present in one or more of bone marrow, skin, muscle, liver and brain. However, the frequency of ASCs in these tissues is low. For example, mesenchymal stem cell frequency in bone marrow is estimated at between 1 in 100,000 and 1 in 1,000,000 nucleated cells Thus, any proposed clinical application of ASCs from such tissues requires increasing cell number, purity, and maturity by processes of cell purification and cell culture.

Although cell culture steps may provide increased cell number, purity, and maturity, they do so at a cost. This cost can include one or more of the following technical difficulties: loss of cell function due to cell aging, loss of potentially useful cell populations, delays in potential application of cells to patients, increased monetary cost, increased risk of contamination of cells with environmental microorganisms during culture, and the need for further post-culture processing to deplete culture materials contained with the harvested cells.

More specifically, all final cell products must conform with rigid requirements imposed by the Federal Drug Administration (FDA). The FDA requires that all final cell products must minimize "extraneous" proteins known to be capable of producing allergenic effects in human subjects as well as minimize contamination risks. Moreover, the FDA expects a minimum cell viability of 70%, and any process should consistently exceed this minimum requirement.

While there are existing methods and apparatus for separating cells from unwanted dissolved culture components and a variety of apparatus currently in clinical use, such methods and apparatus suffers from a significant problem—cellular damage caused by mechanical forces applied during the separation process, exhibited, for instance, by a reduction in viability and biological function of the cells and an increase in free cellular DNA and debris. Furthermore, significant loss of cells can occur due to the inability to both transfer all the cells into the separation apparatus as well as extract all the cells from the apparatus. In addition, for mixed cell populations, these methods and apparatus can cause a shift in cell profile due to the preferential loss of larger, more fragile subpopulations.

Thus, there is a need in the field of cell therapy, such as tissue repair, tissue regeneration, and tissue engineering, for cell compositions that are ready for direct patient administration with substantially high viability and functionality, and with substantial depletion of materials that were required for culture and harvest of the cells. Furthermore, there are needs for reliable processes and devices to enable production of these compositions that are suitable for clinical implementation and large-scale commercialization of these compositions as cell therapy products.

SUMMARY OF THE INVENTION

The invention provides compositions and methods for tissue repair. The composition are useful for treating a variety of diseases and disorders such as ischemic conditions (e.g., limb ischemia, congestive heart failure, cardiac ischemia, kidney ischemia and ESRD, stroke, and ischemia of the eye), conditions requiring organ or tissue regeneration (e.g., regeneration of liver, pancreas, lung, salivary gland, blood vessel, bone, skin, cartilage, tendon, ligament, brain, hair, kidney, muscle, cardiac muscle, nerve, and limb), inflammatory diseases (e.g., heart disease, diabetes, spinal cord injury, rheumatoid arthritis, osteo-arthritis, inflammation due to hip replacement or revision, Crohn's disease, and graft versus host disease) and auto-immune diseases (e.g., type 1 diabetes, psoriasis, systemic lupus, and multiple sclerosis).

In one aspect the invention provides an isolated cell composition for tissue repair containing a mixed population of cells. The cells are in a pharmaceutical-grade electrolyte solution suitable for human administration. The cells are derived from mononuclear cells. For example, the cells are derived from bone marrow, peripheral blood, umbilical cord blood or fetal liver. The cells are of hematopoietic, mesenchymal and endothelial lineage. The viability of cells is at least 80%, 85%, 90%, 95%, 96%, 97%, 98%, 99% or greater. The total number of viable cells in the composition is 35 million to 300 million and in volume less than 25 ml, 20 ml, 15 ml, 10 ml, 7.5 ml, 5 ml or less. At least 5% of the viable cells in the composition are $CD90^+$. For example, 10%, 20%, 30%, 40%, 50%, 60%, 70%, 75% or more are $CD90^+$. In some aspects at least 5%, 10%, 15%, 20%, 50% or more of the $CD90^+$ co-express CD15. Preferably, the cells are about 5-75% viable $CD90^+$ with the remaining cells in the composition being $CD45^+$. The $CD45^+$ cells are $CD14^+$, $CD34^+$ or $VEGFR1^+$.

The cells produce at least one, two, three four, five or more anti-inflammatory cytokines or angiogenic factors. Anti-inflammatory cytokines include for example interleukin-1 receptor antagonist, interleukin-6, TGF-β, interleukin-8, interleukin 10, or monocyte chemoattractant protein-1. Angiogenic factors include for example, vascular endothelial growth factor, angiopoeitin 1, angiopoeitin 2 or hepatocyte growth factor. Additionally the cells produce less than 50 pg/mL, 40 pg/mL, 30 pg/mL, 20 pg/mL, 10 pg/mL, 5 pg/mL, 2 pg/mL or 1 pg/mL per 24 hour period per $10^5$ cells of one or more pro-inflammatory cytokines such as interleukin-1 alpha, interleukin-1 beta, interferon gamma or interleukin-12. The cells also express indoleamine 2,3, dioxygenase, PD-L1 or both.

The composition is substantially free of components used during the production of the cell composition, e.g., cell culture components such as bovine serum albumin, horse serum, fetal bovine serum, enzymatically active harvest reagent (e.g., trypsin) and substantially free of mycoplasm, endotoxin, and microbial contamination. Preferably, the composition contain 10, 5, 4, 3, 2, 1, 0.1, 0.05 or less µg/ml bovine serum albumin and 5, 4, 3, 2, 1, 0.1, 0.05 µg/ml enzymatically active harvest reagent.

Optionally, the composition further contains a bio-compatible matrix such as for example, demineralized bone particles, mineralized bone particles, synthetic ceramic of the calcium phosphate family (e.g., alpha tri-calcium phosphates, beta tri-calcium phosphates and hydroxyapatites), collagens, polysaccharide-based materials (e.g., hyaluronan and alginates), synthetic biodegradable polymeric materials (e.g., poly-lactides, poly-glycolides, poly-fumarates and poly-ethylene glycol), and mixtures, combinations or blends thereof.

In another aspect the invention provides methods of modulating an immune response, an inflammatory response or angiogenesis in a patient by administering a cultured mixed cell composition to the patient wherein the cultured cell composition produces at least one cytokine such as interleukin-1 receptor antagonist, interleukin-6, interleukin-8, interleukin-10, vascular endothelial growth factor, monocyte chemoattractant protein-1 angiopoeitin 1, angiopoeitin 2 and hepatocyte growth factor. Optionally, the cell composition produces two, three, four, five or more cytokines. Preferably, the composition produces less than 10 ng/mL of interleukin-1 alpha, interferon gamma or interleukin-12. For example, the cell composition contains 0.1% -10% $CD4^+CD24^+$ T-cells, 1-50% $CD45^+CD14^+$ monocytes: and 5%-75% $CD45-CD90^+$ bone marrow stromal cells. Preferably, the cell composition is the cell compositions described above In a further aspect the invention provides a method for processing cultured cells. The method produces a mixed cell population wherein more that 5% of the cell population is $CD90^+$. The method includes: providing a biochamber for culturing cells, providing a culture media for culturing cells within biochamber, inoculating the biochamber with cells. The cells are cultured and upon a predetermined time period of culture, displacing the culture media from the biochamber with a biocompatible first rinse solution substantially replacing the first rinse solution with a cell harvest enzyme solution and incubating the contents of the biochamber for a predetermined period of time such that during incubation, the enzyme at least dissociates the cells from each other and/or from the biochamber surface. The enzyme solution is replaced with a second rinse solution to displace the enzyme solution. The chamber is substantially filled with the second rinse solution. Preferably, the second rinse solution is a solution capable of being injectable into a human. Optionally, the method further comprises on or more addition steps including displacing a portion of the second rinse solution with a gas to obtain a predetermined reduced liquid volume in the chamber; agitating the chamber to bring settled cells into suspension and draining the solution with the suspended cells into a cell collection container. After draining the solution into a cell collection container, additional amounts of the second solution are added to the biochamber, and the biochamber is agitated to rinse out residual cells.

Also included in the invention are the cultured cells and composition containing the cultured cells produced by the methods of the invention.

In another aspect the invention provides a method for harvesting cultured cells. The method includes the steps of displacing culture media from a biochamber with a biocompatible first rinse solution; substantially replacing the first rinse solution with a cell harvest enzyme solution and incubating the contents of the biochamber for a predetermined period of time with the enzyme solution. During incubation, the enzyme at least dissociates the cells from each other and/or from culture surface of the biochamber. The enzyme solution is displaced with a second rinse solution. The chamber is substantially filled with the second rinse solution.

Optionally, the method further includes on or more of the following steps: displacing a portion of the second rinse solution with a gas to obtain a predetermined reduced liquid volume in the chamber; agitating the chamber to bring settled cells into suspension; draining the solution with suspended cells into a cell collection container. After draining the solution into the cell collection container, additional amounts of the second solution are added to the biochamber, and the biochamber is agitated to rinse out the residual cells.

The cells are derived from mononuclear, for example the mononuclear cells are bone marrow, peripheral blood, umbilical cord blood or fetal liver.

In yet a further aspect the invention provides methods for separating micro-particles from a containing liquid or solution provided in a chamber having a predetermined volume and geometry by introducing a second liquid/solution within the chamber to displace the first containing liquid, wherein the geometry of the chamber enables the liquids to flow through the chamber according to a plug-flow and the second liquid substantially displaces the volume of the chamber at least once. Optionally a gas is introduced at a rate to establish a plug-flow, wherein the gas displaces a liquid/solution contained in the chamber to reduce liquid/ solution volume and thereby concentrate the particles within the liquid/solution in the chamber. The method also includes agitating the chamber to bring settled particles into the liquid/solution contained in the chamber and draining the solution into a collection container.

The flow rate for the introduction of solutions and/or gases added to the biochamber for any of the described methods is between about 0.03 to about 1.0 volume exchanges/min. Preferably, the flow rate for the introduction of solutions and/or gases added to the biochamber is between about 0.50 to about 0.75 volume exchanges/min. Optionally, the liquids/solutions or gases are introduced into the biochamber according to a radial plug flow.

The second liquid or subsequent liquid/solution is capable of being injectable into a human.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein:

FIGS. 9A and 9B are top and sectional views of a biochamber cell bed disc according to an embodiment of the invention.

FIGS. 10A and 10B are top and sectional views of a biochamber base according to embodiment of the invention.

DETAILED DESCRIPTION OF THE INVENTION

Figure 1:
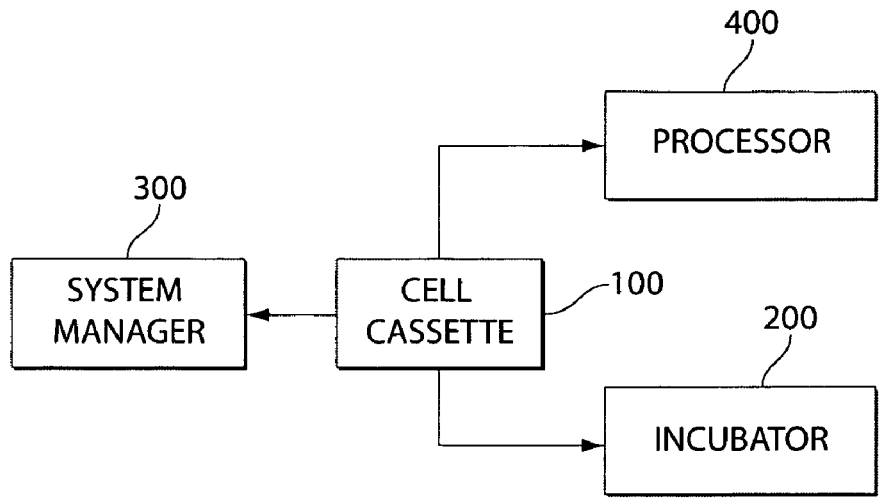
FIG. 1 is a diagram illustrating the major components of the cell production system according to the invention.
Figure 2:
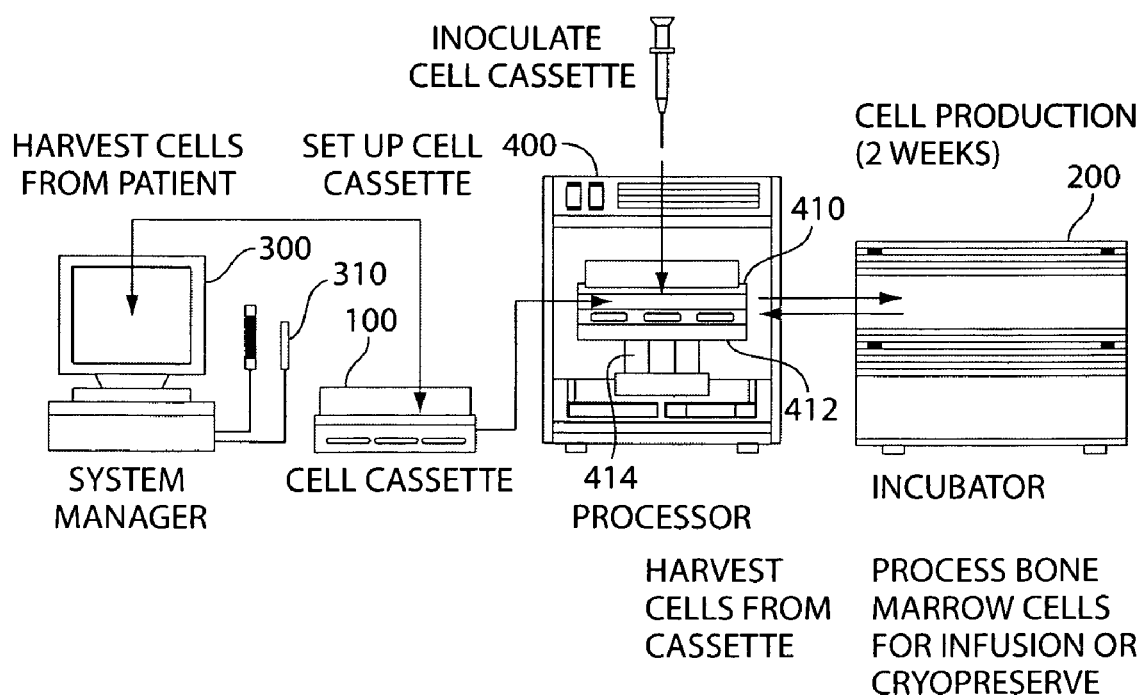
FIG. 2 is a schematic illustration of one embodiment of the overall system of FIG. 1.
Figure 3:
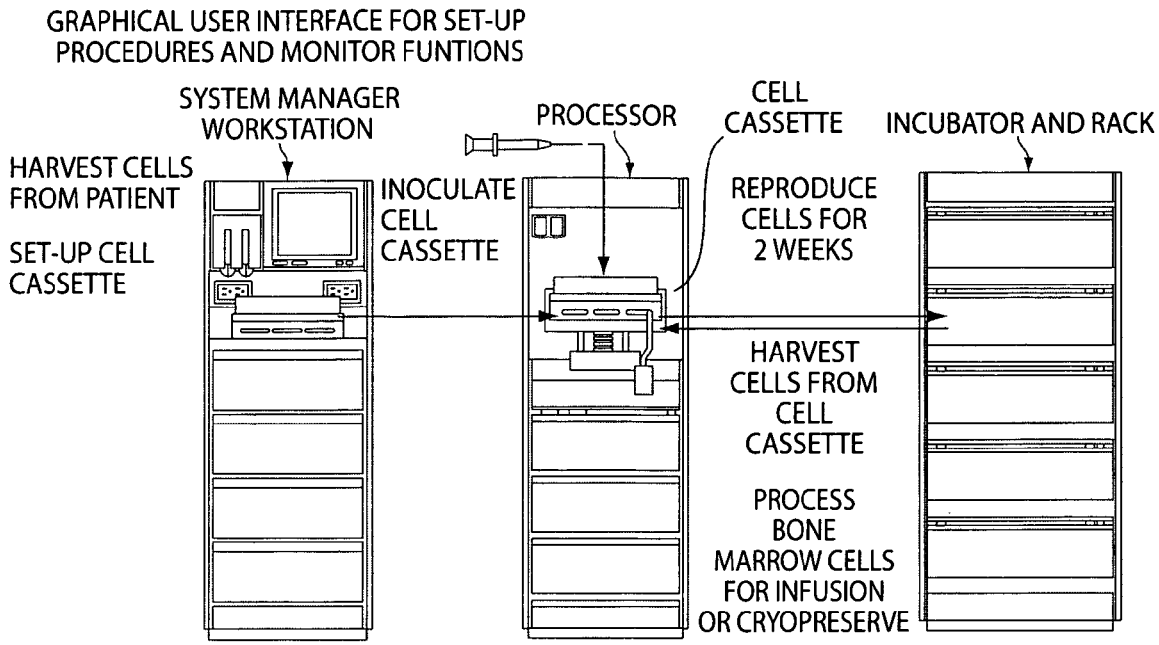
FIG. 3 is a schematic diagram illustrating another embodiment of the overall system of FIG. 1.
Figure 4A:
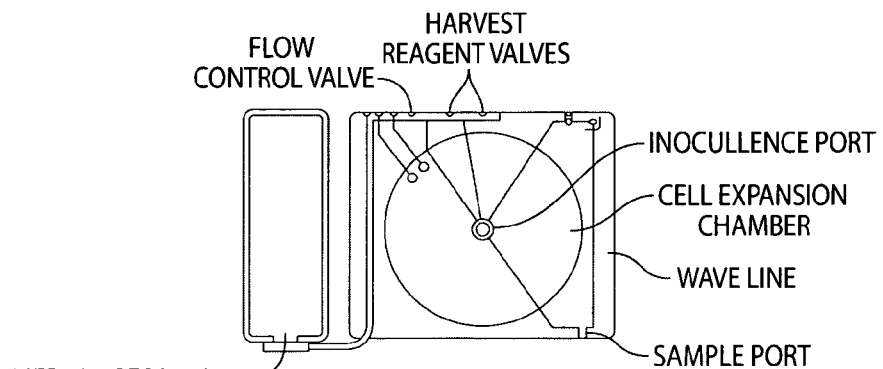
FIGS. 4A and 4B are schematic top and side views of an embodiment of a cell cassette according to the invention.
Figure 4B:
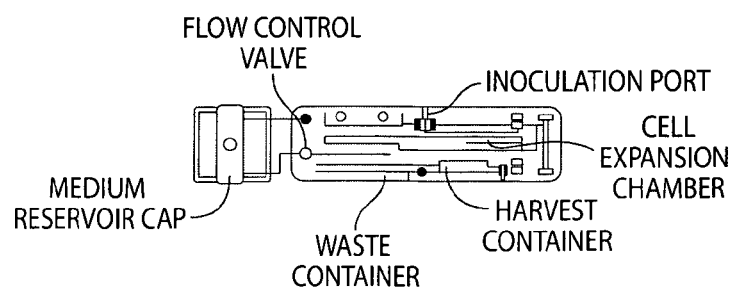

The present invention is based on the discovery of compositions and methods of producing cells for cell therapy. The compositions are a mixed population of cells that are enhanced in stem and progenitor cells that are uniquely suited to human administration for tissue repair, tissue regeneration, and tissue engineering. These cells are referred to herein as "Tissue Repair Cells" or "TRCs"

Accordingly, in one aspect the invention provides a composition containing a mixed population of cells of hematopoietic, mesenchymal and endothelial lineage. The composition is suitable for administration to a human for therapeutic use. TRCs are produced from an in vitro culture process. Once the culture process is completed, culture components (e.g. culture medium, enzyme used for detachment and harvest of the cells) must be separated from the cells before they can be safely administered to a subject in need of tissue regeneration. This separation is conventionally performed in a post-culture cell washing step. However, a significant problem associated with this step is cellular damage caused by mechanical forces applied during these processes, exhibited, for instance, by a reduction in viability and biological function of the cells and an increase in free cellular DNA and debris. This loss of viability and function has not only immediate impact on the cell product, but also greatly impacts the shelf-life and cryopreservation potential of the cells. Additionally, significant loss of cells can occur due to the inability to both transfer all the cells into the washing apparatus as well as extract all the cells from the apparatus.

Accordingly, in another aspect the invention provides a cell washing procedure. The cell washing techniques of the instant invention, as described in the Methods of Production of TRCs below, surprisingly greatly enhanced cell viability and yield compared to current post-culture wash procedures while providing cell compositions with residual levels of culture components that are sufficiently low for safe administration of the cells to a patient.

Tissue Repair Cells (TRCs)

Tissue Repair Cells (TRCs) provide a cellular and molecular composition with high functionality for repair of injured tissues. Additionally, the TRCs have been shown to have anti-inflammatory effects. TRCs contain a mixture of cells of hematopoietic, mesenchymal and endothelial cell lineage produced from mononuclear cells. The mononuclear cells are isolated from adult, juvenile, fetal or embryonic tissues. For example, the mononuclear cells are derived from bone marrow, peripheral blood, umbilical cord blood or fetal liver tissue. TRCs are produced from mononuclear cells for example by an in vitro culture process which results in a unique cell composition having both phenotypic and functional differences compared to the mononuclear cell population that was used as the starting material. Additionally, the TRCs of the instant invention have both high viability and low residual levels of components used during their production.

The viability of the TRC's is at least 50%, 60%, 70%, 75%, 80%, 85%, 90%, 95% or more. Viability is measured by methods known in the art such as trypan blue exclusion. This enhanced viability makes the TRC population more effective in tissue repair, as well as enhances the shelf-life and cryopreservation potential of the final cell product.

By components used during production is meant but not limited to culture media components such as horse serum, fetal bovine serum and enzyme solutions for cell harvest. Enzyme solutions include trypsins (animal-derived, microbial-derived, or recombinant), various collagenases, alternative microbial-derived enzymes, dissociation agents, general proteases, or mixtures of these. Removal of these components provide for safe administration of TRC to a subject in need thereof Preferably, the TRC compositions of the invention contain less than 10, 5, 4, 3, 2, 1 µg/ml bovine serum albumin; less than 5, 4, 3, 2, 1, 0.9, 0.8, 0.7, 0.6, 0.5 µg/ml harvest enzymes (as determined by enzymatic activity) and are substantially free of mycoplasm, endotoxin and microbial (e.g., aerobic, anaerobic and fungi) contamination.

By substantially free of endotoxin is meant that there is less endotoxin per dose of TRCs than is allowed by the FDA for a biologic, which is a total endotoxin of 5 EU/kg body weight per day, which for an average 70 kg person is 350 EU per total dose of TRCs.

By substantially free for mycoplasma and microbial contamination is meant as negative readings for the generally accepted tests know to those skilled in the art. For example, mycoplasm contamination is determined by subculturing a TRC product sample in broth medium and distributed over agar plates on day 1, 3, 7, and 14 at 37° C. with appropriate positive and negative controls. The product sample appearance is compared microscopically, at 100×, to that of the positive and negative control. Additionally, inoculation of an indicator cell culture is incubated for 3 and 5 days and examined at 600× for the presence of mycoplasmas by epifluorescence microscopy using a DNA-binding fluorochrome. The product is considered satisfactory if the agar and/or the broth media procedure and the indicator cell culture procedure show no evidence of mycoplasma contamination.

The sterility test to establish that the product is free of microbial contamination is based on the U.S. Pharmacopedia Direct Transfer Method. This procedure requires that a pre-harvest medium effluent and a pre-concentrated sample be inoculated into a tube containing tryptic soy broth media and fluid thioglycollate media. These tubes are observed periodically for a cloudy appearance (torpidity) for a 14 day incubation. A cloudy appearance on any day in either medium indicate contamination, with a clear appearance (no growth) testing substantially free of contamination.

The ability of cells within TRCs to form clonogenic colonies compared to BM-MNCs was determined. Both hematopoietic (CFU-GM) and mesenchymal (CFU-F) colonies were monitored (Table 1). As shown in Table 1, while CFU-F were increased 280-fold, CFU-GM were slightly decreased by culturing.

TABLE 1

|  | BM MNC Input (E−06) | TRC Output (E−06) | Fold Exp |
| --- | --- | --- | --- |
| CFU-GM | 1.7 | 1.1 ± 0.2 | 0.7 ± 0.1 |
| CFU-F | 0.03 | 6.7 ± 1.3 | 280 ± 67 |

Results are the average ± SEM from 8 clinical-scale experiments.

The cells of the TRC composition have been characterized by cell surface marker expression. Table 2 shows the typical phenotype measured by flow cytometry for starting BM MNCs and TRCs. (See, Table 2) These phenotypic and functional differences highly differentiate TRCs from the mononuclear cell starting compositions.

TABLE 2

| Lineage | Marker | BM MNC Input | | TRC Output | | Fold Expansion |
| --- | --- | --- | --- | --- | --- | --- |
| | | % | Total (in millions) | % | Total (in millions) | |
| M | CD105/166 | 0.03 | 0.1 | 12 | 16 | 373 |
| H | CD14auto+ | 0.2 | 0.5 | 26 | 36 | 81 |
| M | CD90 | 0.4 | 0.9 | 22 | 28 | 39 |
| H (E) | CXCR4/VEGFR1 | 0.7 | 1.9 | 12 | 9.9 | 21 |
| E | CD144/146 | 0.5 | 1.3 | 2.7 | 3.2 | 6.3 |
| E | VEGFR1 | 7.6 | 22 | 26 | 38 | 2.3 |
| E | VEGFR2 | 12 | 37 | 25 | 37 | 1.3 |
| H | CD14auto− | 11 | 31 | 14 | 17 | 0.9 |
| H | CD11b | 59 | 162 | 64 | 83 | 0.5 |
| H | CD45 | 97 | 269 | 80 | 104 | 0.4 |
| H | CD3 | 24 | 67 | 8.6 | 11 | 0.2 |

M = mesenchymal lineage,
H = hematopoietic lineage,
E = endothelial lineage.
Results are the average of 4 clinical-scale experiments.

Figure 38:
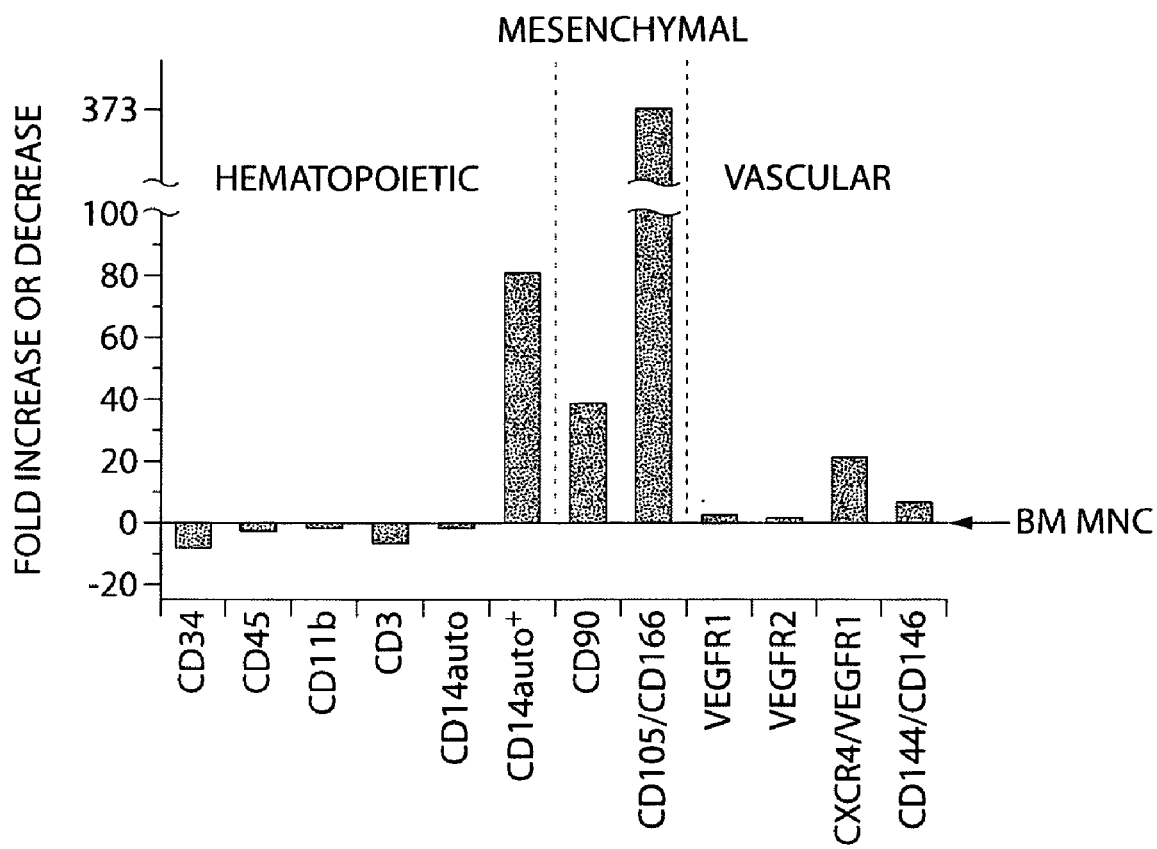
FIG. 38 is a bar chart showing the increase or decrease of certain cell types in TRCs compared to BM MNCs.

Markers for hematopoietic, mesenchymal, and endothelial lineages were examined. Average results from 4 experiments comparing starting BM MNC and TRC product are shown in FIG. 38. Most hematopoietic lineage cells, including CD11b myeloid, CD14auto− monocytes, CD34 progenitor, and CD3 lymphoid, are decreased slightly, while CD14auto+ macrophages, are expanded 81-fold. The mesenchymal cells, defined by CD90$^+$ and CD105+/166+/45−/14− have expansions up to 373-fold. Cells that may be involved in vascularization, including mature vascular endothelial cells (CD144/146) and CXCR4/VEGFR1+ supportive cells are expanded from 6- to 21-fold.

Figure 39:
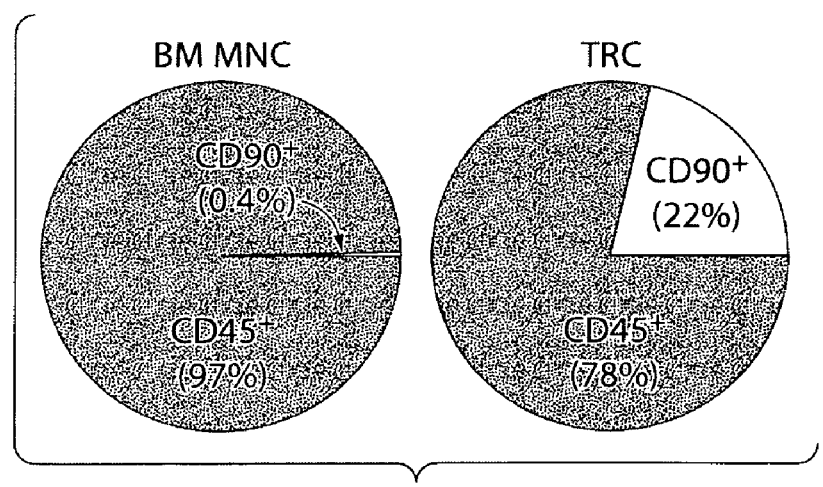
FIG. 39 is a illustration showing the frequency of hematopoietic and mesenchymal elements in BM MNCs and TRCs.

Although most hematopoietic lineage cells do not expand in these cultures, the final product still contains close to 80% CD45+ hematopoietic cells and approximately 20% CD90+ mesenchymal cells (FIG. 39).

The TRC are highly enriched for CD90$^+$ cells compared to the mononuclear cell population from which they are derived. The cells in the TRC composition are at least 5%, 10%, 25%, 50%, 75%, or more CD90$^+$. The remaining cells in the TRC composition are CD45$^+$. Preferably, the cells in the TRC composition are about 5-75% viable CD90$^+$. In various aspects, at least 5%, 10%, 15%, 20%, 25%, 30%, 40%, 50%, 60% or more of the CD90$^+$ are also CD15$^+$. (See Table 3) In addition, the CD90$^+$ are also CD105$^+$.

TABLE 3

|  | TRC Run 1 | TRC Run 2 |
| --- | --- | --- |
| % CD90+ | 29.89 | 18.08 |
| % CD90+ CD15− | 10.87 | 3.18 |
| % CD90+ CD15+ | 19.02 | 14.90 |
| % CD15+ of the CD90s | 63.6 | 82.4 |

In contrast, the CD90 population in bone marrow mononuclear cells (BMMNC) is typically less than 1% with the resultant CD45$^+$ cells making up greater than 99% of the nucleated cells in BMMNCs Thus, there is a significant reduction of many of the mature hematopoietic cells in the TRC composition compared to the starting mononuclear cell population. (See Table 2)

This unique combination of hematopoietic, mesenchymal and endothelial stems cells are not only distinct from mononuclear cells but also other cell populations currently being used in cell therapy. Table 4 demonstrates the cell surface marker profile of TRC compared to mesenchymal stem cells and adipose derived stem cells. (Deans R J, Moseley A B. 2000. Exp. Hematol. 28: 875-884; Devine S M. 2002. J Cell Biochem Supp 38: 73-79; Katz A J, et al. 2005. Stem Cells. 23:412-423; Gronthos S, et al. 2001. J Cell Physiol 189:54-63; Zuk P A, et al. 2002. Mol Biol Cell. 13: 4279-95.)

For example, Mesenchymal stem cells (MSCs) are highly purified for CD90$^+$ (greater than 95% CD90$^+$), with very low percentage CD45$^+$ (if any). Adipose-derived stem cells are more variable but also typically have greater than 95% CD90$^+$, with almost no CD45$^+$ blood cells as part of the composition. There are also Multi-Potent Adult Progenitor Cells (MAPCs), which are cultured from BMMNCs and result in a pure CD90 population different from MSCs that co-expresses CD49c. Other stem cells being used are highly purified cell types including CD34$^+$ cells, AC133$^+$ cells, and $^+$CD34$^+$lin$^-$ cells, which by nature have little to no CD90$^+$ cells as part of the composition and thus are substantially different from TRCs.

Cell marker analysis have also demonstrated that the TRCs isolated according to the methods of the invention have higher percentages of CD14$^+$ auto$^+$, CD34$^+$ and VEGFR$^+$ cells.

TABLE 4

| CD Locus | Common Name | TRC | Mesenchymal stem cells | Adipose-Derived Stem Cells |
|---|---|---|---|---|
| CD 34 | — | + | − | ± |
| CD13 | gp150 | + | Na | + |
| CD15 | LewisX, SSEA-1 | + | − | − |
| CD11b | Mac-1 | + | − | ± |
| CD14 | LPS receptor | + | − | − |
| CD235a | glycophorin A | + | Na | Na |
| CD45 | Leukocyte common antigen | + | − | − |
| CD90 | Thy1 | + | + | + |
| CD105 | Endoglin | + | + | + |
| CD166 | ALCAM | + | + | + |
| CD44 | Hyaluronate receptor | + | + | + |
| CD133 | AC133 | + | − | ± |
| — | vWF | + | Na | Na |
| CD144 | VE-Cadherin | + | − | + |
| CD146 | MUC18 | + | + | Na |
| CD309 | VEGFR2, KDR | + | Na | Na |

Each of the cell types present in a TRC population have varying immunomodulatory properties. Monocytes/macrophages (CD45$^+$, CD14$^+$) inhibit T cell activation, as well as showing indoleamine 2,3-dioxygenase (IDO) expression by the macrophages. (Munn D. H. and Mellor A. L., Curr Pharm Des., 9:257-264 (2003); Munn D. H., et al J Exp Med., 189: 1363-1372 (1999); Mellor A. L. and Munn D. H., J. Immunol., 170:5809-5813 (2003); Munn D H., et al., J. Immunol., 156:523-532 (1996)). The monocytes and macrophages regulate inflammation and tissue repair. (Duffield J. S., Clin Sci (Lond), 104:27-38 (2003); Gordon, S.; Nat. Rev. Immunol., 3:23-35 (2003); Mosser, D. M., J. Leukoc. Biol., 73:209-212 (2003); Philippidis P., et al, Circ. Res., 94:119-126 (2004). These cells also induce tolerance and transplant immunosuppression. (Fandrich F et al. Hum. Immunol., 63:805-812 (2002)). Regulatory T-cells (CD45$^+$ CD4$^+$ CD25$^+$) regulate innate inflammatory response after injury. (Murphy T. J., et al., J. Immunol., 174:2957-2963 (2005)). The T-cells are also responsible for maintenance of self tolerance and prevention and suppression of autoimmune disease. (Sakaguchi S. et al., Immunol. Rev., 182:18-32 (2001); Tang Q., et al., J. Exp. Med., 199:1455-1465 (2004)) The T-cells also induce and maintain transplant tolerance (Kingsley C. I., et al. J. Immunol., 168:1080-1086 (2002); Graca L., et al., J. Immunol., 168:5558-5565 (2002)) and inhibit graft versus host disease (Ermann J., et al., Blood, 105:2220-2226 (2005); Hoffmann P., et al., Curr. Top. Microbiol. Immunol., 293:265-285 (2005); Taylor P. A., et al., Blood, 104:3804-3812 (2004). Mesenchymal stem cells (CD45$^+$ CD90$^+$ CD105$^+$) express IDO and inhibit T-cell activation (Meisel R., et al., Blood, 103:4619-4621 (2004); Krampera M., et al., Stem Cells, (2005)) as well as induce anti-inflammatory activity (Aggarwal S. and Pittenger M. F., Blood, 105:1815-1822 (2005)).

TRCs also show increased expression of programmed death ligand 1 (PDL1). Increased expression of PDL1 is associated with production of the anti-inflammatory cytokine IL-10. PDL1 expression is associated with a non-inflammatory state. TRCs have increased PDL1 expression in response to inflammatory induction, showing another aspect of the anti-inflammatory qualities of TRCs.

Figure 40:
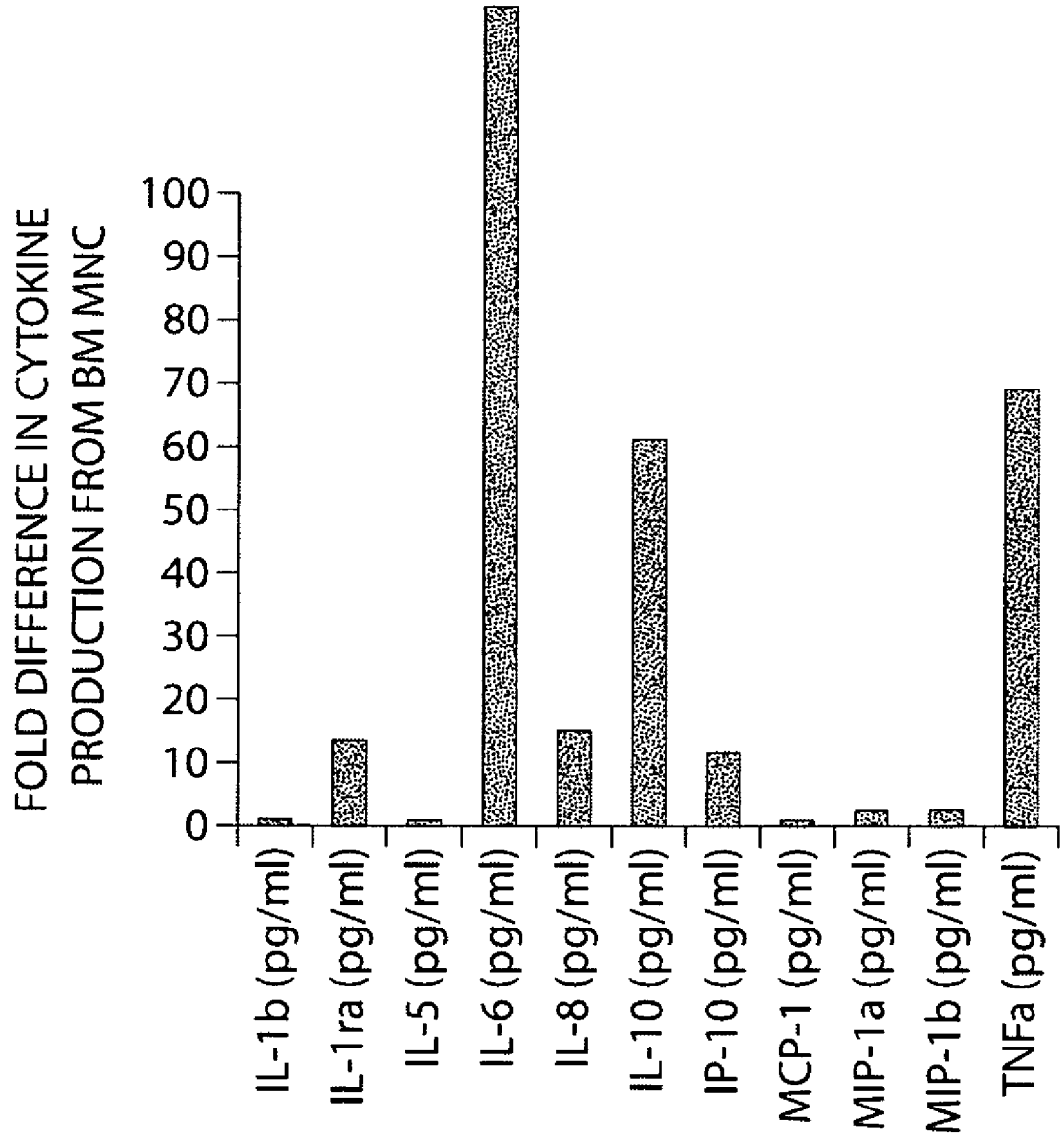
FIG. 40 is a bar chart showing that the cytokine production profiles are significantly different between BM MNCs and TRCs from the same donor.

TRCs, in contrast to BM MNCs also produce at least five distinct cytokines and one regulatory enzyme with potent activity both for wound repair and controlled down-regulation of inflammation. (FIG. 40) Specifically, TRCs produce 1) Interleukin-6 (IL-6), 2) Interleukin-10 (IL-10), 3) vascular endothelial growth factor (VEGF), 4) monocyte chemoattractant protein-1 (MCP-1) and, 5) interleukin-1 receptor antagonist (IL-1ra). The characteristics of these five cytokines is summarized in Table 5, below.

TABLE 5

Characteristics of TRC Expressed Cytokines.

| CYTOKINE | CHARACTERISTIC |
|---|---|
| IL-1 ra | Decoy receptor for IL-1 down-regulates inflammation. IL-1 ra and IL-10 are characteristically produced by alternatively activated macrophages |
| IL-6 | Interleukin-6 (IL-6) is a pleiotropic cytokine with a wide range of biological activities. This cytokine regulates polarization of naive CD4$^+$ T-cells toward the Th2 phenotype, further promotes Th2 differentiation by up-regulating NFAT1 expression and inhibits proinflammatory Th1 differentiation by inducing suppressor of cytokine signaling SOCS1. |
| IL-10 | Produced by cell types mediating anti-inflammatory activities, Th2 type immunity, immunosuppression and tissue repair. IL-10 and IL-1ra are characteristically produced by alternatively activated macrophages. IL-10 also is involved in the induction of regulatory T-cells. In addition, regulatory T-cells secrete high levels of IL-10. |

TABLE 5-continued

Characteristics of TRC Expressed Cytokines.

| CYTOKINE | CHARACTERISTIC |
|---|---|
| MCP-1 | MCP-1 inhibits the adoptive transfer of autoimmune disease in animal models and drives TH2 differentiation indicating an anti inflammatory property particularly when balanced a against MIP-1α. |
| VEGF | Angiogenic cytokine with simultaneous immunosuppressive properties acting at the level of the antigen presenting cell. |

Additional characteristics of TRCs include a failure spontaneously to produce, or very low-level production of certain pivotal mediators known to activate the TH1 inflammatory pathway including interleukin-alpha (IL-1a), interleukin-beta (IL-1β) interferon -gamma (IFNγ) and most notably interleukin-12 (IL-12). Importantly, the TRCs neither produce these latter TH1-type cytokines spontaneously during medium replacement or perfusion cultures nor after intentional induction with known inflammatory stimuli such as bacterial lipopolysaccharide (LPS). TRCs produced low levels of IFNγ only after T-cell triggering by anti-CD3 mAb. Finally, the TRCs produced by the current methods produce more of the anti-inflammatory cytokines IL-6 and IL-10 as well as less of the inflammatory cytokine IL-12.

Moreover, TRCs are inducible for expression of a key immune regulatory enzyme designated indoleamine-2,-3 dioxygenase (IDO). The TRCs according to the present invention express higher levels of IDO upon induction with interferon γ. IDO has been demonstrated to down-regulate both nascent and ongoing inflammatory responses in animal models and humans (Meisel R., et al., Blood, 103:4619-4621 (2004); Munn D. H., et al., J. Immunol., 156:523-532 (1996); Munn D. H., et al. J. Exp. Med. 189:1363-1372 (1999); Munn D. H. and Mellor A. L., Curr. Pharm. Des., 9:257-264 (2003); Mellor A. L. and Munn D. H., J. Immunol., 170:5809-5813 (2003)).

Together, these unique characteristics of the TRCs according to the invention create a more anti-inflammatory environment for tissue repair, and therefore are more effective treatment for tissue repair.

As discussed above, TRCs are highly enriched for a population of cells that co-express CD90 and CD15.

CD90 is present on a stem and progenitor cells that can differentiate into multiple lineages. These cells are a heterogeneous population of cells that are most likely at different states of differentiation. Cell markers have been identified on stem cells of embryonic or fetal origin that define the stem-cell state of the cell. One of these markers, SSEA-1, also referred to as CD15. CD15 is found on mouse embryonic stem cells, but is not expressed on human embryonic stem cells. It has however been detected in neural stem cells from both mouse and human. CD15 is also not expressed on purified mesenchymal stem cells derived from human bone marrow or adipose tissue (see Table 6). Thus, the cell population in TRCs that co -express both CD90 and CD15 are a unique cell population and may define a the stem-like state of the CD90 adult-derived cells.

Accordingly, in another aspect of the invention the cell population expressing both CD90 and CD15 may be further enriched. By further enriched is meant that the cell composition contains 5%, 10%, 25%, 50%, 75%, 80%, 85%, 90%, 95%, 96%, 97%, 98% 99% or 100% CD90$^+$ CD15$^+$ cells. TRCs can be further enriched for CD90$^+$ CD15$^+$ cells by methods known in the art such as positive or negative selection using antibodies direct to cell surface markers. The TRCs that have been further enriched for CD90$^+$ CD15$^+$ cells are particularly useful in bone repair and regeneration.

TABLE 6

| Cell Phenotype | TRC | MSC P0 |
|---|---|---|
| % CD90+ | 23.99 | 98.64 |
| % CD15+ | 39.89 | 0.76 |
| % CD15+/CD90+ | 19.54 | 0.22 |
| N | 2 | 4 |

Figure 41A:
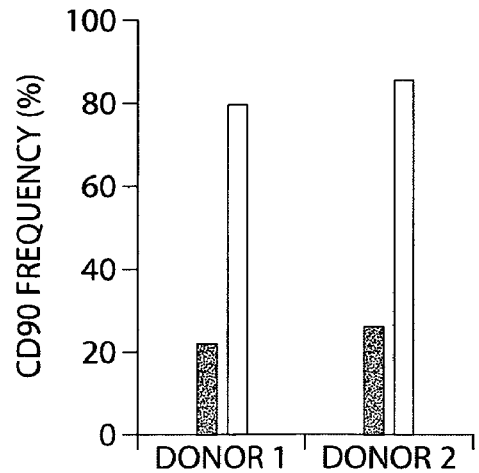
FIG. 41A-C is a series of bar charts showing the frequency of CD90 and CFU-f in MSC and TRC cultures. MSC and TRC were generated in the automated bioreactor system as described in Materials and Methods. The frequency of CD90 and CFU-f in the output culture are shown in A. and B. respectively. The CFU-f frequency was then calculated based on the number of CD90 cells in each product. Results are shown in C. Dark bars represent TRC cultures and open bars represent MSC cultures. Two independent normal donors are shown.
Figure 41B:
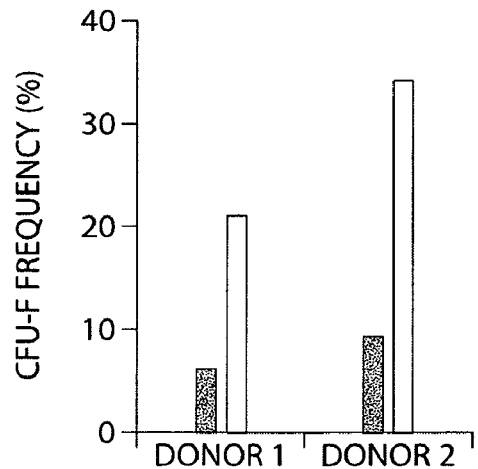
Figure 41C:
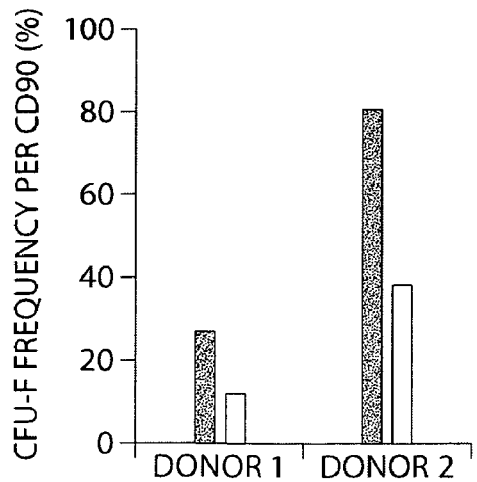

The CFU-F and osteogenic potential of CD90$^+$ CD15$^+$ was assessed. When CD90$^+$ cells are removed, all CFU-F and in vitro osteogenic potential is depleted. Suprisingly, although the overall frequency of CD90 and CFU-F are higher in MSC cultures (where CD90 do not express CD15), the relative number of CFU-F per CD90 cells is dramtically higher in TRC. (FIG. 41) This demonstrates that the CD90 cells are much more potent in TRCs that when grown as purified cell polulations.

Figure 42:
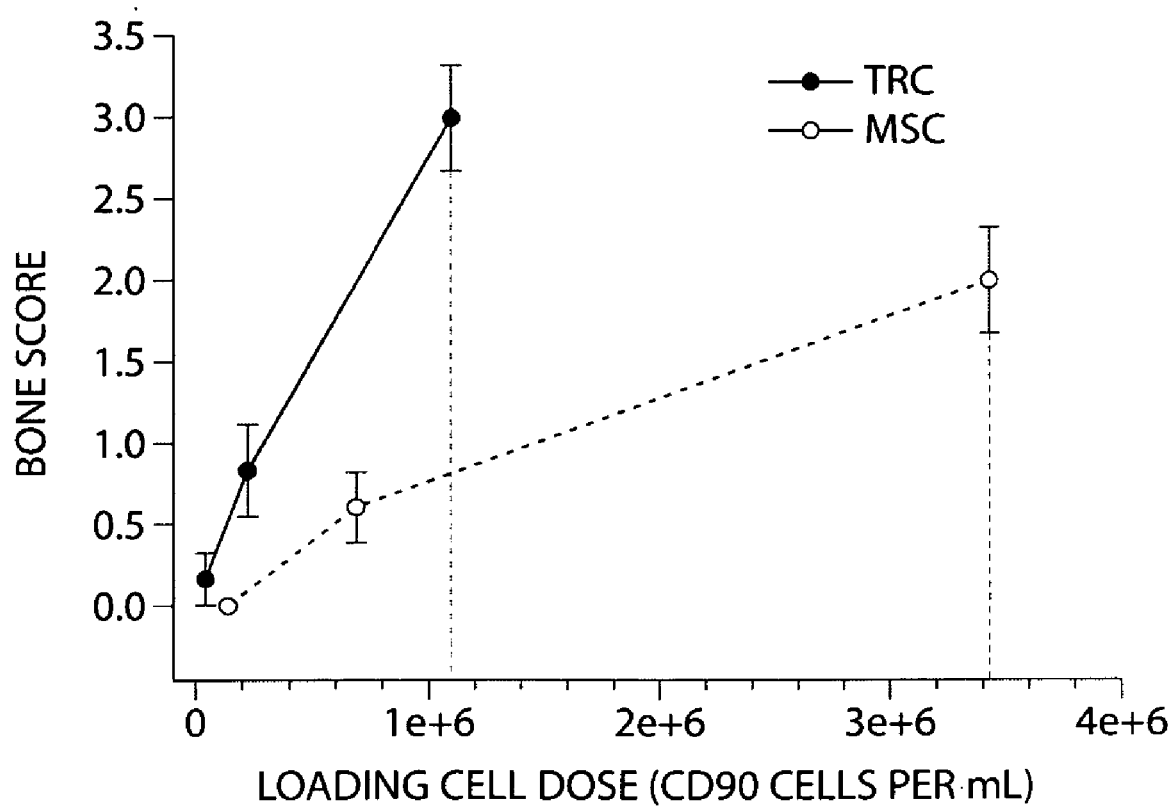
FIG. 42 is a line graph showing comparison of bone formation in vivo in an ectopic mouse model. Bone scores were determined for each loading cell density from MSC and TRC cultures. the graph shows the calculated loading dose of CD90+ cells from each culture. The results presented are representative experiment from one normal donor. In this experiment, MRC were 68% CD90$^+$ and TRCs were 22% cCD0$^+$.

Osteogenic potential was measured both in vitro and in vivo. Again, in conditions where cells are expressing CD15 (TRC), the osteogenic potential was higher than that found in mesenchymal cells (FIG. 42)

Therapeutic Methods

Tissue Repair Cells (TRCs) are useful for a variety of therapeutic methods including, tissue repair, tissue regeneration, and tissue engineering. For example, the TRC are useful in bone regeneration, cardiac regeneration, vascular regeneration, neural regeneration and the treatment of ischemic disorders. Ischemic conditions include, but are not limited to, limb ischemia, congestive heart failure, cardiac ischemia, kidney ischemia and ESRD, stroke, and ischemia of the eye. Additionally, because of the immuno-regulatory cytokines produced by the TRCs, the TRCs are also useful in the treatment of a variety of immune and inflammatory disease. Immune and inflammatory disease include for example, diabetes (Type I and Type II), inflammatory bowel diseases (IBD), graft verses host disease (GVHD), psoriasis, rejection of allogeneic cells, tissues or organs (tolerance induction), heart disease, spinal cord injury, rheumatoid arthritis, osteoarthritis, inflammation due to hip replacement or revision, Crohn's disease, autoimmune diseases such as system lupus erythematosus (SLE), rheumatoid arthritis (RA), and multiple sclerosis (MS). In another aspect of the invention TRCs are also useful for inducing angiogenesis.

TRCs are administered to mammalian subjects, e.g., human, to effect tissue repair or regeneration. The TRCs are administered allogeneically or autogeneically.

TRCs unique qualities strongly polarize the host response away from the tissue-destructive pathway of inflammation and toward wound repair with rapid healing of injured tissues. Furthermore, some of the cells are capable of tissue specific differentiation (e.g., CD90$^+$ to bone), further aiding tissue regeneration. Accordingly, TRCs are effective for inducing tissue repair in a wide range of diseases.

Pharmaceutical Administration and Dosage Forms

The described TRCs can be administered as a pharmaceutically or physiologically acceptable preparation or composition containing a physiologically acceptable carrier, excipient, or diluent, and administered to the tissues of the recipient organism of interest, including humans and non-human animals. TRC-containing composition can be prepared by resuspending the cells in a suitable liquid or solution such as sterile physiological saline or other physiologically acceptable injectable aqueous liquids. The amounts of the components to be used in such compositions can be routinely determined by those having skill in the art.

The TRCs or compositions thereof can be administered by placement of the TRC suspensions onto absorbent or adherent material, i.e., a collagen sponge matrix, and insertion of the TRC-containing material into or onto the site of interest. Alternatively, the TRCs can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the TRCs can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

Consistent with the present invention, the TRC can be administered to body tissues, including liver, pancreas, lung, salivary gland, blood vessel, bone, skin, cartilage, tendon, ligament, brain, hair, kidney, muscle, cardiac muscle, nerve, skeletal muscle, joints, and limb.

The number of cells in a TRC suspension and the mode of administration may vary depending on the site and condition being treated. As non-limiting examples, in accordance with the present invention, about 35-300×10$^6$ TRCs are injected to effect tissue repair. Consistent with the Examples disclosed herein, a skilled practitioner can modulate the amounts and methods of TRC-based treatments according to requirements, limitations, and/or optimizations determined for each case.

In preferred embodiments, the TRC pharmaceutical composition comprises between about 8 and 54% CD90$^+$ cells and between about 46 and 92% CD45$^+$ cells. The TRC pharmaceutical composition preferably contains between about 35×10$^6$ and 300×10$^6$ viable nucleated cells and between about 7×10$^6$ and 75×10$^6$ viable CD90$^+$ cells. The TRC pharmaceutical compositional preferably has less than 0.5 EU/ml of endotoxin and no bacterial or fungal growth. In preferred embodiments, a dosage form of TRCs is comprised within 4.7-7.3 mL of pharmaceutically acceptable aqueous carrier. The preferred suspension solution is Multiple Electrolyte Injection Type 1 (USP/EP). Each 100 mL of Multiple Electrolyte Injection Type 1 contains 234 mg of Sodium Chloride, USP (NaCl); 128 mg of Potassium Acetate, USP ($C_2H_3KO_2$); and 32 mg of Magnesium Acetate Tetrahydrate (Mg $(C_2H_3O_2)_2.4H_2O$). It contains no antimicrobial agents. The pH is adjusted with hydrochloric acid. The pH is 5.5 (4.0 to 8.0). The Multiple Electrolyte Injection Type 1 is preferably supplemented with 0.5% human serum albumin (USP/EP). Preferably, the TRC pharmaceutical composition is stored at 0-12° C., unfrozen.

Indications and Modes of Delivery for TRCs

TRCs may be manufactured and processed for delivery to patients using the described processes where the final formulation is the TRCs with all culture components substantially removed to the levels deemed safe by the FDA. It is critical for the cells to have a final viability greater than 70%, however the higher the viability of the final cell suspension the more potent and efficacious the final cell dose will be, and the less cellular debris (cell membrane, organelles and free nucleic acid from dead cells), so processes that enhance cell viability while maintaining the substantially low culture and harvest components, while maintaining closed aseptic processing systems are highly desirable.

Limb Ischemia

It has been demonstrated that bone marrow-derived cells are used for vascular regeneration in patients with critical limb ischemia, peripheral vascular disease, or Burger's syndrome. The TRCs delivered to patients with ischemic limbs, and have been shown to enhance vascular regeneration. TRCs are delivered to patients by creating a cell suspension and removing the TRCs from the supplied bag or vial that they are delivered in. A syringe is used to remove the TRC suspension, and then smaller 0.25 ml to 1 ml individual injection volumes are loaded from the main syringe using a syringe adaptor, and then several individual injection volumes are delivered via intramuscular injection to the site of limb ischemia and where vascular formation is required. The TRCs may be delivered through a wide range of needle sizes, from large 16 gauge needles to very small 30 gauge needles, as well as very long 28 gauge catheters for minimally invasive procedures. Alternatively, the TRCs may also be delivered intravascularly and allowed to home to the site of ischemia to drive local tissue regeneration.

Cardiac Regeneration

There are a variety of modes of delivery for driving cardiac tissue regeneration. The TRCs are delivered intra-vascularly and allowed to home to the site of regeneration. Alternatively, the TRCs are also be delivered directly into the cardiac muscle, either epicardially or endocardially, as well as transvascularly. The TRCs may be delivered during an open-chest procedure, or via minimally invasive procedures such as with delivery via catheter. The TRCs are delivered to these patients by creating a cell suspension and removing the TRCs from the supplied bag or vial that they are delivered in. A syringe is used to remove the TRC suspension, and then smaller 0.25 ml to 1 ml individual injection volumes are loaded from the main syringe using a syringe adaptor, and then several individual injection volume are delivered via intramuscular injection to the site of cardiac ischemia and where vascular formation is required. The TRCs may be delivered through a wide range of needle sizes, from large 16 gauge needles to very small 30 gauge needles, as well as very long 28 gauge catheters for minimally invasive procedures.

Spinal Cord Regeneration

There are a variety of ways that TRCs are used for regeneration after spinal cord injury (SCI). TRCs may be injected directly into the site of SCI, seeded onto a matrix (chosen from the list below for bone regeneration) and seeded into resected spinal cord or just placed at the site such that the TRCs may migrate to the injury site. Alternatively, the TRCs are delivered intravascularly and allowed to home to the site of injury to drive local tissue regeneration.

There are a variety of other applications where the TRCs may be delivered locally to the tissue via direct injection, seeding onto a matrix for localized delivery, or delivered via the vascular system allowing for TRCs to home to the site of injury or disease. These diseases are limb ischemia, congestive heart failure, cardiac ischemia, kidney ischemia and end stage renal disease, stroke, and ischemia of the eye.

Orthopedic Indications for Bone Regenerations

TRCs have been used successfully in bone regeneration applications in humans. Optionally, TRCs are mixed with 3D matrices to enhance delivery and localization at the site where bone regeneration is required. The three-dimensional matrices come in a range of physical and chemical forms, and viscous or gelled binding materials may also be added to aid handling and delivery properties.

Three dimensional matrices include for example, demineralized bone particles, mineralized bone particles, synthetic ceramic of the calcium phosphate family such as alpha tri-calcium phosphates (TCP), beta TCP, hydroxyappatites, and complex mixtures of these materials. Other matrices include for example, collagen-based sponges, polysaccharide-based materials such as hyaluronan and alginates, synthetic biodegradable polymeric materials such as poly-lactides, poly-glycolides, poly-fumarates, poly-ethylene glycol, co-polymers of these as well as other materials known in the art.

Any of the matrices used with TRCs may be processed into different physical forms that are common in the art for tissue regeneration applications. These physical forms are open and closed pore foams and sponges, fiber-based woven or non-woven meshes, or small particles ranging from nano-particles to micron-sized particles (1 micrometer-1000 micrometers) and macro-particles in the millimeter size scale. The small particles also often have an open porosity, with nanopores aiding in nutrient and metabolite transport and micropores providing pores large enough to facilitate cell seeding and tissue integration.

When the matrices used for cell delivery are small particles delivered to wound sites, at times viscous materials or gels are used to bind the particles that aid in materials handling and delivery, as well as helping to keep the particles and the cells localized at the site after placement. Viscous binding materials include for example, hyaluronan, alginates, collagens, poly ethylene glycols, poly fumarates, blood clots and fibrin-based clots, as well as mixtures of these materials, either in the form of viscous fluids to soft or hard hydrogels. Other viscous materials and hydrogels are known in the art In various embodiments, TRCs are delivered with TCP, demineralized bone, and mineralized bone particles in sizes ranging from 200 micrometers to 5 millimeters, depending on the specific application. Optionally, these materials are bound with fibrin-based clots made from autologous freshly prepared plasma from the patient. Other fibrin clots or different hydrogels, or matrix materials common may also be used.

Generally, TRCs are mixed with the matrices just prior to surgery when used for bone regeneration. For long-bone regeneration, typically the area of bone non-union is opened by the surgeon, and the necrotic bone is removed. The non-unioned bone or area where bone is needed may or may not be de-corticated by the surgeon to allow bleeding at the site, at which point the TRC-matrix mixture is placed by the surgeon between the bones where regeneration will occur. This mixture of the TRCs and matrix drive tissue regeneration with the physical matrix guiding the location of bone regeneration and the TRCs providing the tissue repair stimulus for driving angiogenesis, would healing, and bone regeneration. The remaining TRC/matrix mixture is optionally placed around the fracture line after any orthopedic hardware has been placed such as plates, rods, screws or nails.

Methods of Production of TRCs

TRCs are isolated from any mammalian tissue that contains bone marrow mononuclear cells (BM MNC). Suitable sources for BM MNC is peripheral blood, bone marrow, umbilical cord blood or fetal liver. Blood is often used because this tissue is easily obtained. Mammals include for example, a human, a primate, a mouse, a rat, a dog, a cat, a cow, a horse or a pig.

The culture method for generating TRCs begins with the enrichment of BM MNC from the starting material (e.g., tissue) by removing red blood cells and some of the poly-nucleated cells using a conventional cell fractionation method. For example, cells are fractionated by using a FICOLL® density gradient separation. The volume of starting material needed for culture is typically small, for example, 40 to 50 mL, to provide a sufficient quantity of cells to initiate culture. However, any volume of starting material may be used.

Nucleated cell concentration is then assessed using an automated cell counter, and the enriched fraction of the starting material is inoculated into a biochamber (cell culture container). The number of cells inoculated into the biochamber depends on its volume. TRC cultures which may be used in accordance with the invention are performed at cell densities of from $10^4$ to $10^9$ cells per ml of culture. When a Aastrom Replicell Biochamber is used $2-3 \times 10^8$ total cells are inoculated into a volume of approximately 280 mL.

Prior to inoculation, a biochamber is primed with culture medium. Illustratively, the medium used in accordance with the invention comprises three basic components. The first component is a media component comprised of IMDM, MEM, DMEM, RPMI 1640, Alpha Medium or McCoy's Medium, or an equivalent known culture medium component. The second is a serum component which comprises at least horse serum or human serum and may optionally further comprise fetal calf serum, newborn calf serum, and/or calf serum. Optionally, serum free culture mediums known in the art may be used. The third component is a corticosteroid, such as hydrocortisone, cortisone, dexamethasone, solumedrol, or a combination of these, preferably hydrocortisone. When the Aastrom Replicell Biochamber is used, the culture medium consists of IMDM, about 10% fetal bovine serum, about 10% horse serum, about 5 µM hydrocortisone, and 4 mM L-Glutamine. The cells and media are then passed through the biochamber at a controlled ramped perfusion schedule during culture process. The cells are cultures for 2, 4, 6, 8, 10, 12, 14, 16 or more days. Preferably, the cells are cultured for 12 days. For example, when used with the Aastrom Replicell System Cell Cassette, the cultures are maintained at 37° C. with 5% $CO_2$ and 20% $O_2$.

These cultures are typically carried out at a pH which is roughly physiologic, i.e. 6.9 to 7.6. The medium is kept at an oxygen concentration that corresponds to an oxygen-containing atmosphere which contains from 1 to 20 vol. percent oxygen, preferably 3 to 12 vol. percent oxygen. The preferred range of $O_2$ concentration refers to the concentration of $O_2$ near the cells, not necessarily at the point of $O_2$ introduction which may be at the medium surface or through a membrane.

Standard culture schedules call for medium and serum to be exchanged weekly, either as a single exchange performed weekly or a one-half medium and serum exchange performed twice weekly. Preferably, the nutrient medium of the culture is replaced, preferably perfused, either continuously or periodically, at a rate of about 1 ml per ml of culture per about 24 to about 48 hour period, for cells cultured at a density of from $2\times10^6$ to $1\times10^7$ cells per ml. For cell densities of from $1\times10^4$ to $2\times10^6$ cells per ml the same medium exchange rate may be used. Thus, for cell densities of about $10^7$ cells per ml, the present medium replacement rate may be expressed as 1 ml of medium per $10^7$ cells per about 24 to about 48 hour period. For cell densities higher than $10^7$ cells per ml, the medium exchange rate may be increased proportionality to achieve a constant medium and serum flux per cell per unit time A method for culturing bone marrow cells is described in Lundell, et al., "Clinical Scale Expansion of Cryopreserved Small Volume Whole Bone Marrow Aspirates Produces Sufficient Cells for Clinical Use," J. Hematotherapy (1999) 8:115-127 (which is incorporated herein by reference). Bone marrow (BM) aspirates are diluted in isotonic buffered saline (Diluent 2, Stephens Scientific, Riverdale, N.J.), and nucleated cells are counted using a Coulter ZM cell counter (Coulter Electronics, Hialeah, Fla.). Erythrocytes (non-nucleated) are lysed using a Manual Lyse (Stephens Scientific), and mononuclear cells (MNC) are separated by density gradient centrifugation (Ficoll-Paque® Plus, Pharmacia Biotech, Uppsala, Sweden) (specific gravity 1.077) at 300 g for 20 min at 25° C. BM MNC are washed twice with long-term BM culture medium (LTBMC) which is Iscove's modified Dulbecco's medium (IMDM) supplemented with 4 mM L-glutamine 9GIBCO BRL, Grand Island, N.Y.), 10% fetal bovine serum (FBS), (Bio-Whittaker, Walkersville, Md.), 10% horse serum (GIBCO BRL), 20 µg/ml vancomycin (Vancocin® HCl, Lilly, Indianapolis, Ind.), 5 µg/ml gentamicin (Fujisawa USA, Inc., Deerfield, Ill.), and 5 µM hydrocortisone (Solu-Cortef®, Upjohn, Kalamazoo, Mich.) before culture.

Cell Storage

After culturing, the cells are harvested, for example using trypsin, and washed to remove the growth medium. The cells are resuspended in a pharmaceutical grade electrolyte solution, for example Isolyte (B. Braun Medical Inc., Bethlehem, Pa.) supplemented with serum albumin. Alternatively, the cells are washed in the biochamber prior to harvest using the wash harvest procedure described below. Optionally after harvest the cells are concentrated and cryopreserved in a biocompatible container, such as 250 ml cryocyte freezing containers (Baxter Healthcare Corporation, Irvine, Calif.) using a cryoprotectant stock solution containing 10% DMSO (Cryoserv, Research Industries, Salt Lake City, Utah), 10% HSA (Michigan Department of Public Health, Lansing, Mich.), and 200 µg/ml recombinant human DNAse (Pulmozyme®, Genentech, Inc., South San Francisco, Calif.) to inhibit cell clumping during thawing. The cryocyte freezing container is transferred to a precooled cassette and cryopreserved with rate-controlled freezing (Model 1010, Forma Scientific, Marietta, Ohio). Frozen cells are immediately transferred to a liquid nitrogen freezer (CMS-86, Forma Scientific) and stored in the liquid phase. Preferred volumes for the concentrated cultures range from about 5 mL to about 15 ml. More preferably, the cells are concentrated to a volume of 7.5 mL.

Post-Culture

When harvested from the biochamber the cells reside in a solution that consists of various dissolved components that were required to support the culture of the cells as well as dissolved components that were produced by the cells during the culture. Many of these components are unsafe or otherwise unsuitable for patient administration. To create cells ready for therapeutic use in humans it is therefore required to separate the dissolved components from the cells by replacing the culture solution with a new solution that has a desired composition, such as a pharmaceutical-grade, injectable, electrolyte solution suitable for storage and human administration of the cells in a cell therapy application.

A significant problem associated with many separation processes is cellular damage caused by mechanical forces applied during these processes, exhibited, for instance, by a reduction in viability and biological function of the cells and an increase in free cellular DNA and debris. Additionally, significant loss of cells can occur due to the inability to both transfer all the cells into the separation apparatus as well as extract all the cells from the apparatus.

Separation strategies are commonly based on the use of either centrifugation or filtration. An example of centrifugal separation is the COBE 2991 Cell Processor (COBE BCT) and an example of a filtration separation is the CYTOMATE® Cell Washer (Baxter Corp) (Table 7). Both are commercially available state-of-the-art automated separation devices that can be used to separate (wash) dissolved culture components from harvested cells. As can be seen in Table 7, these devices result in a significant drop in cell viability, a reduction in the total quantity of cells, and a shift in cell profile due to the preferential loss of the large and fragile $CD14^+auto^+$ subpopulation of TRCs.

TABLE 7

Performance of 2 different cell separation devices, 3 different studies.

| | COBE 2991 Cell Processor (n = 3) | CYTOMATE ® Cell Washer (n = 8) | CYTOMATE ® Cell Washer (n = 26) |
|---|---|---|---|
| Operating principal | Centrifugation | Filtration | Filtration |
| Study Reference | Aastrom internal protocol report #PABI0043 | Aastrom new wash process development, report MF#0384 | US Fracture Clinical Trial, BB-IND #10486 |
| Average pre-separation cell viability | 93% | 93% | 95% |
| Average post-separation cell viability | 83% | 71% | 81% |
| Average reduction in $CD14^+Auto^+$ frequency | 18% | 69% | Not available |
| Average cell recovery | 73% | 74% | Not available |

These limitations in the art create difficulties in implementing manufacturing and production processes for creating cell populations suitable for human use. It is desirable for the separation process to minimize damage to the cells and thereby result in a cell solution that is depleted of unwanted dissolved components while retaining high viability and biological function with minimal loss of cells. Additionally, it is important to minimize the risk of introducing microbial contaminants that will result in an unsafe final product. Less manipulation and transfer of the cells will inherently reduce this risk.

The invention described in this disclosure overcomes all of these limitations in the current art by implementing a separation process to wash the cells that minimizes exposure of the cells to mechanical forces and minimizes entrapment of cells that cannot be recovered. As a result, damage to cells (e.g. reduced viability or function), loss of cells, and shift in cell profile are all minimized while still effectively separating unwanted dissolved culture components. In a preferred implementation, the separation is performed within the same device that the cells are cultured in which eliminates the added risk of contamination by transfer and separation using another apparatus. The wash process according to the invention is described below.

Wash Harvest

As opposed to conventional culture processes where cells are removed (harvested) from the biochamber followed by transfer to another apparatus to separate (wash) the cells from culture materials, the wash-harvest technique reverses the order and provides a unique means to complete all separation (wash) steps prior to harvest of the cells from the biochamber.

To separate the culture materials from the cells, a new liquid of desired composition (or gas) may be introduced, preferably at the center of the biochamber and preferably at a predetermined, controlled flow rate. This results in the liquid being displaced and expelled along the perimeter of the biochamber, for example, through apertures 48, which may be collected in the waste bag 76.

In some embodiments of the invention, the diameter of the liquid space in the biochamber is about 33 cm, the height of the liquid space is about 0.33 cm and the flow rates of adding rinsing and/or harvesting fluids to the biochamber is about 0.03 to 1.0 volume exchanges (VE) per minute and preferably 0.50 to about 0.75 VE per minute. This substantially corresponds to about 8.4 to about 280 mL/min and preferably 140 to about 210 ml/min. The flow rates and velocities, according to some embodiments, aid in insuring that a majority of the cultured cells are retained in the biochamber and not lost into the waste bag and that an excessively long time period is not required to complete the process. Generally, the quantity of cells in the chamber may range from $10^4$ to $10^8$ cell/mL. For TRCs, the quantity may range from $10^5$ to $10^6$ cells/mL, corresponding to 30 to 300 million total cells for the biochamber dimensions above. Of course, one of skill in the art will understand that cell quantity changes upon a change in the biochamber dimensions According to some embodiments, in harvesting the cultured cells from the biochamber, the following process may be followed, and is broadly outlined in Table 3, below. The solutions introduced into the biochamber are added into the center of the biochamber. The waste media bag 76 may collect corresponding fluid displaced after each step where a fluid or gas is introduced into the biochamber. Accordingly, after cells are cultured, the biochamber is filled with conditioned culture medium (e.g., IMDM, 10% FBS, 10% Horse Serum, metabolytes secreted by the cells during culture) and includes between about 30 to about 300 million cells. A 0.9% NaCl solution ("rinse solution") may then be introduced into the biochamber at about 140 to 210 mL per minute until about 1.5 to about 2.0 liters of total volume has been expelled from the biochamber (Step 1).

While a single volume exchange for introduction of a new or different liquid within the biochamber significantly reduces the previous liquid within the biochamber, some amount of the previous liquid will remain. Accordingly, additional volume exchanges of the new/different liquid will significantly deplete the previous liquid.

Optionally, when the cells of interest are adherent cells, such as TRCs, the rinse solution is replaced by harvest solution. A harvest solution is typically an enzyme solution that allows for the detachment of cells adhered to the culture surface. Harvest solutions include for example 0.4% Trypsin/EDTA in 0.9% NaCl that may be introduced into the biochamber at about 140 to 210 mL per minute until about 400 to about 550 ml of total volume has been delivered (Step 2). Thereafter, a predetermined period of time elapses (e.g., 13-17 minutes) to allow enzymatic detachment of cells adhered to the culture surface of the biochamber (Step 3).

Isolyte (B Braun) supplemented with 0.5% HSA may be introduced at about 140 to 210 mL per minute until about 2 to about 3 liters of total volume has been delivered, to displace the enzyme solution (Step 4).

At this point, separation of unwanted solutions (culture medium, enzyme solution) from the cells is substantially complete.

To reduce the volume collected, some of the Isolyte solution is preferably displaced using a gas (e.g., air) which is introduced into the biochamber at a disclosed flow rate (Step 5). This may be used to displace approximately 200 to 250 cc of the present volume of the biochamber.

The biochamber may then be agitated to bring the settled cells into solution (Step 6). This cell suspension may then be drained into the cell harvest bag 70 (or other container) (Step 7). An additional amount of the second solution may be added to the biochamber and a second agitation may occur in order to rinse out any other residual cells (Steps 8 & 9). This final rinse may then be added to the harvest bag 70 (Step 10).

TABLE 8

Wash-harvest Protocol

| Step Number & Name | Description |
| --- | --- |
| 1 Rinse out culture media | Use Sodium Chloride to displace the culture medium into the waste container. |
| 2 Add Trypsin solution | Replace Sodium Chloride in culture chamber with the Trypsin solution. |
| 3 Trypsin incubation | Static 15 minute incubation in Trypsin solution. |
| 4 Rinse out Trypsin solution/Transfer in Pharmaceutically Acceptable Carrier | Add Isolyte with 0.5% HSA to displace the Trypsin solution into the waste container. |
| 5 Concentration/Volume reduction | Displace some of the Isolyte solution with air to reduce the final volume (concentration step) |

TABLE 8-continued

Wash-harvest Protocol

| Step Number & Name | Description |
| --- | --- |
| 6 Agitate Biochamber | Rocking motion to dislodge and suspend cells into Isolyte solution for collection |
| 7 Drain into Collection Container | Drain Cells in Isolyte solution into cell collection bag. |
| 8 Add rinse solution to Biochamber | Add more Isolyte to rinse out residual cells. |
| 9 Agitate Biochamber | Rocking motion to dislodge and suspend cells into Isolyte solution for collection |
| 10 Drain into Collection Container | Drain the final rinse into the cell collection bag. |

Compared to TRCs produced using a conventional method for post-culture wash (e.g. CYTOMATE®), TRCs produced using the wash-harvest process show higher and more consistent post-wash viability, higher post-storage viability, higher total viable cell number, higher total viable $CD90^+$ cell number, slightly lower residual BSA, and higher and more consistent CFU-F and CFU-GM per product. The post wash viability is more consistent with the new wash process with a standard deviation of 2% as compared to 10% for the CYTOMATE® wash process. TRCs produced using the wash-harvest also have a higher percentage of $CD90^+$ cells, meaning that there is a higher percentage of marrow stromal cells in the TRCs as well as $CD14^+$ cells, meaning there is a higher percentage of monocyte/macrophage cells in the TRCs. The presence of VEGFR1 was also increased in wash-harvest TRCs. Although the final viable total cell number is higher with the new wash process, the new wash product contains more non-dissociated aggregates of viable cells which should be distinguished from aggregates due to debris—a likely source of the large cell clumps occasionally seen in the CYTOMATE® wash product after 24 hours of storage. These non-dissociated aggregates do not appear to interfere with cell product storage or delivery.

Methods of Separation

The wash-harvest process described above is also useful for the separation of solutions with dissolved components from particles contained within the solution. The wash-harvest process according to the invention is based on the unexpected ability to generate a controlled flow of solution over particles settled on a horizontal surface such that the particles are not removed by the flow and effluent solution is collected free of particles.

The process uses, for example, a thin cylindrical chamber with its diameter oriented horizontally and with a height that is sufficiently small so that a solution introduced to an empty chamber will fill the height before flowing horizontally. The diameter of the chamber is sufficiently large to accommodate the quantity of particles to be separated and is typically many times the height of the chamber.

Typically, the chamber includes a height of about 0.4 cm to match the desired height for use of the chamber for culture of cells, but may be in the range of about 0.2 to about 1.0 cm (or more). The diameter of the chamber may be about 33 cm, but may also include a range of about 10 cm to about 50 cm (or more). Accordingly, a preferable chamber volume, according to some embodiments, may be about 280 cc, though such volume (of course) corresponds to the ranges of chamber diameter and heights.

Prior to the start of the separation process, the chamber volume is completely filled with a first solution containing particles. The particles are of higher density than the solution and are settled by gravity or adhered on the bottom circular surface of the chamber. The total stacked height of the particles in the chamber, which can be minimized by uniform distribution of the particles across the bottom surface, is a small fraction of the total height of the chamber. To perform the separation, a second solution of a desired new composition is introduced at the center of the chamber at a controlled flow rate and the solution flows symmetrically toward the perimeter of the chamber, displacing the first solution in the chamber which flows out of the chamber at the perimeter and is directed to a common collection point. As a result of the geometry, the linear velocity of the flow decreases in proportion to the distance from the center such that the linear velocity is slowest where it exits the perimeter of the chamber. The flow rate is preferably controlled so that the linear velocity is sufficiently low to prevent movement of settled particles out of the chamber, but only remove liquid therein. The relatively small height of the biochamber as described herein preferably allows for a plug-flow in the radial direction to minimize mixing of the displaced solution with the new solution. Accordingly, this allows a high percentage of the first solution to be displaced with a second solution from the biochamber. One or more additional volume exchanges with the second solution can be performed to further reduce residual levels of the first solution within the chamber.

As an alternative operating mode prior to removing the particles from the chamber, the first solution can also be displaced by a gas, such as air, that is introduced at the center of the chamber and within the same flow rate range as described for introduction of a second solution. This results in a controlled reduction of the volume of liquid within the chamber while still retaining the particles. A rinse solution of a smaller volume than the chamber can then be introduced as a carrier to remove and collect the particles from the chamber in a reduced solution volume.

A variety of solutions that are compatible with the contained particles can be used as the exchange liquid—e.g. for cells: any culture medium, any physiological buffer, any pharmaceutical grade injectable.

Any enzyme solution conventionally used in cell culture for detachment and harvest of adhered cells can be used. According to the method of the invention, culture media with contained adhered cells is replaced with a buffer containing the enzyme. The cells are exposed to the enzyme for a period of time so that the adherent cells are no longer adherent. The enzyme buffer is then replaced with another fluid that the cells will either be stored in or used in. The chamber is then agitated to cause the cells to be suspended in the fluid and the fluid is collected in a biocompatible container. For example, the fluid may be a cryo-protectant for storage at −80 deg. C. or a pharmaceutically acceptable carrier for patient administration, Enzyme solutions for cell harvest include trypsins (animal-derived, microbial-derived, or recombinant), various collagenases, alternative microbial-derived enzymes, dissociation agents, general proteases, or mixtures of these. A list of some commercial harvest enzyme solutions are listed below:

| Reagent | Manufacturer | Description |
| --- | --- | --- |
| Aastrom, Replicell ® Harvest Reagent | Invitrogen | Porcine derived trypsin |
| TrypLe ™ | Invitrogen | Recombinant enzyme derived from microbial fermentation |
| TrypZean ™ Solution | Sigma | Recombinant bovine trypsin expressed in corn |
| HyQTase ™ | HyClone | Proteolytic and collagenolytic enzymes |
| Accutase | Innovative Cell Technologies, Inc. | Proteolytic and collagenolytic enzymes |
| Accumax Solution | Innovative Cell Technologies, Inc. | Proteolytic and collagenolytic enzymes plus cell dispersal agents |
| Recombinant Trypsin/EDTA | Cascade Biologics | Recombinant bovine trypsin |

Bioreactor System

Some embodiments of the invention include methods and/or devices for creating post-culture cell compositions suitable for therapeutic use, and may be related to methods and devices/systems disclosed in U.S. Pat. Nos. 6,326,198 and 6,048,721.

For example, the bioreactor system as disclosed in U.S. Pat. No. 6,048,721 (the '721 patent) may be used to perform the methods according to some embodiments of the invention. A portion of this disclosure, describing a system for carrying embodiments of the present invention is set out below.

As shown in FIG. 1, a bioreactor system includes a disposable cell cassette 100 where the growth and expansion of cells takes places, a hardware incubator unit 200 and companion hardware, a system manager 300 that controls the biological and physical environment during the expansion process, and a processor unit 400 that facilitates at least one of the filling, processing and inoculation of cells, as well as the final harvest of cells at the completion of the expansion process.

Simulating bone marrow for the purpose of ex vivo growth and expansion of mammalian stem and hematopoietic progenitor cells generally requires, amongst other things, a uniform oxygen concentration and a uniform supply of a nutrient carrying perfusing liquid for all of the cells being cultured. A primary function of the cell cassette 100 is to provide a sterilely closed environment that supports oxygenation and medium perfusion of the contained biochamber Referring to FIG. 5, the primary element of the cell cassette is a disc-like bioreactor culture chamber 10 ("biochamber") having a preferably circular outer periphery. The biochamber may be formed of four main components: a top 20, a base 30, a cell bed disc 40 and a gas permeable, liquid impervious membrane 50.

Figure 7:
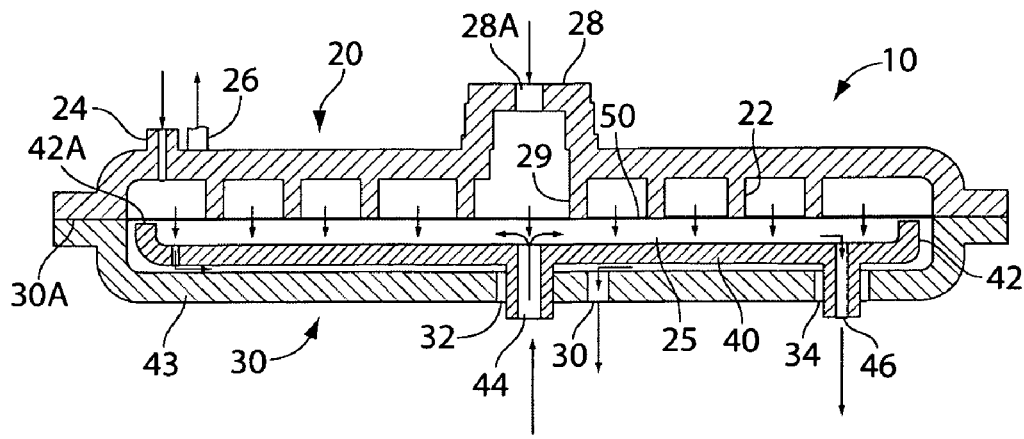
FIG. 7 is a schematic sectional view of the biochamber portion of a cell cassette according an embodiment of the invention;.

As shown schematically in FIG. 7, the top 20 of the biochamber is secured to the base 30 (preferably in a fluid tight manner), for example by applying localized energy to weld the two pieces together (or other fastening means such as a plurality of screws), at its radially outer periphery. The membrane 50 is clamped between the top and the base and is tightly stretched so as to separate the interior volume of the biochamber into upper and lower portions.

The cell bed disc 40 is located within the lower portion of the interior of the biochamber. It has generally a disc shape with an upwardly extending annular lip 42 at its outer radial periphery. Following inoculation of starting cells, cell growth occurs in a cell growth bed 25 defined between the upper surface of the disc 40, the lower surface of the membrane 50 and the annular lip 42. The upper surface A of the annular lip 42 is preferably coplanar with the upper surface of the flange 30 A of the base 30 when the disc 40 is fitted in the base, so that membrane 50 can cooperate with the lip 42 to seal the cell growth bed 25.

The disc 40 of the cell bed has a radially central growth media supply port 44, which extends downwardly through the base 30 to the exterior of the biochamber. Alternatively, the growth media supply port may be located at a radially central point above disc 40 of the cell bed and extend upwardly through the raised centerport 28 to the exterior of the biochamber (not shown). It also has at least one harvest port 46 (may also include a plurality of harvest ports) near the radially outer limit of the cell bed, i.e., just inside the lip 42. The port 46 also extends through the base to the exterior of the biochamber. Alternatively, the one or more harvest ports may be located near the radially outer limit of the base, i.e. just inside the perimeter of the cell bed and extend directly from the base to the exterior of the biochamber (not shown). Finally, a plurality of, e.g., 24, waste media discharge apertures 48 are located at the perimeter of the disc 40 to allow fluid communicaton between the cell bed compartment established above the disc and the waste compartment established below the disc. The apertures 48 are preferably equally spaced about the radially outer periphery of the disc 40, immediately adjacent to the lip 42.

A nutrient rich growth media is supplied to the media supply port 44. The growth media may be a standard growth medium, as is well known in the art, and may have a serum supplement such as fetal bovine serum, horse serum or human serum. It may also be serum free. Growth factors and reagents such as glutamine may also be added as necessary. The growth media may be supplied in premixed bags or may be modified on site.

From the media supply port, the growth media enters the cell bed 25 and flows radially outwardly toward the radial periphery of the disc 40. As it does so, it supplies nutrients to, and removes waste products from, the cells being cultured therein. It is discharged as waste media from the cell bed by flow through the plurality of apertures 48, as shown by arrows in FIG. 7.

Because of the radially outward flow of the perfusing liquid and the arrangement of the outlet apertures 48, the cells within the cell culture bed are uniformly perfused with nutrients. For example, the radial flow of the perfusing liquid to a plurality of equiangularly spaced outlet apertures promotes a uniform fluid flow from the inlet, and over the cell bed to the perimeter outlet locations on the circumference of the cell bed.

The base 30 has apertures 32 and 34 through which the ports 44 and 46 can extend in a fluid tight manner, for example, via seals (not shown) between the apertures and the ports. Alternatively, the apertures are not required if port 44 extends upwardly through the centerport 28 and port 46 extends directly from the base (not shown). The base also includes a generally centrally located outlet port 36 for the waste liquid displaced from the biochamber. The waste liquid from the apertures 48 flows radially inward, through the space between the bottom surface of the disc 40 and the top surface of the base 30, to the port 36 and is thereby discharged from the biochamber. The port 36 may be co-axial, but can also be slightly offset from the radial center of the base 30 in order to accommodate the aperture 32 for the media inlet port 44. Alternatively, the aperture is not required if port 44 extends upwardly through the centerport 28 (not shown).

The biochamber top 20 is secured to the base 30 in a fluid tight fashion, with the membrane 50 therebetween, as mentioned above. A concentric labyrinth path of ribs may be included which extend inwardly from the top 20 to support the membrane 50 against distortion due to the fluid pressure of the perfusion liquid in the cell bed. The ribs 22 maintain a precise spacing between the top surface of the disc 40 and the bottom surface of the membrane 50, i.e., a precise thickness for the cell growth bed. This thickness may be about 4 mm in order to assure adequate oxygenization of the cells within the cell growth bed. Alternatively, a series of periodic supports extending downwardly from the top 20 and a thin porous disc to which the membrane 40 is laminated may used to maintain the position of the membrane to provide a precise thickness for the cell growth bed (not shown).

The ribs 22 also form a labyrinth-like gas chamber through which an oxygenization fluid, such as air, can flow to supply oxygen which is diffused through the membrane and into the cell bed. The two ends of the labyrinth may be adjacent one another so that the oxygenizing air can be supplied to the gas inlet port 24 and discharged through the gas outlet port 26. Alternatively, if periodic supports have been used instead of the concentric labyrinth path of ribs, the gas inlet port and outlet port can be located near the perimeter of the top 180° opposite to each other so that oxygenizing air can be supplied to the gas inlet port and discharged through the gas outlet port (not shown).

A bell-like raised center port 28 is formed at a radial center of the top 20 and forms a chamber sealed by the annular rib 29 bearing against the membrane. Cells can be inoculated into the cell growth chamber via a center port septum 28A. For this, a non-latex needle septum may be secured to a port feature with an air-tight band for access directly to the cell residence area. Alternatively, a tubing line can extend from the center port that may be connected to an external container of cells using a sterile tube welder (not shown).

Figure 8A:
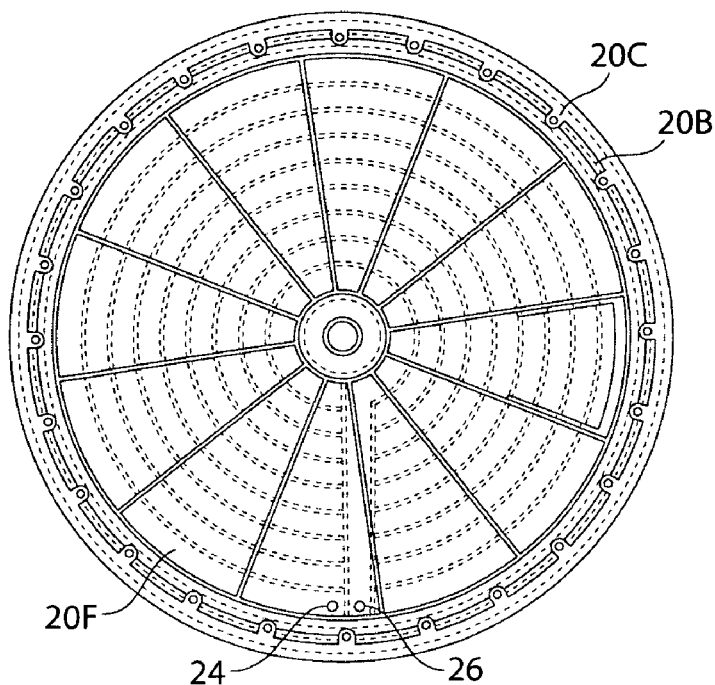
FIGS. 8A and 8B are top and sectional views of a biochamber cover according to an embodiment of the invention.
Figure 8B:
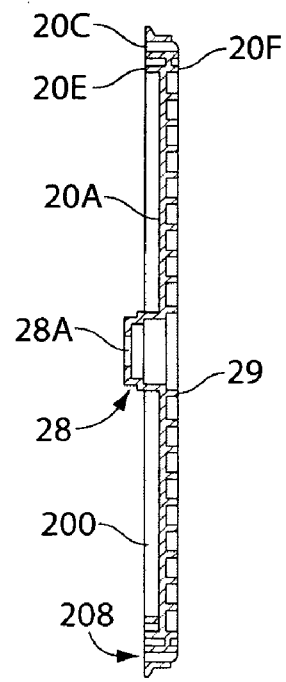

Referring to the detailed illustrations of the biochamber top, base and cell bed disc shown in FIGS. 8 through 10, the biochamber top 20 is shown in FIGS. 8A and 8B. The top 20 is preferably formed of an injection molded transparent, non-reactive plastic such as polystyrene or PETG. It has a generally disc-like main portion 20A bounded at its radially outer periphery by a flange 20B. The flange 20B has an equally spaced plurality of bolt holes 20C, through which may pass bolts (not shown) for securing the top 20 to the base 30. Alternatively, an EMA (Electro-magnetic) weld can be used for securing the top to the base (not shown).

The raised center port 28 has a generally bell shape and a central septum 28A. The septum is a gas and liquid impermeable barrier that may be pierced by an injection needle and is self-sealing when withdrawn. Alternatively, a tubing line can extend from the center port that may be connected to an external container using a sterile tube welder (not shown). An equally spaced plurality of radial reinforcing ribs 20D extend from the main portion 20A between the center port 28 and an annular reinforcing rib 20E adjacent the rim 20B.

The ribs 22 are generally annular in orientation and form a labyrinth 20F as shown by dash lines in FIG. 8A. The labyrinth may be convoluted such that an oxygenizing gas is able to flow through a gas chamber defined thereby over the entire cell growth bed. The opposite ends of the labyrinth are preferably adjacent one another at the radially outer end of the main portion 20A. An inlet port 24 and the outlet port 26 communicate with the opposite ends of the labyrinth. Alternatively, if periodic supports have been used instead of the concentric labyrinth path of ribs, the gas inlet port and outlet port can be located near the perimeter of the top 180° opposite to each other so that oxygenizing air can be supplied to the gas inlet port and discharged through the gas outlet port (not shown).

A radially innermost rib 29 may be a continuous annulus which, in cooperation with the membrane 50, seals the gas chamber defined by the labyrinth from the interior of the central port 28. A radially outermost continuous rib 20F defines the outermost limit of the labyrinth. The tips of all of the ribs 20F, 22 and 29 are coplanar with the bottom surface of the flange 20B so that the ribs seal with respect to the membrane 50 when the biochamber is assembled. Alternatively, if periodic supports have been used instead of the concentric labyrinth path of ribs, the tips of all the supports are coplanar with the bottom surface of the flange 20B so that the position of the membrane 50 is controlled (not shown).

Referring to FIGS. 9A and 9B, the cell bed disc 40 is preferably also formed of an injection molded transparent, non-reactive plastic such as polystyrene or PETG. It has a generally disc-like main portion 40A bounded at its radially outer periphery by the annular lip 42. The upper surface of the main portion is generally smooth and unobstructed and forms a surface of adhesion for the cell colony being cultured.

Referring to FIGS. 10A and 10B, the base 30 is preferably also formed of an injection molded transparent, non-reactive plastic such as polystyrene or PETG. It also has a disk-like main portion 30A bounded by a raised peripheral flange 30A having an upper surface 30B and bolt holes 30C. Alternatively, the bolt holes are replaced with features to perform an EMA weld to secure the base to the top (not shown). When assembled, the disc 40 fits entirely within the bounds of the peripheral flange 30A with the surface A closely adjacent, and coplanar with, the surface 30B. A peripheral lip 30D extends upward from the radially outer edge of the flange 30B to position and retain the membrane 50 during assembly of the biochamber.

The upper surface of the main portion 30A has a plurality of raised regions 30E which support the bottom surface of the disc 40 and maintain a separation between disc 40 and base 30, thereby defining the fluid path for the return flow of the waste media to the central outlet port 34. Recesses 30F and 30G surround each of the apertures 32 and 34, and can house resilient elements for sealing the apertures. Alternatively, the apertures are not required if port 44 extends upwardly through the centerport 28 and port 46 extends directly from the base (not shown).

A plurality of radial supporting ribs 30H extend from the bottom surface of the base and extend between the annular supporting ribs 30I and 30J. Annular reinforcing enlargements 30K, 30L and 30M surround the apertures 32, 34 and 36, respectively.

In assembling the biochamber, appropriate seals are positioned at the apertures 32 and 34, and the disc 40 is positioned within the base 30 with the nipples of the ports 44 and 46 sealingly extending through the respective apertures as shown schematically in FIG. 7. Alternatively, the apertures and related seals are not required if port 44 extends upwardly through the centerport 28 and port 46 extends directly from the base (not shown). The membrane 50 is then placed over the disc 40 and the flange 30A, and is held within the lip 30D. Alternatively, the membrane 50 is laminated to a porous disc to provide additional mechanical stability prior to placement over the disc 40 (not shown). The top 20 is then placed over the base with the bolt holes 20C and 30C in alignment, and bolts are passed through the bolt holes and tightened to unify the biochamber. Alternatively, an EMA weld is used to join the top to the base (not shown). At this time, the outer annular rib 20F will clamp the membrane 50 against the radially innermost portion of the surface 30B to seal the interior of the biochamber.

Figure 5:
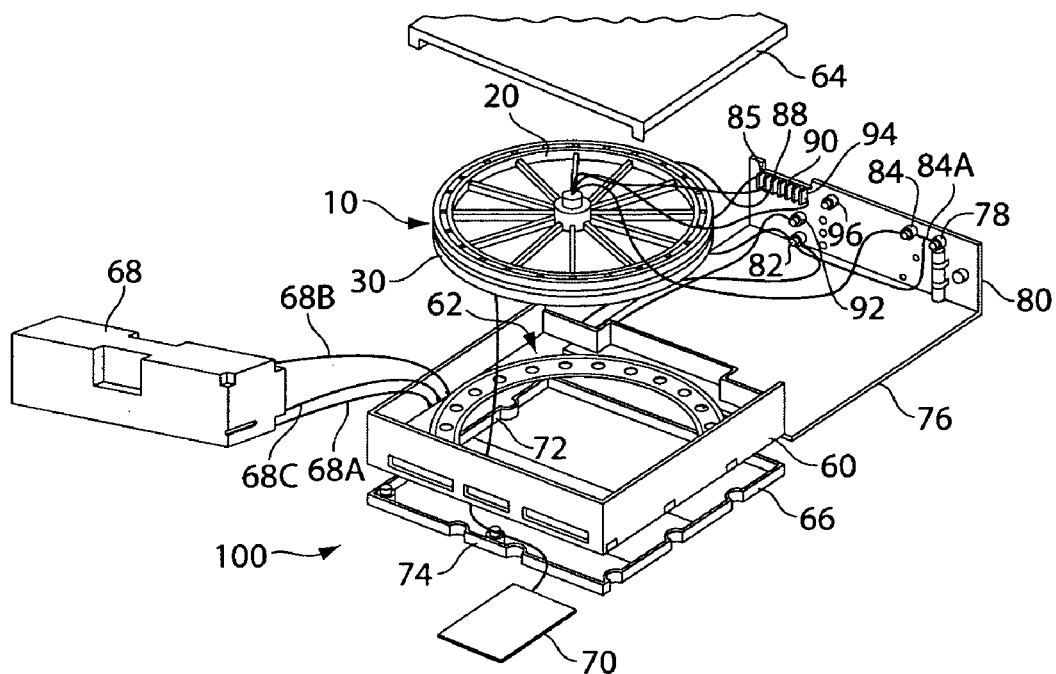
FIG. 5 is an exploded view of the cell cassette of FIGS. 4A and 4B.
Figure 6:
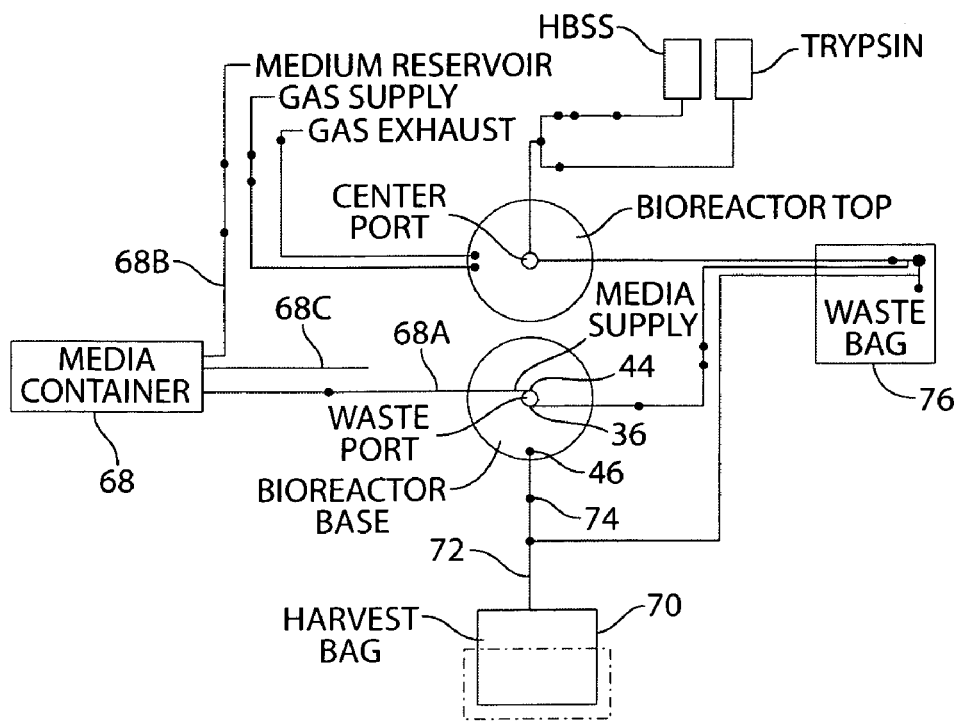
FIG. 6 is a schematic view showing fluid conduit routing in the cell cassette according to an embodiment of the invention.

Referring to the schematic FIGS. 5 and 6, the biochamber 10 is held within a casing of a cell cassette 100 and forms a preassembled, disposable unit. The biochamber is secured to a cassette base 60 of the cassette casing. In the illustrated system, the base 60 has a support flange 62 with a central aperture having a plurality of holes. The bolts used to secure the top to the base of the biochamber 10 can also extend through these holes for securement of the biochamber to the cassette base 60. Alternatively, mounting clips can be mounted to the base for the securement of the biochamber to the base at 3 or more equally space perimeter positions (not shown). The cassette base is closed from above by a top 64 and from below by a tray 66, and a media supply container 68 is mounted to a front surface of the cassette base 60 for supplying a growth media to the biochamber. The media supply container 68 is provided with a media supply line 68A connected to the media inlet port 44 of the biochamber. Pressurized air from an air pump is supplied to the air space above the media in the media supply container via the line 68B, and in this way the growth media is pressurized so as to provide a constant flow rate of media to the cell growth bed 25 in the biochamber. Additional growth media is supplied to the container via the media container supply conduit 68C.

A cell harvest bag 70 (or other cell harvest collection device) may be connected to the harvest port 46 of the biochamber via the conduit 72 and the harvest valve 74.

A waste liquid bag 76 is positioned below the biochamber and rests on the tray 66 of the cell cassette. It receives waste liquid from the biochamber via a drip chamber device 78 attached to a valve plate 80 at the rear of the cell cassette. The drip chamber includes a siphon break to permit a precisely controlled low pressure within the biochamber. A drip counter (not shown) can be associated with the drip chamber device. It counts the drops of waste liquid to detect the flow rate.

The waste liquid reaches the drip chamber device via a waste valve 82. Gas pressure at the center port 28 of the biochamber is used to regulate flow through the drip chamber, via the center port valve 84 and the line 84A.

Also attached to the valve plate may be an air pump supply port 86 for supplying compressed air at a constant pressure to the media supply container via the air pump supply line 68B; gas in and out ports 88 and 90 for supplying fresh oxygenizing gas to, and discharging spent oxygenizing gas from, the biochamber; a media supply valve 92 connected to the media container delivery line 68A; HBSS valve 94; and trypsin valve 96. Alternatively, valve 94 and valve 96 are replaced with a single valve for addition of a range of reagents, such as HBSS and trypsin (not shown).

Each cassette may also include a "key" containing a nonvolatile memory device and a clock. Before use, the key of the cassette is initialized with tracking data, protocol commands and real time via the system manager 300. The key is used by the system electronics during the cell production process to record pertinent data as well as to access the protocol commands.

In use, a sterile, single use disposable cell cassette 100 is supplied in a protective package. It includes the medium supply reservoir 68, medium flow control (not shown), the biochamber 10, the waste reservoir 76, the harvest reservoir 70, a key and the necessary plumbing, valving and packaging to interconnect and support the components. Alternatively, the harvest reservoir can be provided as a separate component and then connected to the cassette at the time of harvest using a sterile tube welder.

In operation, the key is first initialized by the system manager. Once the key has been initialized, it is transferred to the processor 400. The processor includes a multiaxis gyrator ("wobbulator") 410. The wobbulator includes a support table 412 onto which the cassette can be secured. The wobbulator has mechanical linkages 414 for pivoting the support table 412 about two orthogonal horizontal axes.

When a cell cassette is loaded in the processor 400 and clamped onto the support table 410, and the key indicates that inoculation is required, the processor provides an automatic sequence of inoculation operations. For example, the inoculation sequence can consist of the following steps. First, the wobbulator table 412 is brought to a horizontal home position. The cell cassette 100 is then primed with growth media to the required volume, employing gravity feed of media from the reservoir 68. Alternatively, pressure can be applied to the reservoir to facilitate transfer of media. During this time, the harvest valve 74 is closed and the waste valve 82 is open so that media in the biochamber 25 can flow through the apertures 48 but not through the harvest port 46. The cell cassette is then tilted to generate a bubble to be used in distributing the cells. The biochamber is then inoculated with cells. This may be done via a hypodermic syringe passing through the center port septum and the membrane. Alternatively, a container with cells can be connected to a tubing line extending from the centerport. using a sterile tube welder and then cells inoculated using gravity or pressure (not shown). The wobbulator then oscillates the cell cassette (i.e., agitates the contents therein) according to a predetermined program to distribute the cells on the upper surface of the disc 40. At this time, the bubble aids in the even distribution of the cells within the biochamber. Remaining air is then purged through the center port and the cassette is removed from the processor. The cassette is then ready for incubation.

The biochamber 10 may be substantially filled (preferably completely filled) with the growth media, which may be displaced by cells during inoculation. For example, the biochamber may be filled to around 80% total volume with the growth media. The cells, during inoculation, may be suspended in the same growth media, or a different liquid/media. During inoculation, the biochamber may be less than completely filled (e.g., 90% total volume), so that cells may be distributed evenly throughout the interior of the biochamber during agitation. After inoculation, preferably, the biochamber is substantially filled (preferably completely filled).

The cassette is then placed in the incubator 200 where the biochamber is maintained in a horizontal position to allow cells to settle by gravity onto the bottom surface of the biochamber where they remain throughout culture. The incubator is an instrument capable of accepting cell cassettes for cell production. It can take the form of a rack 210 to which plural cassettes are attached. It mates with the cassette to provide control over the culture environment within the cassette. It is also connected to the system manager 300 and to the key for storing the incubation start time and date on the key, and incubation data is continually provided to the key during the incubation sequence. The key also receives information on abnormal events, such as alarms or power failures, the amount of medium used and the incubator identification. The incubator controls the flow of medium through the growth chamber, the temperature of the growth medium reservoir 68, and the concentration and flow rate of gases delivered to the gas chamber in the biochamber, based on control settings stored in the key. The incubator also monitors various safety/alarm parameters to assure that the cell production process is proceeding as expected. This can be done for a number of incubators through the system manager computer or by use of an independent incubator computer.

Following the completion of culture, the cassette is removed from the incubator and placed back into the processor where the harvest wash process previously described is performed.

The invention will be further illustrated in the following non-limiting examples.

EXAMPLES

Example 1

Tissue Repair Cell (TRC) Culture and Wash Technique Protocols

TRC Culture

Fresh bone marrow mononuclear cells (BM MNC) that were isolated by FICOLL® from the blood of normal donors were purchased from Poietics Inc. (Gaithersburg, Md.). Alternatively aspirated bone marrow (BM) was received as a clinical specimen from patients and separated on FICOLL® to create a mononuclear cell prep. Cell concentration was assessed using an automated cell counter, and BM MNC were cultured by the method of Lundell, et al., described above. Prior to inoculation, culture chambers were primed with culture medium consisting of IMDM, 10% fetal bovine serum, 10% horse serum, 5 µM hydrocortisone, and 4 mM L-glutamine. Medium was passed through the culture chambers at a controlled, ramped perfusion schedule during the 12 day culture process. The cultures were maintained at 37° C. with 5% $CO_2$ and 20% $O_2$.

CYTOMATE® Wash Method

CYTOMATE® is a fully automated system designed for washing and concentrating white blood cell products. It includes an electromechanical instrument and single-use pre-sterilized disposable sets that provide a wash circuit for each batch of cells to be processed. It incorporates spinning membrane technology that provides a tangential flow affect to prevent excessive filter loading with cells.

Setup
1. Load wash circuit set onto CYTOMATE® instrument
2. Connect bags:
   Bag of cells harvested from culture process (TRCs in 800 to 1000 mL volume of culture process fluids, e.g. culture medium, harvest enzyme solution).
   Buffer solution (2000 to 3000 mL, Isolyte supplemented with 0.5% HSA).
   Collection bag for washed cells (120 mL to 180 mL collect volume).
   Supernatant bag (2600 to 3900 mL waste liquid not collected with cells).

CYTOMATE® Procedure:
1) Prime wash circuit with buffer solution and initiate recirculation
2) Transfer cells from harvest bag into wash circuit, reduce liquid volume by recirculating cells through wash circuit while removing liquid through filter in wash circuit (filter is spinning to provide tangential flow affect and prevent filter clogging). Removed liquid is collected in supernatant bag.
3) Use buffer to rinse residual cells from harvest bag into wash circuit.
4) Wash cells by recirculating cells through wash circuit, simultaneously removing liquid through the spinning filter into supernatant bag and adding buffer solution as required to maintain volume.
5) Transfer washed cells into collection bag.
6) Use buffer to rinse residual cells from wash circuit into collection bag.

Wash Harvest Method

The wash-harvest process begins by displacing culture media from a culture chamber with a biocompatible rinse solution (Step 1, Table 8, above). The rinse solution (normal saline or other isotonic solution) is then replaced with a cell harvest enzyme solution (Step 2, Table 8), with porcine trypsin being used the majority of the time. Other non-animal derived harvest reagents such as TRYPLE™ (Invitrogen, Carlsbad, Calif.) and TRYPZEAN™ (Sigma, St. Loius, Mo.) have also been used successfully. The culture chamber is left to incubate for a period of time (5-60 minutes, preferably 15 minutes with porcine trypsin) as the enzyme works to dissociate the cells from each other and from the culture surface (Step 3, Table 8). When the enzyme incubation is complete, a second, typically injectable grade, rinse solution (Isolyte or Normasol) displaces the enzyme solution (Step 4, Table 8). At this point the chamber contains the detached cells, which remain settled on the cell surface, and is suspended in an injectable-grade solution. In order to increase the final harvested cell concentration and reduce the final volume, a portion of this rinse solution is displaced with air (Step 5, Table 8). When the final liquid volume (100-350 ml) is achieved in the culture chamber, the chamber is agitated in order to bring the settled cells into solution (Step 6, Table 8). This cell suspension is drained into a cell collection container (Step 7, Table 8). An additional amount of the injectable-grade solution may be added to the cell culture chamber and a second agitation could occur in order to rinse out residual cells if necessary (Steps 8 & 9, Table 8). This final rinse is then added to the cell collection container (Step 10, Table 8).

Comparrision of Cytomate vs Wash Harvest

On the day of harvest the TRCs were split into two cultures. The first culture was harvested and concentrated per the standard CYTOMATE® process. The TRCs in the first culture were harvested by trypsinization (0.025% trypsin in 0.9% sodium chloride), and washed to deplete culture materials using a CYTOMATE® (Baxter International, Inc.) cell processor per manufacturer's instructions. The cell product was washed with a pharmaceutical grade electrolyte solution supplemented with 0.5% HSA into a 150 mL volume and used, as is, or concentrated to 15 ml or 5 mL volumes in a biocompatible bag. The second culture of TRCs was harvested using a draft of the combined wash-harvest ARS Processor Sequence, and a modified concentration process designed to further reduce residuals with an additional dilution step.

To create a concentrated TRC suspension, the collected cells from each wash were centrifuged to a 20 ml volume and transferred to a smaller bag such as a Cryocyte bag. Once in the final container a second centrifugation step is performed to concentrate to a final volume between 4.7 and 20 mls, creating a dose of cells ranging from 35-300 million cells in 6 ml±1.3 ml, but up to 20 ml of injectable grade solution depending on the final application.

Example 2

The Wash Harvest Increased TRC Quality over the CYTOMATE® Wash

TRCs isolated using the Wash Harvest had greater cell viability, greater cell yield, less residual BSA, higher total numbers of progenitor cell, stem cell, immune cell and endothelial cell markers, increased ability to form colonies, comparable viability after needle passage, higher levels of anti-inflammatory cytokines and higher levels of indoleamine 2,3-dioxygenase (IDO). These improvements in the TRC population due to use of the novel Wash Harvest process allows the population to be used as a more effective tissue repair therapeutic agent when compared to current state of the art processes.

Materials and Methods

Cell Count/Viability

Cell count and viability were measured by Nucleocounter or trypan blue exclusion. The manufacturer's protocol was used for cell counting using the Nucleocounter. Briefly, the cell suspension was diluted to between 100,000 and 10,000,000 cells/ml, and a nucleocassette aspirates the cell suspension. The nucleocassette is placed into the Nucleocounter for automated propidium iodide staining, including cell count and viability. Where Nucleocounter data was not available, trypan blue exclusion and hemocytometer (manual counting) was used to enumerate cell number and viability. Over the course of 27 sample analyses, the Nucleocounter cell counts were within 13% of the Trypan Blue counts and viability was within 4%.

During these experiments the product sampling at the post-culture processing phases varied depending on the assays and other uses for the cells. The following strategy was used in order to get the most accurate total viable cell numbers from the data. The total cell number of each sample taken was calculated, and then that number was multiplied by the viability of the next processing step and then added to the viable cell count at that step. For example, if a sample of $10 \times 10^6$ total cells was removed from the washed product and the viability of the cells after concentration was 80%, then $8 \times 10^6$ viable cells were added to the total viable count of the concentrated product, to represent what would have been there had the non-standard sampling not occurred. Once the non-sampled totals were calculated, the true manufacturing sample volume of 29 mL was subtracted from each washed product total cell number.

Residual Levels

Supernatant from the final TRC concentration process for each experiment was used to measure the level of residual BSA (via ELISA) and Tryptic activity (via the Quanticleave assay). A BSA ELISA assay was used to measure and compare the levels of residual BSA from the culture medium.

Concentration Protocol

To create a concentrated suspension, the collected cells are centrifuged to a 20 ml volume and transferred to a smaller bag such as a Cryocyte bag. Once in the final container a second centrifugation step is performed to concentrate to a final volume between 4.7 and 20 mls, creating a dose of cells ranging from 35-300 million cells in 6 ml +/− 1.3 ml, but up to 20 ml of injectable grade solution depending on the final application. Preferred volumes for the concentrated cultures are 6 ml±1.3 ml. When TRCs are retrieved from storage, cultures were thawed in a 37° C. circulating water bath.

Cell, viability and % CD90+

Cell viability and % CD90+ cells were measured by flow cytometry. Cells were washed and resuspended in 1× Dulbecco's phosphate buffered saline (PBS; Gibco) containing 1% bovine serum albumin. Tubes containing $10^6$ cells in 0.5 ml were stained on ice with various combinations of fluorescently-conjugated monoclonal antibodies. Viability was determined by 7-Amino-Actinomycin D (7AAD) (Beckman Coulter). 7AAD only enters membrane-compromised cells and binds to DNA. Cells were stained with PC5-conjugated anti-CD90 (Thy1) antibodies and FITC-conjugated anti-CD14 (Beckman Coulter). After 15 minutes, cells were washed and resuspended in 0.5 ml PBS/BSA for analysis on the Epics XL-MCL (Beckman Coulter) flow cytometer.

Intracellular Cytokine Analysis by Flow Cytometry

Cytokine expression by TRCs produced using the Wash Harvest process was determined quantitatively by 2-color intracellular flow cytometric analysis. Briefly, TRCs were incubated overnight with or without bacterial lipopolysaccharide (LPS) in the presence of brefeldin A to enhance intracellular cytokine accumulation in the Golgi apparatus while blocking cytokine secretion. The TRCs were stained for cell surface markers by incubation with FITC or Cy5PE -conjugated monoclonal antibodies (mAbs) (anti-CD14, CD66b, CD90 or control mAbs). The lymphocyte subpopulation was defined by gating on cell size based on forward (FSC) and granularity based on side (90°) light scatter (SSC). Subsequently, the cells were fixed using paraformaldehyde and permeabilized in saponin prior to staining with cytokine-specific PE-conjugated monoclonal antibodies (IL-6, IL-10, IL-12 or irrelevant control) as indicated in the left column of Table 4. Data for 2-color analysis was acquired on a Becton Dickinson FC500 flow cytometer.

CFU Frequency Analysis

For colony forming unit-fibroblast (CFU-F) assays, cells were plated in 1 ml LTBMC in 35 mm tissue culture treated dishes. For TRCs, 500 and 1,000 cells were plated per dish. Cultures were maintained for 8 days at 37° C. in a fully humidified atmosphere of 5% $CO_2$ in air. CFU-F colonies were then stained with Wright-Giemsa and colonies with greater than 20 cells were counted as CFU-F.

For colony forming unit-granulocyte/macrophage (CFU-GM) assays, cells were inoculated in colony assay medium containing 0.9% methylcellulose (Sigma), 30% FBS, 1% BSA, 100 µM 2-mercaptoethanol (Sigma), 2 mM L-glutamine (Gibco), 5 ng/ml PIXY321, 5 ng/ml G-CSF (Amgen), and 10 U/ml Epo. TRCs were plated at 1,500 and 3,000 cells per ml. Cultures were maintained for 14 days and were colonies greater than 50 cells were counted as CFU-GM.

Cell Delivery Through Needles

To test the effects of needle delivery on TRC cell counts and viability, samples was run from five of the Wash Harvest products and three of the CYTOMATE® wash products. These delivery experiments tested the ability of stored cells to be delivered to patients without loss of viability or concentration after passing through 25 gauge needles.

After 24 hours storage at 4° C., cryocyte bags containing TRCs were removed from refrigerator and massaged to resuspend and homogenize the TRCs for sampling. Two 0.5 mL samples were collected via 3 mL syringe and placed into tubes labeled as "TRC." Afterwards, two additional 3 mL syringes were placed onto the 3 way-stopcock valve and an additional 0.5 mL per syringe was taken. Twenty-five gauge needles (1½ inch, BD) were then screwed onto these additional 2 syringes (3 mL) and designated as "TRC, 25 gauge, ½ inch needle." Afterwards, the remaining TRC samples were measured and volume recorded. Onto these 3 mL syringes, 25 gauge needles (1½ inch) were added to two syringes and 25 gauge needles (3 inch, spinal needle) added to other two syringes. The entire 0.5 ml needle samples within the 3 mL syringes with needles were dispensed using a syringe pump (Harvard Apparatus, Holliston Mass.) at a rate of 2.5 mL per minute or 0.5 mL in 12 seconds into polystyrene round bottom tubes. After cell delivery through needles, all samples were evaluated for cell counts using nucleocounter.

Western Analysis of IDO Expression

TRCs express an inducible immunoregulatory enzyme designated indoleamine 2,3 dioxygenase (IDO) which is associated with down-regulation of inflammatory responses. Tissue Repair Cells (TRCs) were derived using the new wash-harvest process as described in the current invention. After harvest, TRCs were incubated for 24 hours in medium alone or medium containing 1000 units/ml recombinant human interferon-$\gamma$ (IFN-$\gamma$). Protein extracts from total cell lysates were separated on a 10% SDS polyacrylamide gel, transferred to a polyvinylidene difluoride (PVDF) membrane and probed using a mouse anti-human IDO-specific monoclonal antibody. A goat anti-mouse horse-radish peroxidase conjugated second-step antibody was used for subsequent visualization by chemiluminescence. This experiment demonstrates a characteristic 44 kilodalton (kd) band corresponding specifically to expression of IDO protein by TRCs after induction with IFN-$\gamma$.

Results

Total Viable Cell Count

Figure 11:
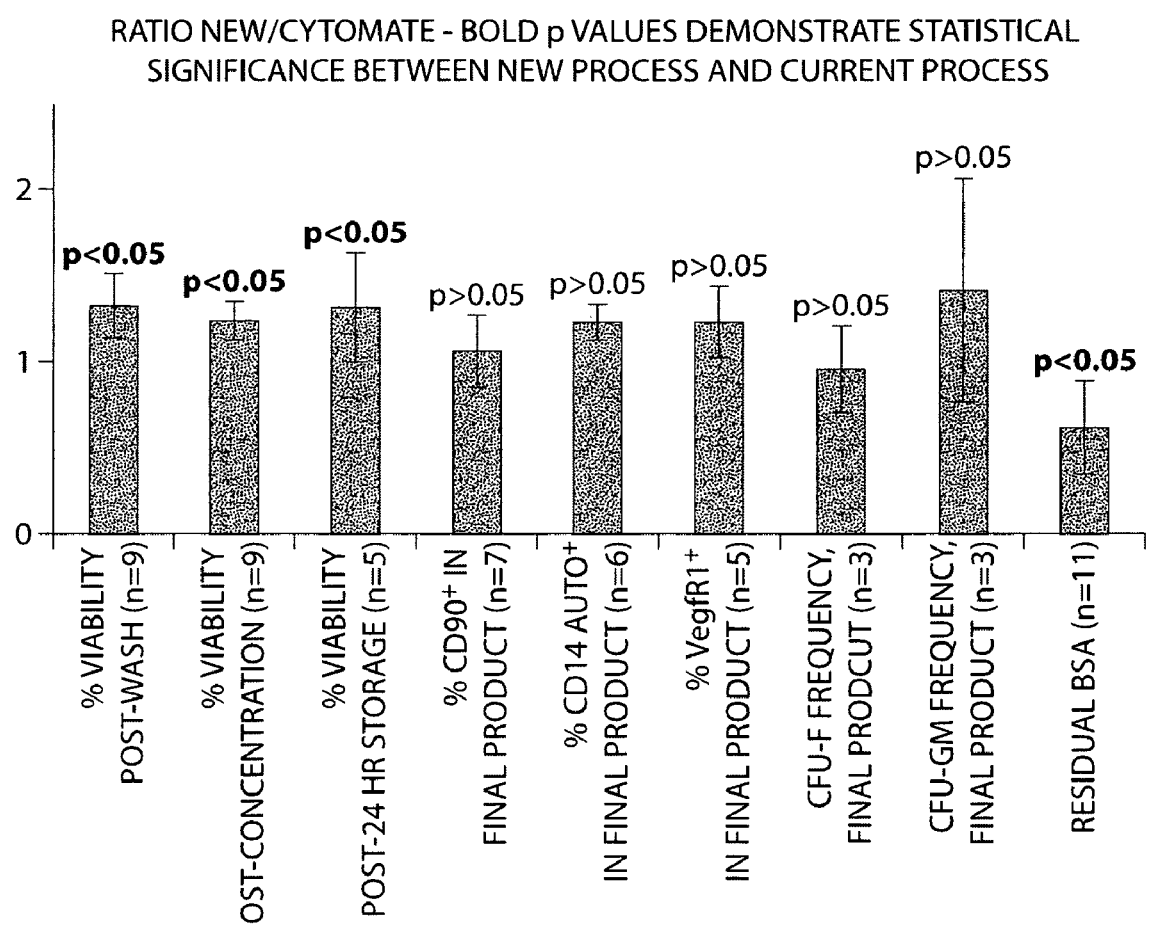
FIG. 11 is a bar graph showing the ratio of Wash-Harvest/CYTOMATE® wash results for % cell viability post-wash, post-concentration, and post-storage; % CD90, % CD14auto+, % VegfR1+, CFU-F and CFU-GM frequency, and residual bovine serum albumin (BSA).

FIG. 11 shows that the Wash Harvest repeatedly produced higher numbers of total viable cells post-wash than when the CYTOMATE® wash was used, after the manufacturing sample of 29 mL was subtracted. The data summarized in FIG. 11 was from 9 productions that compared the CYTOMATE® wash to the hybridization wash from the same donor. Aastrom Harvest Reagent (porcine trypsin) was used in all nine of these productions. The average post-wash total viable cell yield for the CYTOMATE® wash was $66.5 \times 10^6 \pm 36.8 \times 10^6$ viable cells while the average post-wash total viable cell yield for the hybridization wash was $144 \times 10^6 \pm 50.9 \times 10^6$ viable cells. Variability in total yield appears to be donor-dependent.

Viability

FIG. 11 also shows that the Wash Harvest repeatedly produced higher cell viability post-wash than when the CYTOMATE® wash was used. The percent viability was performed on cells isolated from the same 9 donors as described above. The wash-harvest product shows a more consistent viability with a standard deviation of 2%, compared with the CYTOMATE® wash viability standard deviation of 10%.

Count and Viability After 24 Hour Storage

FIG. 11 also shows that the Wash Harvest repeatedly produced higher cell viability, even after 24 hours of storage at 4° C., than when the CYTOMATE® wash was used. The percent viability after 24 hours of 4° C. storage was measured from cells from 5 donors.

BSA Concentration Post-Wash

FIG. 11 also shows that the Wash Harvest produced lower concentrations of the residual BSA left over from the culturing of the TRCs than when the CYTOMATE® wash was used. Low BSA levels are necessary in order to generate a pharmaceutical product appropriate for administration to humans.

Cell, Viability and % CD90$^+$ Via Flow

FIG. 11 shows that the Wash Harvest repeatedly produced higher percentages of CD90$^+$ TRCs than when the CYTOMATE® wash was used in unconcentrated cells. CD90$^+$ cells represent bone marrow stromal cells which have stem/progenitor cell properties and are useful for repairing various tissue types.

Figure 12:
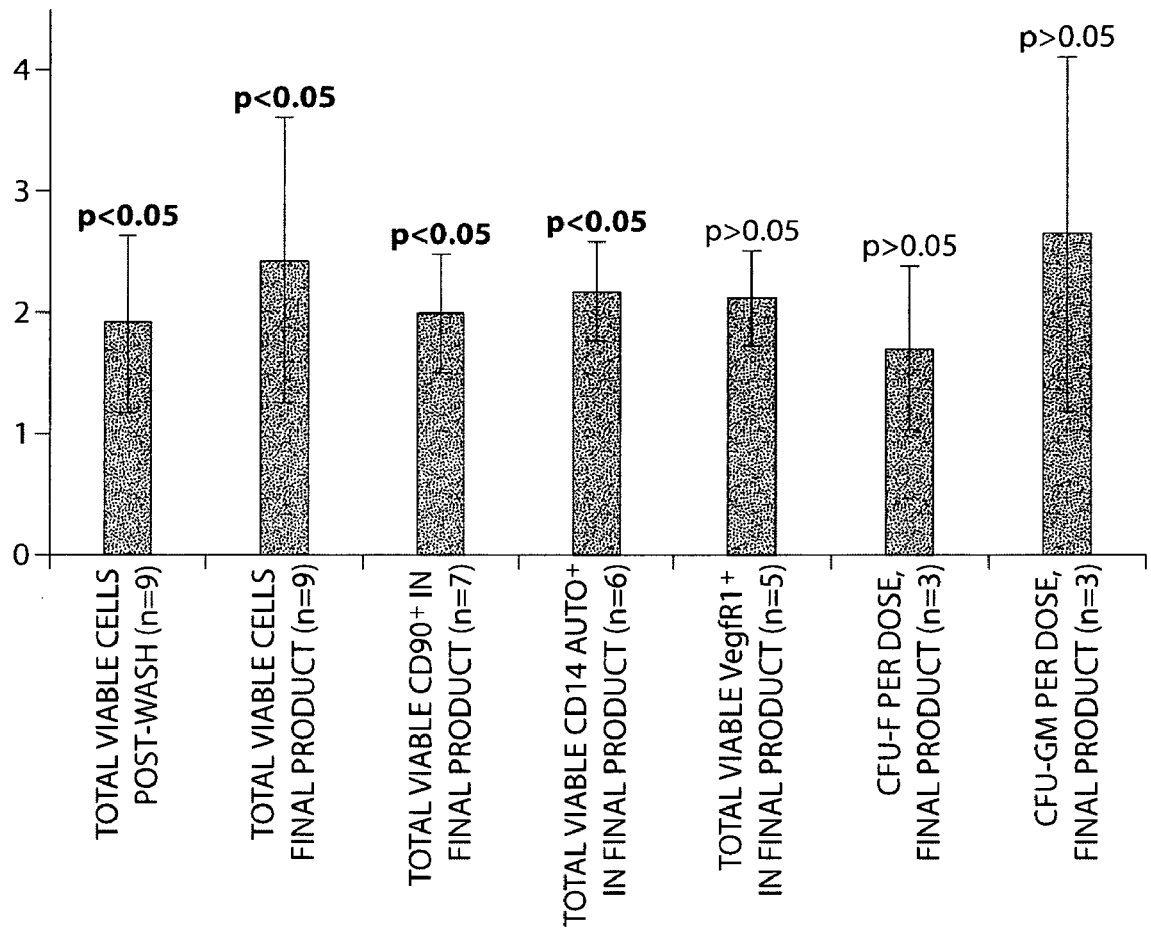
FIG. 12 is a bar graph showing the ratio of Wash-Harvest/CYTOMATE® wash results for total viable cells post wash, total viable cells final product, total viable CD90$^+$ cells, total viable CD14$^+$ auto$^+$ cells, total viable VEGFR1$^+$ cells, total CFU-Fs, and total CFU-GMs.

FIG. 12 shows that the Wash Harvest repeatedly produced higher total numbers of viable CD90$^+$ TRCs than when the CYTOMATE® wash was used. The average total viable CD90$^+$ cells in the wash-harvest final product was $42.4 \times 10^6 \pm 16.5 \times 10^6$. The average total viable CD90$^+$ cells in the CYTOMATE® wash final product was $19.1 \times 10^6 \pm 10.8 \times 10^6$.

CD14$^+$ Auto$^+$ %

Figure 13:
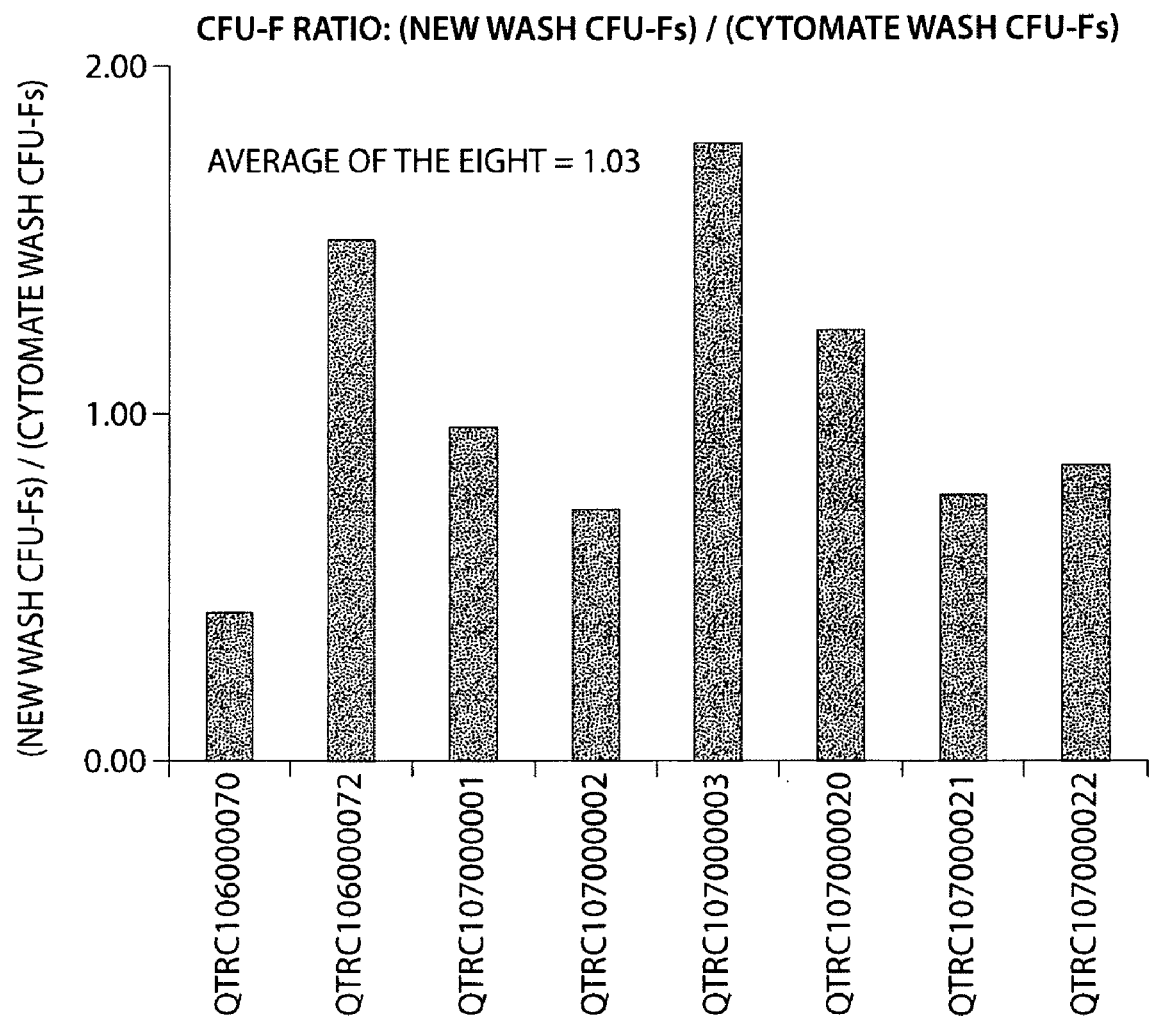
FIG. 13 is a bar graph showing the ratio of CFU-F frequency, (Wash-harvest)/(CYTOMATE® wash).

FIGS. 12 and 13 shows that the Wash Harvest repeatedly produced higher percentages and total numbers of viable CD14$^+$ Auto$^+$ TRCs than when the CYTOMATE® wash was used. The average total viable CD14$^+$ Auto$^+$ cells in the new wash concentrated product over these six donors is $34.8 \times 10^6 \pm 9.08 \times 10^6$. The average total viable CD14$^+$ Auto$^+$ cells in the CYTOMATE® wash concentrated product over these six donors is $16.5 \times 10^6 \pm 5.37 \times 10^6$.

VEGFR1$^+$ %

FIGS. 12 and 13 shows that the Wash Harvest repeatedly produced higher total numbers and percentages of VEGFR1$^+$ TRCs than when the CYTOMATE® wash was used in concentrated cells, demonstrating that more endothelial cells are in the final mixture. In each of the five experiments where this was measured, more viable VEGF-R1$^+$ cells were seen in the Wash Harvest product compared to the CYTOMATE® control. The average total viable VEGF R1$^+$ cells in the CYTOMATE® wash concentrated product over these five donors is $16.5 \times 10^6 \pm 5.37 \times 10^6$.

CFU-F Frequency

Figure 14:
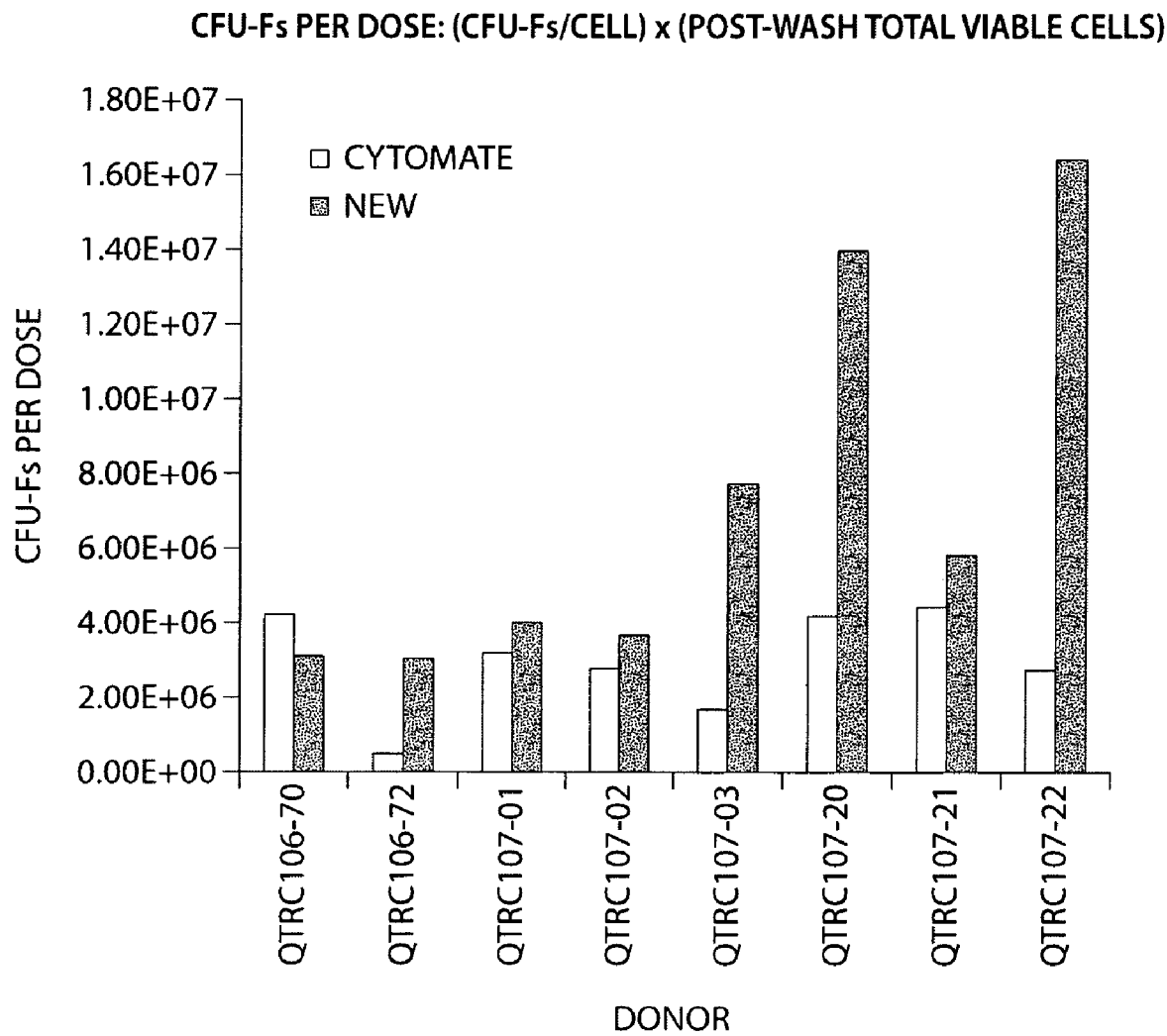
FIG. 14 is a bar graph showing CFU-Fs per dose of TRCs. Total post-wash viability cell count measured by Nucleocounter, was used to calculate CFU-Fs/dose, except where not available and trypan blue data was used (samples 106-70 and 106-72). For each pair of bars for each sample, the left bar shows results using the CYTOMATE® wash and the right bar shows results using the wash-harvest.

FIGS. 12 and 14 shows that the Wash Harvest process produced comparable CFU-F frequencies compared to the CYTOMATE® wash. The average of the CFU-F frequency ratio was 1.03.

Figure 15:
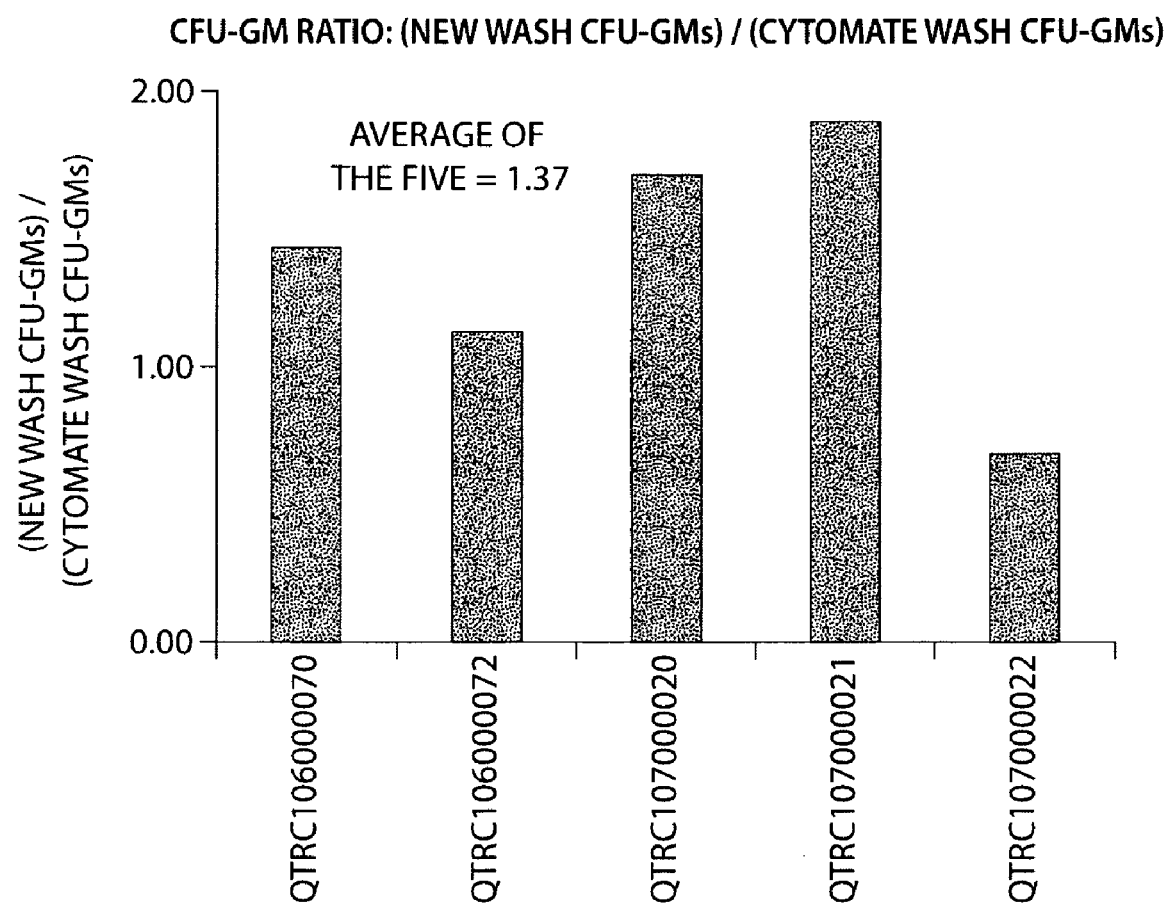
FIG. 15 is a bar graph showing the ratio of CFU-GM frequency, (Wash-harvest)/(CYTOMATE® wash).

FIGS. 13 and 15 shows that the Wash Harvest produced greater numbers of CFU-F per dose than the CYTOMATE® wash. The total CFU-Fs per dose was calculated by multiplying the frequency of CFU-Fs per cell by the post-wash total viable cell count. The average CFU-Fs per dose for the new wash process across these 8 experiments is $7.26 \times 10^6 \pm 5.22 \times 10^6$. The average CFU-Fs per dose for the CYTOMATE® wash process across these 8 experiments is $3.01 \times 10^6 \pm 1.37 \times 10^6$.

CFU-GM Frequency

Figure 16:
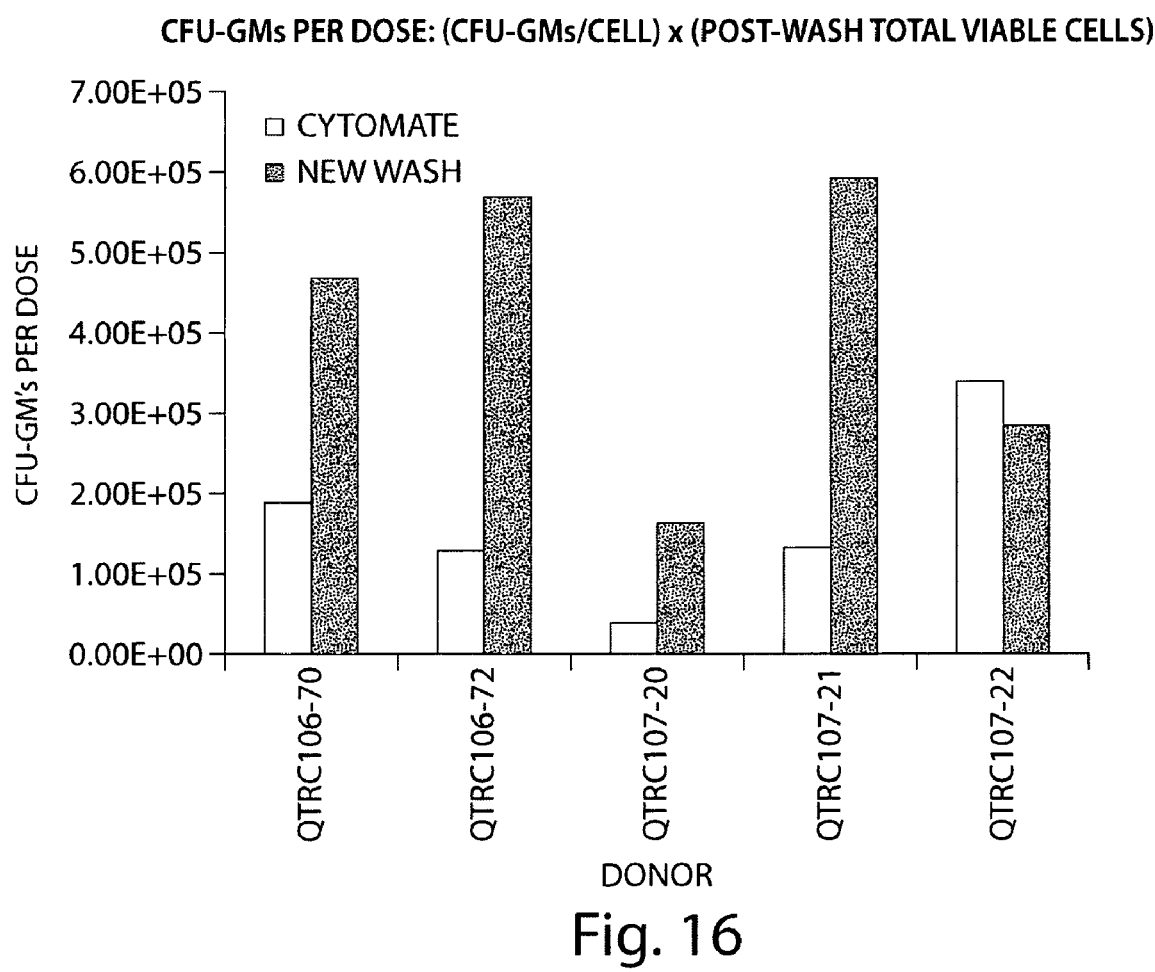
FIG. 16 is a bar graph showing CFU-GMs per dose of TRCs. Total post-wash viability cell count measured by Nucleocounter, was used to calculate CFU-GMs/dose, except where not available and trypan blue data was used (samples 106-70 and 106-72). For each pair of bars for each sample, the left bar shows results using the CYTOMATE® wash and the right bar shows results using the wash-harvest.

FIGS. 12 and 16 shows that the Wash Harvest, in almost every case, produced equal or higher frequency of CFU-GM per dose than the CYTOMATE® wash. The average of the CFU-GM frequency ratio is 1.37.

Figure 17:
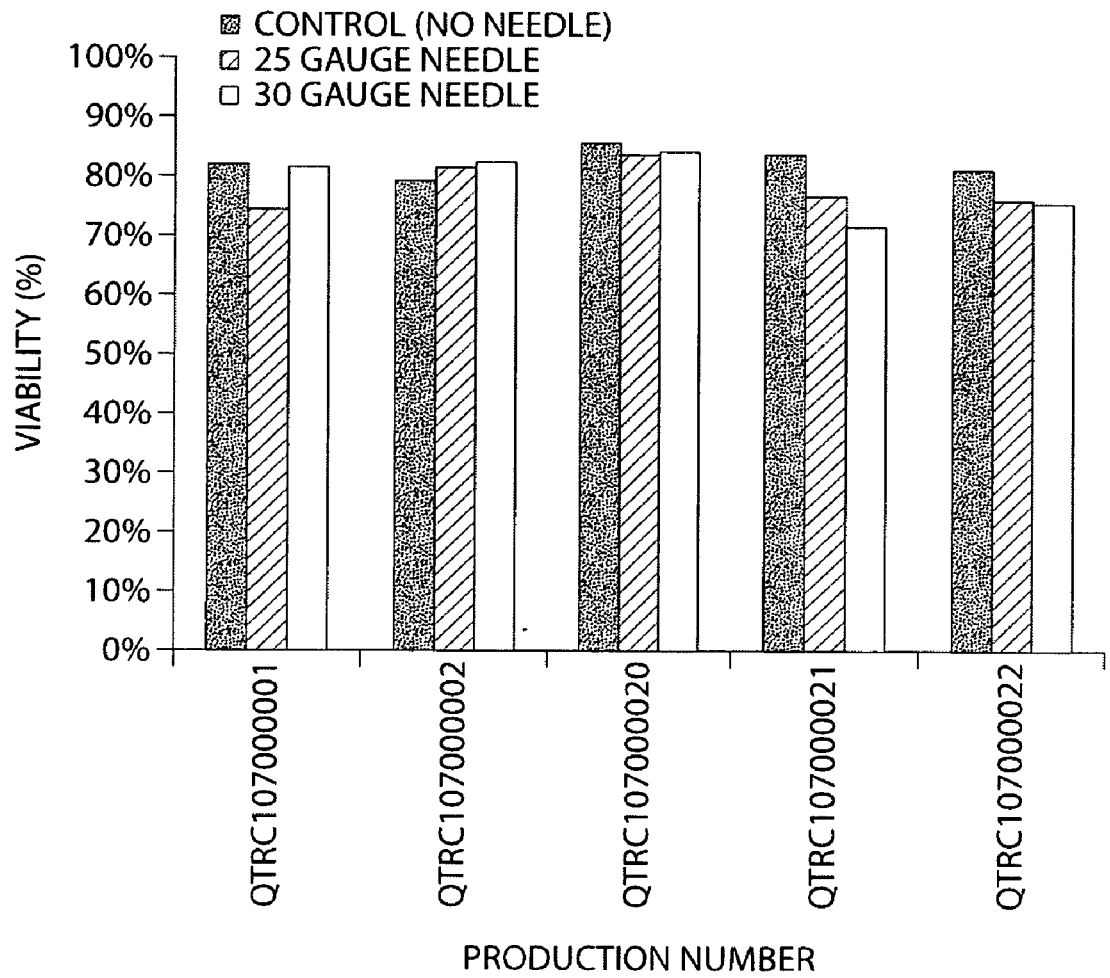
FIG. 17 is a bar graph showing the total viability of TRCs after delivery through needles measured by Nucleocounter after undergoing the wash-harvest. The bar on the left represents the control, the middle bar represents a 25 gauge needle and the right bar represents a 30 gauge needle for each experiment.

FIGS. 13 and 17 shows that the Wash Harvest, in almost every case, produced greater total numbers of CFU-GM per dose than the CYTOMATE® wash. The total CFU-GMs per dose was calculated by multiplying the frequency of CFU-GMs per cell by the post-wash total viable cell count. The average CFU-GMs per dose for the new wash process across these 6 experiments was $0.42 \times 10^6 \pm 0.19 \times 10^6$. The average CFU-GMs per dose for the CYTOMATE® wash process across these 6 experiments was $0.17 \times 10^6 \pm 0.11 \times 10^6$.

Needle Delivery

Figure 18:
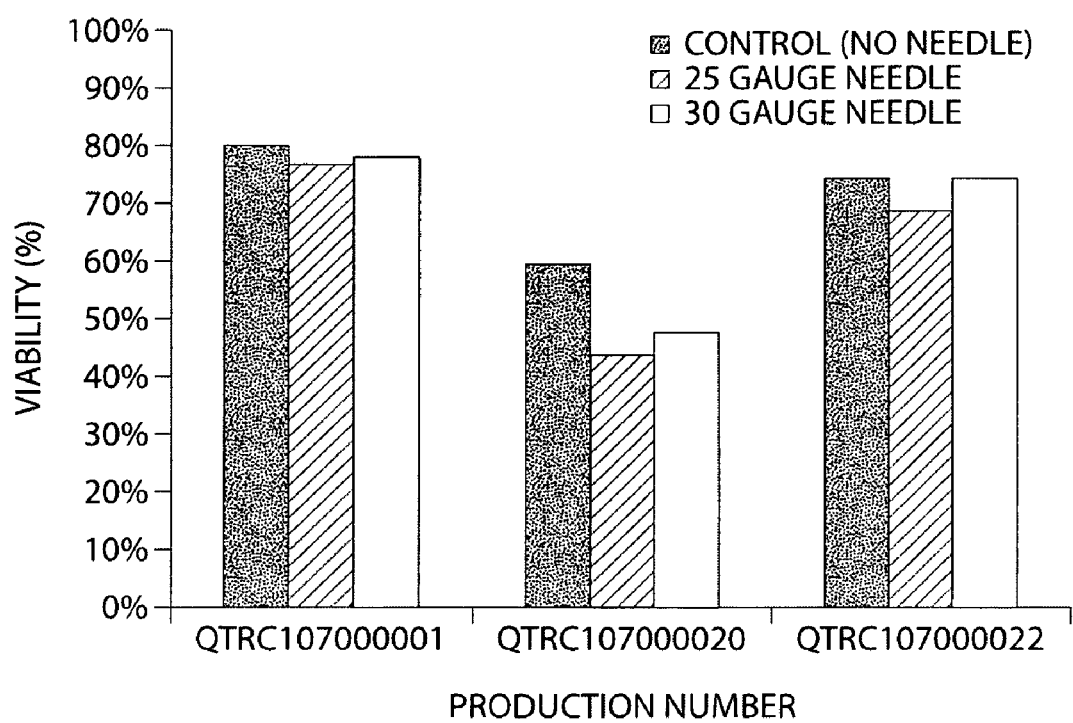
FIG. 18 is a bar graph showing the total viability of TRCs after delivery through needles measured by Nucleocounter after undergoing the CYTOMATE® wash. The bar on the left represents the control, the middle bar represents a 25 gauge needle and the right bar represents a 30 gauge needle for each experiment.

FIG. 17 shows that the cell viability of the Wash Harvest product does not show substantial change after delivery through 25 and 30 gauge needles. FIG. 18 shows similar data from CYTOMATE® washed products.

Figure 19:
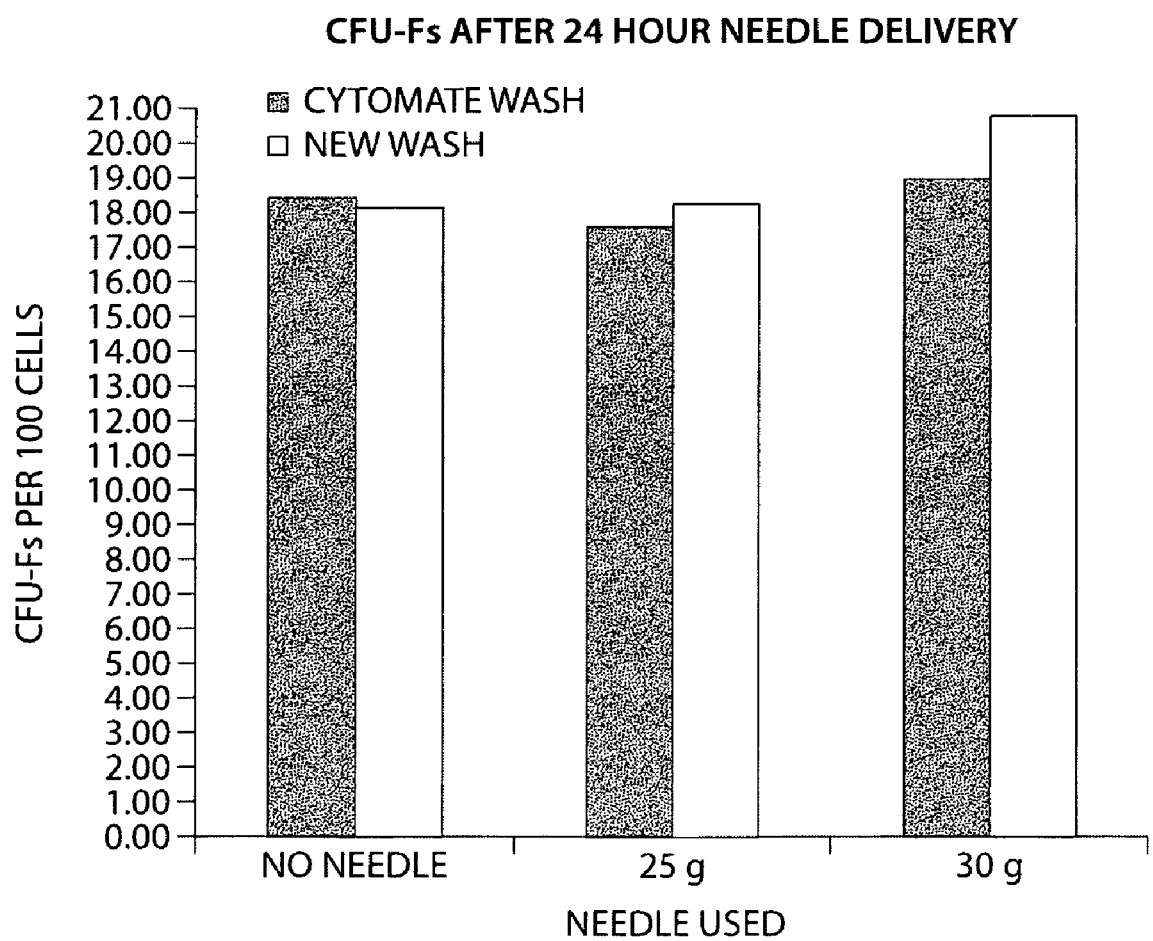
FIG. 19 is a bar graph showing CFU-Fs after 24 hour storage and needle delivery. For each pair of bars for each sample, the left bar shows results using the CYTOMATE® wash and the right bar shows results using the wash-harvest.

CFU-Fs were tested on post-needle delivery cells from experiment QTRC107000021. FIG. 19 shows the CFU-Fs per 100 cells for the three conditions. TRCs from the wash-harvest had slightly higher viability than TRCs from the CYTOMATE® wash.

This data demonstrates comparability between the processes on the ability to deliver the cells via needles at the end of processing without losing substantial cell viability following transit through small gauge needles.

Cytokine Secretion

Figure 20:
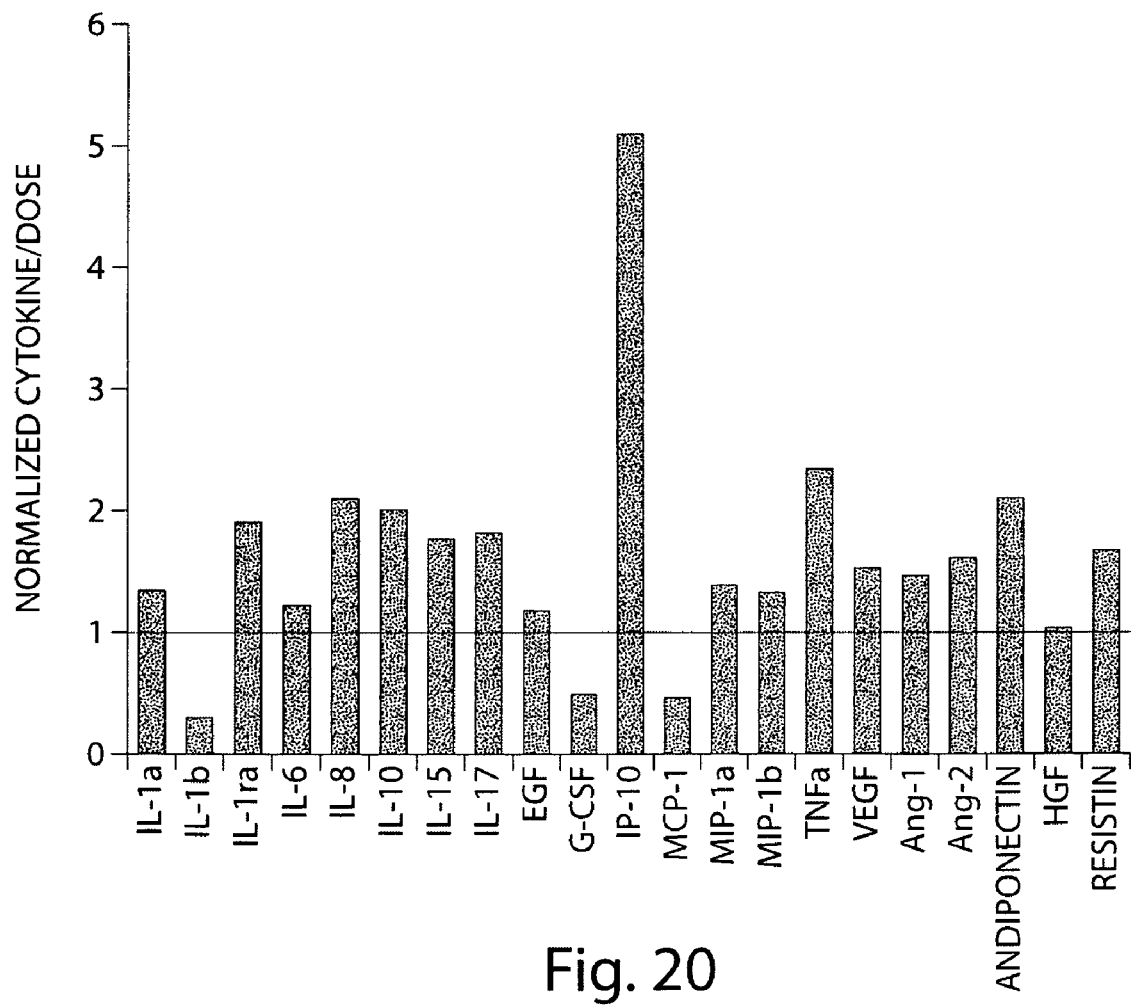
FIG. 20 is a bar graph showing the normalized Wash-harvest/CYTOMATE® wash cytokine dose for a number of cytokines on TRCs.

The cytokine secretion profile by the TRCs from the CYTOMATE® wash is comparable on a per cell basis on almost all cytokines evaluated for the wash-harvest. However, on a unit dose basis (all cells coming out of process), the total cytokine secretion per dose is generally higher from the wash-harvest (FIG. 20), thus as a concentrated composition the cell population is much more functional than the previous population.

TABLE 9

Flow cytometric analysis of TRCs and TRC-subpopulations for intra-cellular cytokine expression.

|  | TRCs |  | TRC SUBPOPULATIONS | | | | | | | | | |
|---|---|---|---|---|---|---|---|---|---|---|---|---|
|  |  |  | CD14+ Auto+ | | CD14+ Auto− | | CD66b+ | | CD90+ | | Lymphocyte | |
| LPS: | − | + | − | + | − | + | − | + | − | + | − | + |
| Control: | 0.4 | 0.3 |  |  |  |  |  |  |  |  |  |  |
| IL-6: | 11 | 15 | 6.2 | 9.2 | 0.9 | 1.2 | 0.6 | 0.7 | 1.6 | 1.1 | 1.1 | 1.3 |
| IL-10: | 6.4 | 7.9 | 2.8 | 4.5 | 0.4 | 0.6 | 0.5 | 0.4 | 0.9 | 0.6 | 0.1 | 0.1 |
| IL-12: | 0.0 | 0.0 | 0.3 | 0.2 | 0.1 | 0.1 | 0.1 | 0.1 | 0.0 | 0.0 | 0.0 | 0.0 |

Intracellular flow cytometric analysis to evaluate the frequency of cells producing IL-6, IL-10 and IL-12 was performed on TRCs produced using wash-harvest. The mean percentage of cytokine-positive cells for N=2 experiments is shown in Table 9. These observations demonstrate that a significant frequency (6-15%) of TRCs produce either IL-6 or IL-10. In contrast, intracellular IL-12 production by TRCs or TRC subpopulations was not detectable above background levels of staining observed for irrelevant control antibodies. IL-12 was not detectable above background levels regardless of stimulation with inflammatory mediators such as bacterial lipopolysaccharide (LPS). Overall, these data are highly consistent with the cytokine secretion profiles defined by Luminex and ELISA analysis of TRC supernatants (FIG. 20) which demonstrate high secretion of multiple angiogenic and immunomodulatory cytokines in the complete absence of detectable IL-12, a central pro-inflammatory mediator.

IDO Expression

Figure 24:
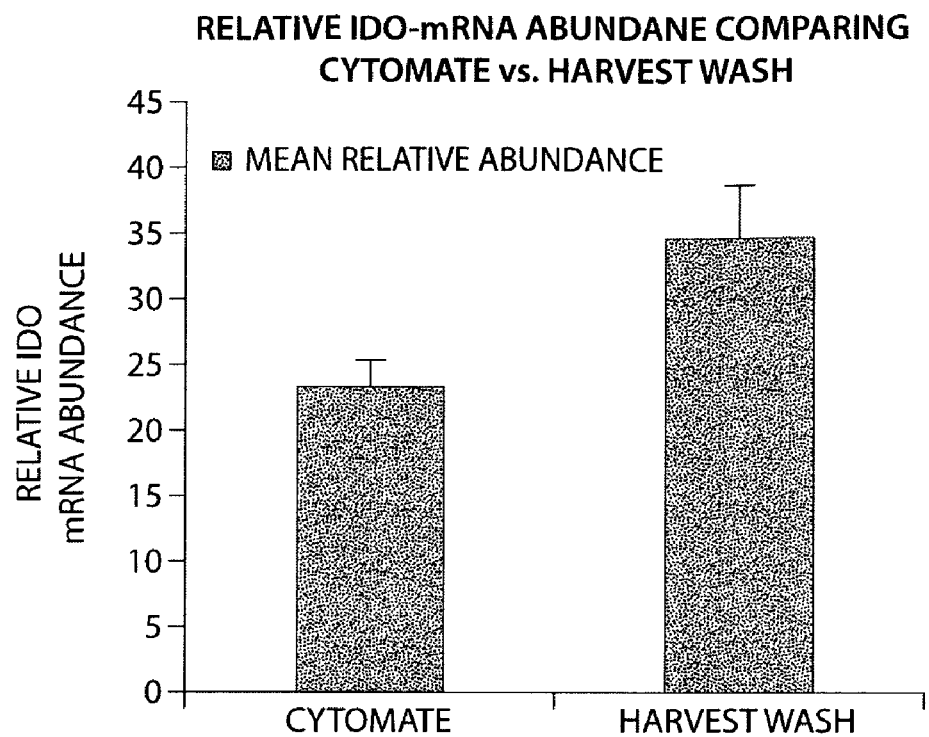
FIG. 24 is a bar graph showing the relative amount of Indoleamine 2,3-Dioxygenase (IDO) message expressed in IFNγ induced TRCs when determined by quantitative polymerase chain reaction (qPCR). The mean of triplicate samples are shown for each determination.
Figure 25:
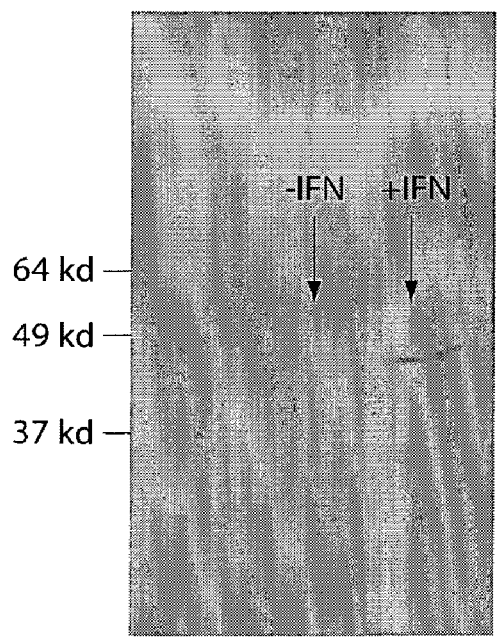
FIG. 25 is a Western blot showing the expression of Indoleamine 2,3-Dioxygenase protein in IFNγ induced TRCs.

Indoleamine 2,3 dioxygenase or IDO is an immunoregulatory enzyme. TRCs produce higher levels of IDO mRNA in response to exposure to IFN$\gamma$ (FIG. 24). TRCs also produce higher quantities of IDO protein in response to exposure to IFN$\gamma$ (FIG. 25).

PDL1 Expression

Figure 31:
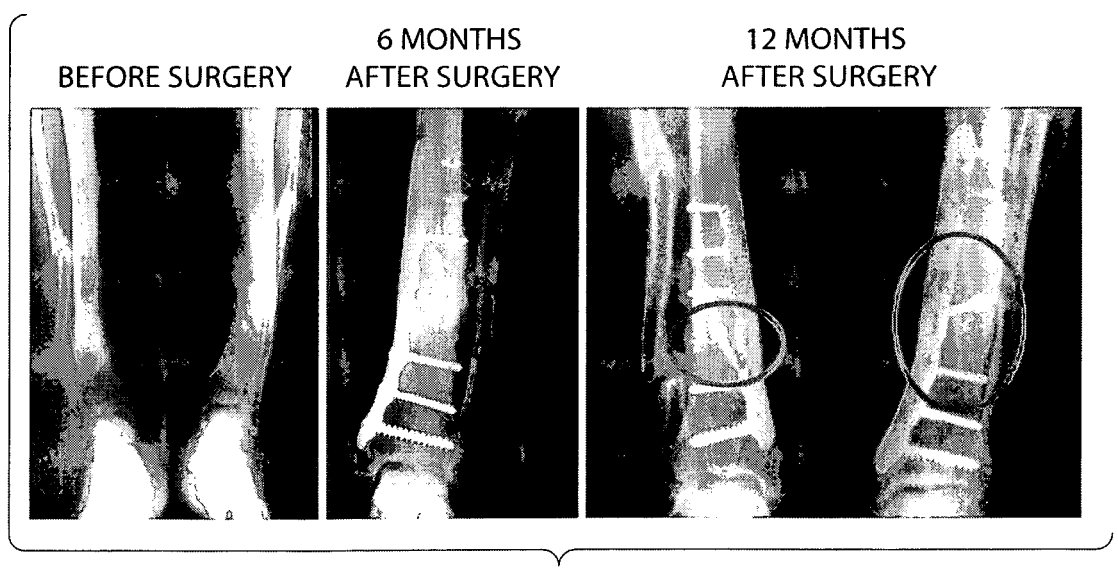
FIG. 31 shows X-rays of a patient who fell from a scaffold and was treated with TRCs for fracture of both tibias.

TRCs express high levels of PD-L1 in response to inflammatory induction (FIG. 31). TRCs were incubated without (un-induced) or with (induced) 1000 units per ml of interferon-$\gamma$ for 24 hours prior to staining with fluorochrome-conjugated isotype control, or anti-PD-L1 monoclonal antibodies for flow cytometric analysis. These observations demonstrate that TRCs up-regulate PD-L1 (>75% expression), a key inhibitory receptor implicated in down-regulation of immune and inflammatory responses.

Summary

The Wash Harvest creates a healthier cell product (p<0.05) at each stage (post-wash, post-concentration, and after 24 hours storage), as well as lower residual serum proteins (p<0.05) when compared to the CYTOMATE® wash (FIG. 11). There are no statistical differences in the percentages of CD90+, CD14+ auto+, or VegFR1+ cells, or in the F or GM colony forming capabilities. Therefore, the cell product is comparable in profile but much healthier and purer.

TABLE 10

Statistics for FIG. 11.

|  | Donor Paired Ratio New/Cytomate | Stdev | Current | stdev | new | stdev | p value < 0.05 |
|---|---|---|---|---|---|---|---|
| % Viability post-wash (n = 9) | 1.32 | 0.19 | 71.6% | 9.7% | 92.8% | 2.2% | X |
| % Viability post-concentration (n = 9) | 1.24 | 0.11 | 73.7% | 6.2% | 91.2% | 3.7% | X |
| % Viability post-24 hr storage (n = 5) | 1.32 | 0.33 | 66.8% | 14.2% | 84.5% | 3.8% | X |
| % CD90+ in final product (n = 7) | 1.07 | 0.20 | 28.8% | 13.9% | 30.1% | 13.4% |  |
| % CD14auto+ in final product (n = 6) | 1.24 | 0.10 | 26.0% | 6.6% | 31.7% | 6.4% |  |
| % VegfR1+ in final product (n = 5) | 1.24 | 0.21 | 32.2% | 10.7% | 38.5% | 8.6% |  |
| CFU-F frequency, final product (n = 3) | 0.95 | 0.25 | 7.12 | 3.60 | 7.07 | 4.17 |  |
| CFU-GM frequency, final product (n = 3) | 1.43 | 0.65 | 0.22 | 0.12 | 0.27 | 0.10 |  |
| Residual BSA, ug/ml (n = 11) | 0.61 | 0.27 | 2.65 | 0.76 | 1.51 | 0.56 | X |

When looking at the total cells in the final product (the final dose that comes out of the process), there are statistically greater numbers of total viable cells, total viable CD90+ and CD14+auto+ (two cells secreting the Immunomodulatory cytokines).

TABLE 11

Statistics for FIG. 12.

| | Donor Paired Ratio New/Cytomate | Stdev | Current (average) | stdev | New (average) | stdev | p value < 0.05 |
|---|---|---|---|---|---|---|---|
| Total viable cells post-wash (n = 9) | 1.91 | 0.72 | $95.0E^{+}6$ | $47.5E^{+}6$ | $161.1E^{+}6$ | $57.3E^{+}6$ | X |
| Total viable cells final product (n = 9) | 2.42 | 1.17 | $58.3E^{+}6$ | $32.2E^{+}6$ | $113.9E^{+}6$ | $38.6E^{+}6$ | X |
| Total viable $CD90^{+}$ in final product (n = 7) | 1.98 | 0.49 | $18.8E^{+}6$ | $8.9E^{+}6$ | $34.6E^{+}6$ | $10.5E^{+}6$ | X |
| Total viable $CD14auto^{+}$ in final product (n = 6) | 2.16 | 0.40 | $20.4E^{+}6$ | $5.4E^{+}6$ | $43.2E^{+}6$ | $11.7E^{+}6$ | X |
| Total viable $VegfR1^{+}$ in final product (n = 5) | 2.12 | 0.40 | $26.0E^{+}6$ | $13.1E^{+}6$ | $53.9E^{+}6$ | $26.4E^{+}6$ | |
| CFU-F per dose, final product (n = 3) | 1.71 | 0.68 | $5.8E^{+}6$ | $3.8E^{+}6$ | $8.9E^{+}6$ | $4.1E^{+}6$ | |
| CFU-GM per dose, final product (n = 3) | 2.64 | 1.46 | | | | | |

The Wash Harvest produced TRCs with higher viability and lower residual levels from cell culture. This allows greater numbers of TRCs to be harvested from each culture.

Further, the Wash Harvest produced TRCs with increased percentages of $CD90^{+}$, $CD14^{+}$ $Auto^{+}$ and $VEGFR1^{+}$ cells when compared to TRCs isolated using the CYTOMATE® wash. Also the wash-harvest produced TRCs that secreted more anti-inflammatory cytokines pre cell dose including IL-1ra, IL-10 and IL-6 and proteins with anti-inflammatory effects like IDO and PDL1. Further, TRCs do not express pivotal pro-inflammatory cytokines like IL-12. This shows that the TRCs isolated by the Wash Harvest method have greater tissue repair and anti-inflammatory potential because of the higher percentage of bone marrow stromal cells, endothelial cells, and monocyte/macrophage cells.

Also, the Wash Harvest technique consistently produced higher CFUs than the CYTOMATE® wash technique. This shows that the TRCs produced by the Wash Harvest technique have a greater number of progenitor and stem cells than TRCs produced by the CYTOMATE® wash technique.

Moreover, the Wash Harvest produces TRCs that do not lose substantial viability when passed through a 25 or 30 gauge needle, which may be necessary for therapeutic administration. The Wash Harvest TRCs performed about the same, if not slightly better than TRCs produced using the CYTOMATE® wash.

Example 3

Enhanced Bone Repair Potential of TRCs from Wash-Harvest Based on Increased Numbers of $CD90^{+}$ Cells The bone-forming or osteogenic potential of unexpanded bone marrow mononuclear cells (BM MNC) and TRCs was assessed using an in vitro bone differentiation assay. Briefly, TRCs isolated using the wash-harvest process were cultured for up to 3 weeks in 35 mm dishes containing either control (OS−) medium (DMEM with 10% FBS) or Osteogenic ($OS^{+}$) Medium (DMEM containing 10% FBS, 100 nM dexamethasone, 10 mM β-glycerophosphate, and 0.05 mM L-ascorbate-2-phosphate) at a concentration of 10,000 to 20,000 cells per $cm^2$. Osteogenic differentiation was assessed by cell morphology, expression of alkaline phosphatase (AP) and formation of a mineralized matrix by calcium deposition. AP activity present in the differentiated culture was quantified using the AttoPhos kit (Promega), an enzyme-catalyzed conversion of the phosphate form of AttoPhos Substrate to BBT, and measuring absorbance at 435 nm and 555 nm. Enzyme activity is expressed as Units of AP Activity. Calcium was quantified following the procedure provided in the Calcium Quantitative Kit (Pointe Scientific Inc., Canton, Mich.). Briefly, osteogenic cultures were lysed with 0.5N HCl and lysates were collected into microcentrifuge tubes. After vortexing, each sample was shaken at 500 rpm for 4 hours at 4° C. After centrifugation at 1,000×g in a microcentrifuge, supernatants were collected and assayed for the presence of calcium by measuring absorbance at 570 nm.

In separate experiments, $CD90^{+}$ cells were sorted from TRC products using the Epics Altra (Beckman Coulter) and plated for osteogenic potential as above. The average calcium deposition±SEM from three experiments for each cell population are presented.

The frequency of CD90 cells, CD15 cells, and the in vitro osteogenic potential was measured for TRCs obtained from the CYTOMATE®, the wash-harvest procedure according to the invention and mesenchymal stem cells (MSCs) from the same bone marrow donor. MSCs were cultured in DMEM medium with 10% FBS. Importantly, MSC culture includes a removal of nonadherent accessory cells near the beginning of culture, and subsequent culture and passaging of the plastic-adherent population. MSCs and TRCs were then cultured in osteogenic inductive medium for up to 3 weeks (always equivalent numbers of days within each experiment). Calcium deposition and alkaline phosphatase activity was quantitated. In this study, we evaluated the osteogenic potential of primary and first passage MSC compared to TRC.

Previous studies with CYTOMATE® TRCs have shown that 1) the osteogenic potential of TRCs is much greater than BM MNC, and 2) the osteogenic potential of TRCs resides in the CD90+ fraction of cells (Table 12).

TABLE 12

Osteogenic Potential in Unexpanded and Expanded Bone Marrow

| Cell Population | Average Calcium Deposited (μg/dish) |
|---|---|
| BM MNC | 1,094 ± 893 |
| TRC | 17,943 ± 2,864 |
| CD90+ | 7,260 ± 2,118 |
| CD90– | 13 ± 11 |

Figure 21:
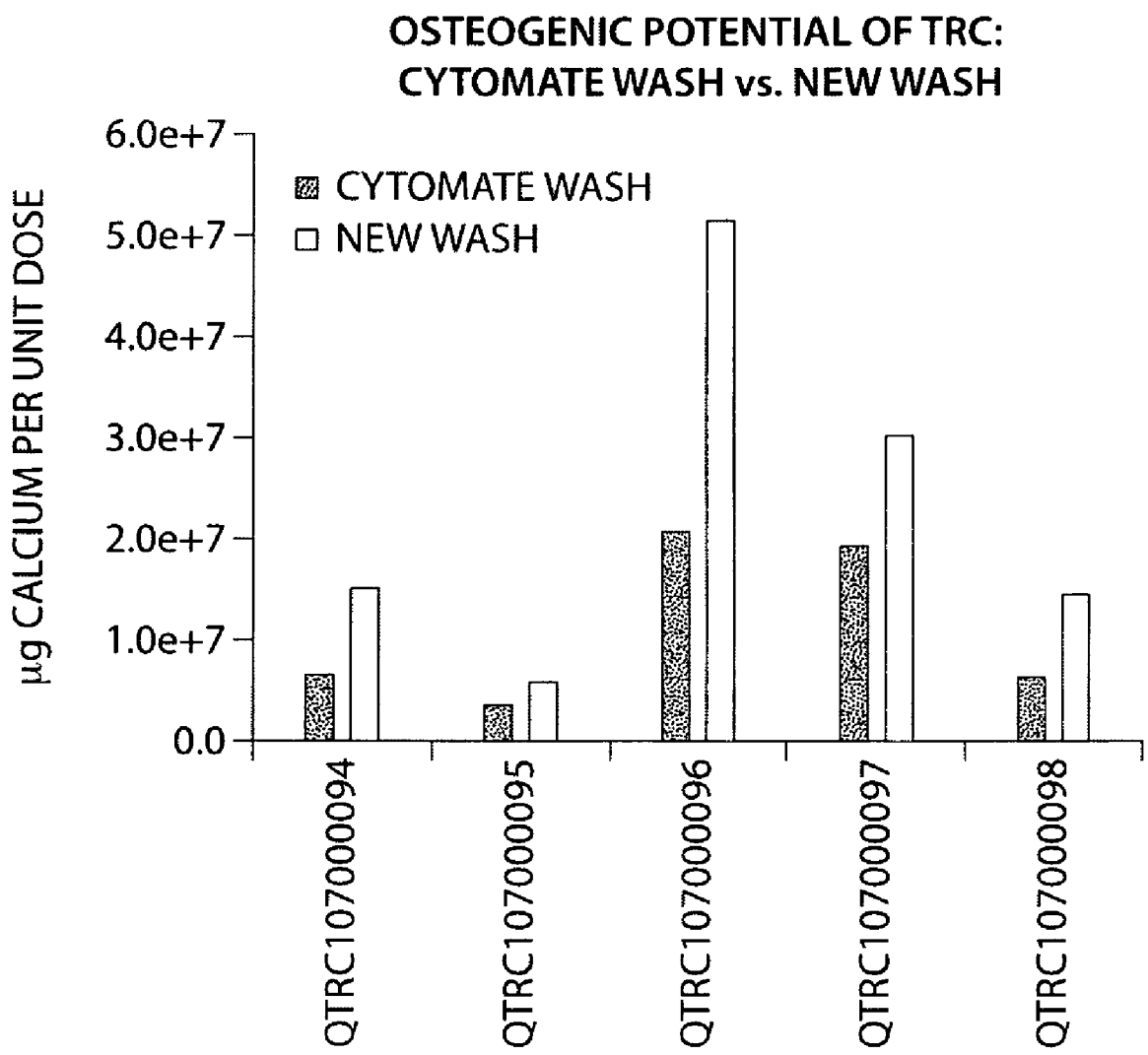
FIG. 21 is a bar graph showing the osteogenic potential of CYTOMATE® wash TRCs and Wash Harvest TRCs.

TRCs from CYTOMATE and the Wash Harvest according to the invention technique were then compared directly for osteogenic potential. By measuring calcium deposition, results show that, on average, the osteogenic potential was 2-fold higher from the Wash-Harvest TRC dose (Table 13, FIG. 21).

TABLE 13

Osteogenic Potential per unit dose is Greater from the New Wash-Harvest

| Expt # | CYTOMATE | New Wash-Harvest | Ratio New:Cytomate |
|---|---|---|---|
| QTRC107000094 | 6.57E+06 | 1.51E+07 | 2.30 |
| QTRC107000095 | 3.45E+06 | 5.62E+06 | 1.63 |
| QTRC107000096 | 2.07E+07 | 5.13E+07 | 2.48 |
| QTRC107000097 | 1.90E+07 | 3.00E+07 | 1.58 |
| QTRC107000098 | 6.15E+06 | 1.43E+07 | 2.33 |
| Average = | 1.12E+07 | 2.33E+07 | 2.06 ± 0.42 |

Figure 22A:
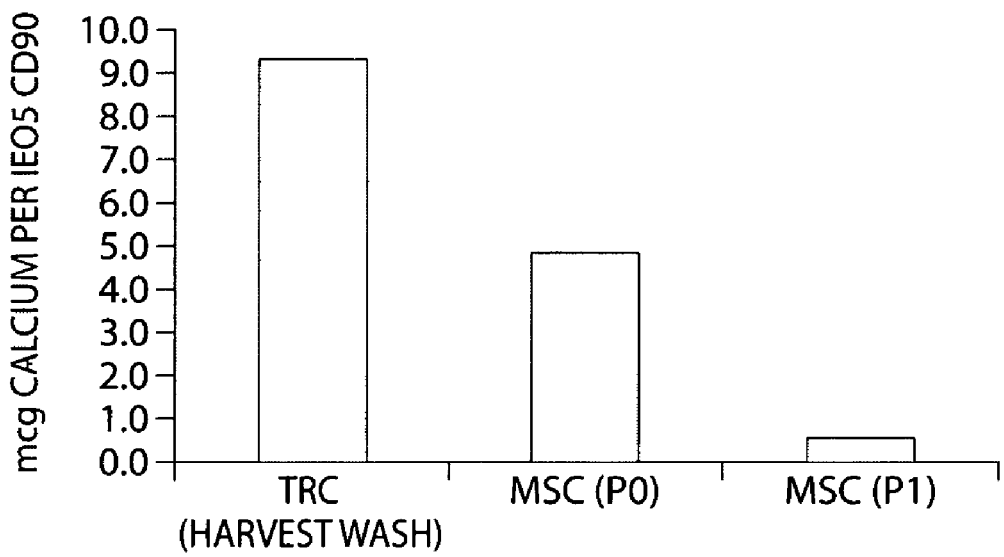
FIG. 22A is a bar graph showing the amount of calcium produced per CD90$^+$ cell plated for TRCs and mesenchymal stem cells (MSCs).
Figure 22B:
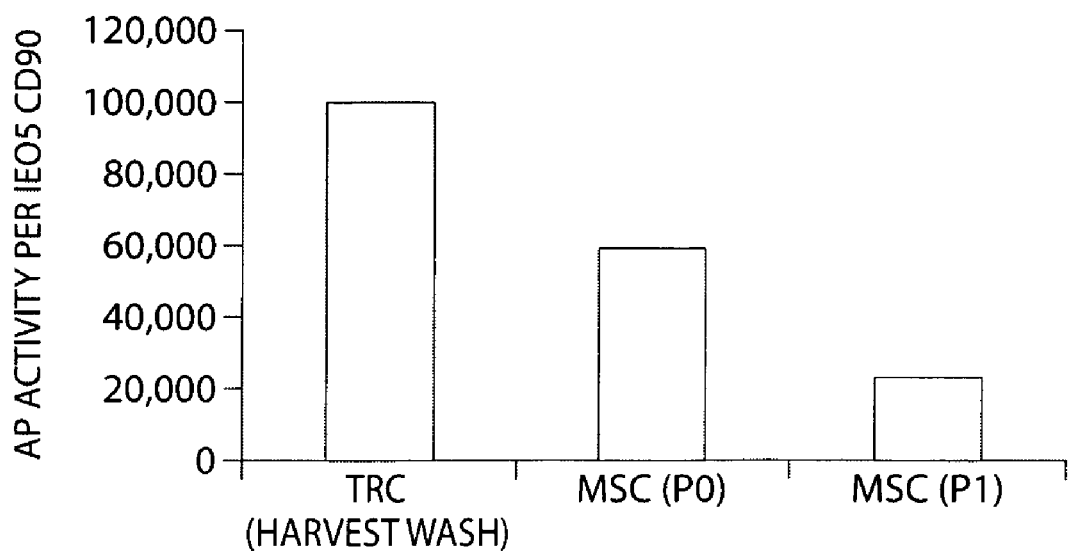
FIG. 22B is a bar graph showing the amount of alkaline phosphatase produced per CD90$^+$ cell plated for TRCs and mesenchymal stem cells (MSCs).

The osteogenic potential of TRCs was compared to the potential of another cell type, MSCs, which have been shown in the literature to possess osteogenic potential. MSCs are cultured in the absence of accessory cells and are a much more purified cell type. It was previously found that TRCs possess higher osteogenic potential than MSCs on a per CD90 cell basis. Subsequent experiments were performed to verify that the new wash-harvest TRCs exhibit the same trend. In one representative experiment shown here, the overall frequency of CD90+ cells was much lower in TRCs (16%) compared to MSCs (99%). However the frequency of CD15+ CD90+ dual positive cells (Table 9) and the osteogenic potential (Table 9; FIG. 22) are much higher in TRCs. Osteogenic potential was measured by calcium (Ca) deposition (FIG. 22A) and alkaline phosphatase (AP) activity (FIG. 22B) and was almost 2-fold higher in TRCs compared to primary MSC (P0) on a per CD90 cell basis. Additional passaging of MSCs led to even lower activity. These results are consistent with past experiments.

This data demonstrates that the TRC composition, specifically the CD90+ cells, that are produced with the wash-harvest are more potent than MSCs for osteogenic potential. TRC CD90+ cells also express the CD15 marker to a greater extent than MSC CD90+ cells.

TABLE 14

Comparison TRCs and MSCs: Phenotype and Function

| | | | | Osteogenic Potential per 1E05 CD90+ Cells | |
|---|---|---|---|---|---|
| Condition | % CD90+ | % CD15+ | % CD90+ CD15+ | $Ca^{2+}$ Deposition (mcg) | AP Activity (nmol p-nitrophenol) |
| TRC (Cytomate wash) | 19.92 | 35.29 | 14.37 | n.d. | n.d. |
| TRC (harvest wash) | 16.42 | 32.17 | 13.51 | 9.32 | 99,739 |
| MSC (P0) | 98.56 | 1.10 | 1.07 | 4.83 | 59,268 |
| MSC (P1) | 98.55 | 0.11 | 0.10 | 0.53 | 23,413 | n.d. = not determined

Direct comparison data of the wash-harvest TRCs as opposed to the CYTOMATE® wash TRCs has shown that wash-harvest TRCs products have greater osteogenic potential than. The presence of CD15 on the CD90+ cells distinguishes TRCs from other purified cell products (such as MSCs) and correlates with enhanced osteogenic potential of the CD90s.

Example 4

Clinical Trials: Bone Healing Without Inflammation with TRCs Isolated Using the CYTOMATE® Wash. Long Bone Fracture—Spain Two long bone fracture studies were conducted at centers in Spain, under Ethical Committee approvals. A Phase I clinical trial conducted at Hospital General de l'Hospitalet, Centro Méedico Teknon and Hospital de Barcelona-SCIAS enrolled five patients and treated their long bone non-union fractures. All five patients, with a total of six treated fractures, have been reported as healed by a third party independent reviewer using radiographic images (FIG. 35), or by clinical observation.

Figure 35:
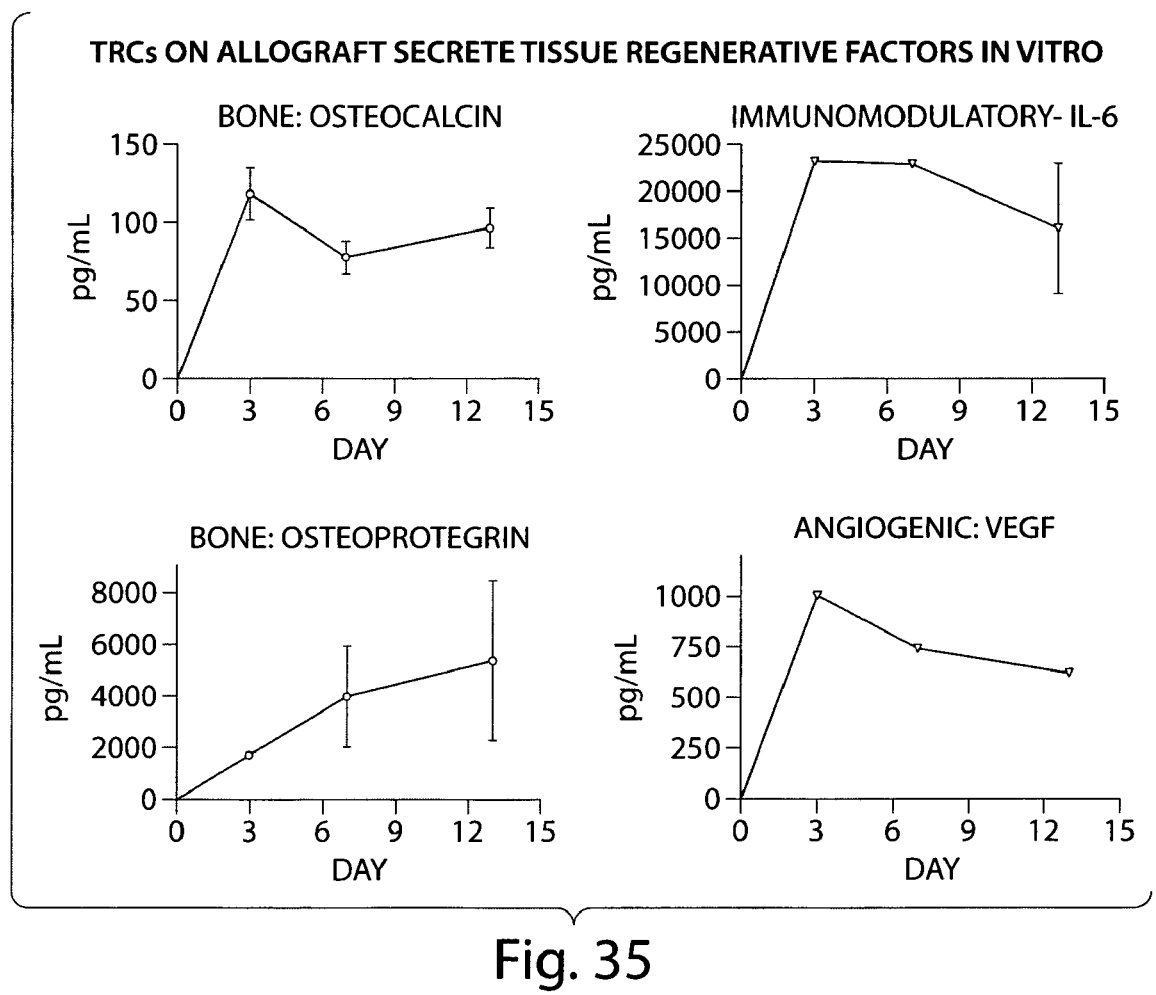
FIG. 35 displays graphs showing that TRCs maintain secretion of osteocalcin, IL-6, osteoprotegrin and VEGF throughout two weeks of culture in a TRC/DBM mixture.
Figure 36:
FIG. 36 are photographs showing the Toe of 69 year old male patient treated with TRCs. Before treatment (left) a non-healing wound was observed. 44 weeks after treatment (right) complete healing was observed. The patient suffered from numerous co-morbidities including coronary heart disease, chronic heart failure, hypertension and hyperlipidemia.
Figure 37:
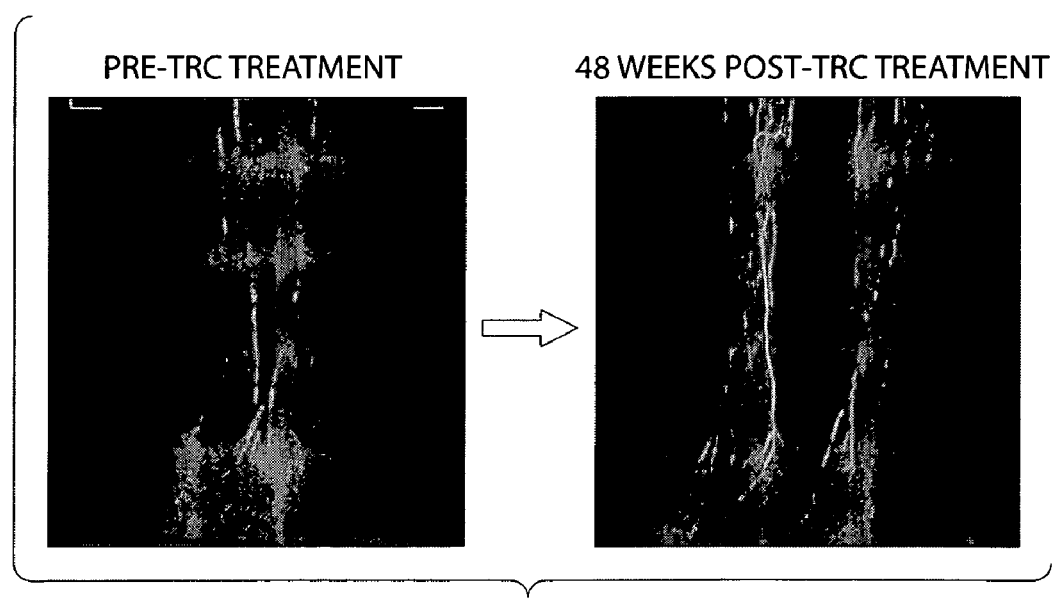
FIG. 37 are photographs showing MR-angiography of limbs of 69 year old male patient treated with TRCs. This patient received TRC injections in the right limb. Before treatment (left panel) very little collateralization is observed. 48 weeks after treatment (right panel) significantly more collaterals can be observed in the treated limb. The patient suffered from numerous co-morbidities including coronary heart disease, hypertension and hyperlipidemia.

FIG. 35 shows the clinical outcome for a patient who fell from a scaffold and broke both tibias. Healing did not occur in either bone after the first surgery. A second surgery was performed utilizing TRCs and a ceramic matrix carrier. After 6 months both the fracture lines and some matrix are visible under x-ray. At 12 months the fracture line has disappeared and the patient has healed though some residual matrix material can still be observed. At 18 months (not shown) the matrix was fully resorbed and the patient had returned to hard labor in a quarry.

No TRC-related adverse events were observed. The TRC product was used in this early study. Patients were implanted with CALCIBON® (calcium phosphate granules) matrix material mixed with TRC cells and bound with autologous plasma to enhance the handling properties. This was the first study where plasma was used to bind the matrix particles for enhanced handling.

Following the Phase I trial, an Investigational Medicinal Product Dossier (IMPD)—the required filing in the European Union (EU) for a clinical trial—was filed and permission was obtained from the Spanish Drug Agency (AEMPS) to commence a Phase II non-union fracture trial in Spain. This study has completed TRC treatment of all 10 patients.

The TRCs of the present invention was used in this study. Patients were implanted with VITOSS® (β-TCP) matrix particles mixed with TRCs and bound with plasma to facilitate handling.

Overall, 34 patients completed six-month post-treatment follow-up and 33 completed 12-month follow-up. The 33 patients followed for 12 months showed an overall healing rate of 91%, as determined by bone bridging observed with radiographic imaging or computed tomography. Final results showed healing success in 91% (21 of 23) of tibia fractures, 100% (3 of 3) of humerus fractures, and 86% (6 of 7) of femur fractures. In addition to the 91% healing rate observed after 12 months, results at six months showed that bone bridging successfully occurred in 85% (29 of 34) of patients and that signs of early healing (callus formation) were present in 97% (33 of 34) of patients. Three patients failed to complete the required follow-up visits. Though final data could not be collected from these three patients, two showed healing by 18 weeks. No cell-related adverse events were reported. The results suggest that TRCs are efficacious for the treatment of recalcitrant long bone non-union fractures and have the potential to become a powerful new tool for bone regeneration and to improve the management of severe fractures Maxillofacial Reconstruction A jaw bone (maxilla) regeneration clinical feasibility control trial in Barcelona, Spain, was completed for edentulous patients with severe bone loss who needed a sinus lift procedure so that dental implants could be placed. This feasibility trial has enrolled the targeted 5 patients for the evaluation of bone regeneration resulting from TRCs compared with a standard bone grafting procedure. Patients were implanted with BIOOSS® (bovine bone) matrix particles mixed with TRCs and bound with autologous plasma. Four months after cell therapy, the treatments that included TRCs had reduced swelling, and significant height increase of the bone in the grafted area as determined in radiographic images. Histological observations made on tissue sections adjacent to the grafted area showed changes consistent with the stimulation of bone turnover and with the induction of new connective tissue.

Reduced Inflammation in TRC-treated Patients

Initial Phase I/II clinical trials to evaluate TRCs for healing of non-union long bone fractures and jawbone reconstruction have demonstrated significant bone repair with reduced post-operative swelling, pain, redness and inflammation within 24 hours post-op. This was an unexpected observation outside of the scope of the trials and was noted in Barcelona and multiple U.S. sites in patients receiving TRC therapy.

Figure 23A:
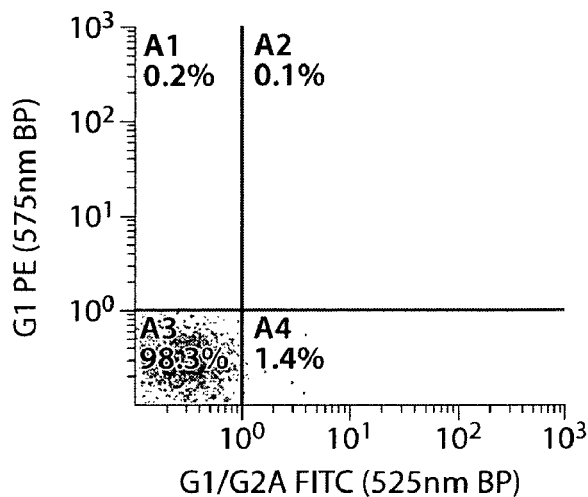
FIG. 23A shows a flow cytometric analysis of TRCs produced using the wash-harvest stained for two-color analysis using irrelevant isotype-matched control monoclonal antibodies (mAbs) (IgG1, IgG2a).

This observation has led to additional pre-clinical studies focusing on characterization of the immunomodulatory or anti-inflammatory function of the TRC mixture. Results of these studies show that TRCs express an immunomodulatory profile for optimal tissue regeneration and repair with minimal inflammation. More specifically, TRCs contain a mixture of cell types that express tissue regenerative and immunomodulatory activity including alternatively activated macrophages ($CD45^+CD14^+IL-10^+$), mesenchymal stem cells ($CD45^-CD90^+CD105^+$), regulatory T-cells ($CD45^+CD4^+CD25^+$) and other lymphocytes. In particular, the $CD3^+$ lymphocytes produce high levels of IL-10, an immunomodulatory cytokine, after triggering through the T-cell receptor-CD3 complex (FIG. 23-C). TRCs also express several potent immunoregulatory cytokines including HGF, IL-1 receptor antagonist (IL-1ra), IL-6, IL-10, TGF-β and MCP-1 at both the gene and protein level. TRCs do not express, or express at very low levels, pivotal pro-inflammatory mediators including IL-1, IFNγ, TNFα and most notably IL-12 at both the gene and protein level. TRCs are inducible for expression of a key immune regulatory enzyme designated indoleamine 2,3 dioxygenase (IDO). IDO has been implicated mechanistically in the down-regulation of both nascent and ongoing inflammatory responses. Also, TRCs demonstrate a 10-50-fold reduced stimulating activity in the allo-mixed lymphocyte reaction (MLR) when compared to professional antigen presenting cells, evaluating potential for activation of adaptive or T-cell mediated inflammatory responses.

Collectively, these observations are consistent with the hypothesis that TRCs strongly polarize or bias the host response away from the tissue-destructive inflammation and toward wound repair with more rapid healing of injured tissues.

Evidence of Early Bone Induction and Enhanced Vascularization During Bone Healing One non-union fracture patient in the US trial was non-compliant, smoking and bearing weight on the healing leg prematurely, resulting in a break in the internal fixation and the new callus at 3 months. When the plate was replaced, biopsies were taken from the mid-callus, fixed, and processed for methylmethacrylate embedding and calcified stained sections. Qualitative histology shows woven bone on the callus exterior. In the interior, lamellar bone was found on the surface of allograft matrix particles, or replacing allograft (FIG. 32). The marrow was fibrous and very well vascularized with mature arterial and venular sinusoidal-like vessels. Some small vessels appeared to cut through allograft particles. Osteoclasts, indicative of bone remodeling, were seen on bone surfaces in such regions on rare occasions. Most surfaces were lined with sheets of osteoblasts and osteoid. Polarized light microscopy showed cores of retained allograft, but a surprising amount of graft had been replaced by lamellar bone. These results provide evidence for osteoinduction, osteoconduction, and osseous integration, however the new bone in the callus was not yet mature and fully mineralized. This case exhibited very early bone induction and healing, but the callus still requires time to mineralize to regain biomechanical strength.

Figure 32A:
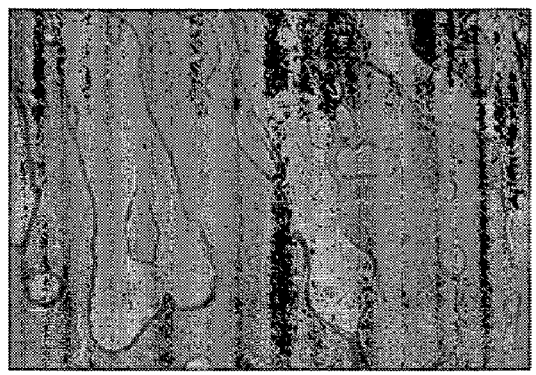
FIG. 32A shows a photomicrograph histology slide of new bone in a healing callus.
Figure 32B:
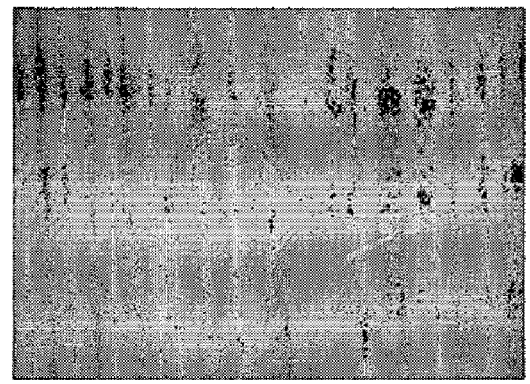
FIG. 32B shows a bright field photomicrograph histology slide of blood vessels and new bone penetrating the allograft.
Figure 32C:
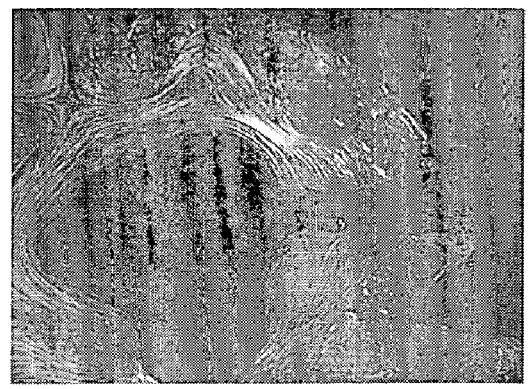
FIG. 32C shows a polarized light photomicrograph histology slide of blood vessels and new bone penetrating the allograft.

FIG. 32 shows the histology of the healing callus. FIG. 32A shows osteoblasts and new bone as osteoid cover most bone and allograft surfaces. Note the blood vessels and fibrous marrow. Bright field (FIG. 32B) and polarized (FIG. 32C) photomicrographs of same section show blood vessel penetrating into allograft DBM (parallel lamellae), and new woven bone replacing allograft on the surface and from within. Note the well-vascularized fibrous stroma and abundance of osteoblasts.

Clinical Vascular Regeneration

Based on Aastrom's observations that TRCs have the ability to form small blood vessels, and third party trials involving the use of bone marrow cells for peripheral vascular disease, a trial to evaluate the safety and efficacy of TRCs in the treatment of diabetics with open wounds and critical limb ischemia was initiated. Aastrom entered into a clinical trial agreement with the Heart & Diabetes Center located in Bad Oeynhausen, Germany, to conduct a pilot trial to evaluate the safety and potential efficacy of TRCs to improve peripheral circulation in diabetic patients with open wounds and critical limb ischemia. Patients were enrolled if they had an open wound that had not healed and showed no tendency to heal for at least 6 weeks prior to enrollment. Patient enrollment of up to 30 patients is ongoing. The investigators reported that the patients treated with TRCs healed their non-healing open wounds in 48 and 44 weeks respectively (FIG. 32) and showed improvement in collateral vessel formation (FIG. 33). The current standard of care arm of this trial showed no healing of open wounds.

Twelve months post-treatment, all patients in the interim analysis who were treated with TRCs reported no major amputations, no cell-related adverse events, and healing of all open wounds. For the two standard of care patients who only received wound care (no cells), one patient received a major amputation and one patient experienced no improvement in wound healing after 12 months.

Bone Repair

A trial to evaluate the safety and efficacy of TRCs in the treatment of osteonecrosis was initiated. Aastrom entered into a clinical trial agreement with the Orthopedic Institute, Konig-Ludwig-Haus at the University of Wurburg in Germany.located in Bad Oeynhausen, Germany, to conduct a pilot trial to evaluate the safety and potential efficacy of TRCs to repair bone in patients having osteonecrosis of the femoral head. Osteonecrosis of the femoral head involves the death of cells in the bone and marrow within the femur head and in many cases leads to total hip replacement. Four patients were treated with TRCs in the initial study. All patients tolerated the procedure well, have reported a reduction in hip pain with no signs of disease progression, as determined by MRI and X-Ray, and were back to work within 6 months after treatment. In addition, no cell-related adverse events were observed and none of these patients have required hip replacement surgery.

Mixing TRCs and Deminieralized Bone Matrix (DBM) in the Clinic

The surgeon receives a bag of TRC cell suspension, and adds this solution to a pre-measured quantity of DBM in a supplied mixing dish. The TRC/DBM mix is then bound with the patient's plasma to create a solid implant (FIG. 33A) with enhanced handling properties. Aastrom has done extensive formulation and process development to qualify this procedure, and are confident that the cells remain viable and functional during this mixing process (FIGS. 33B and 34B below).

Figure 33A:
FIG. 33A is a photograph of an implantable TRC/demineralized bone matrix (DBM) mixture that has been bound with autologous plasma.
Figure 33B:
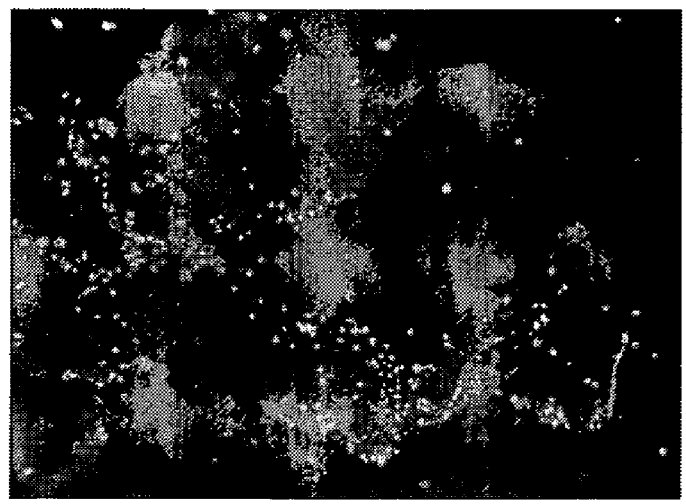
FIG. 33B is a photomicrograph of a 24 hour live/dead stain of the TRC/DBM mixture at 4×.

FIG. 33A shows an implantable TRC/DBM mixture that has been bound with autologous plasma. TRCs remain viable within the mixture as can be seen in the 24 hour live/dead stain 4× photomicrograph (FIG. 33B).

Figure 29A:
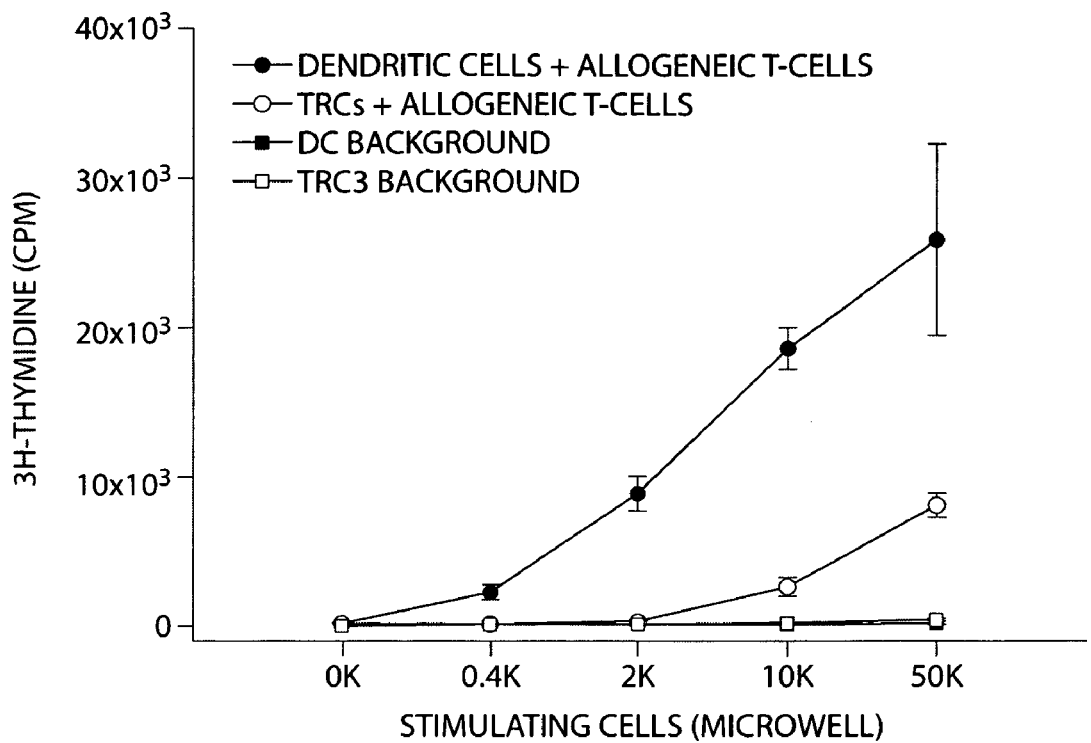
FIG. 29A is a graph showing $^3$H-thymidine incorporation in an allogeneic mixed leukocyte response (MLR) in the presence of allogeneic T-cells and dendritic cells as compared to TRCs.
Figure 29B:
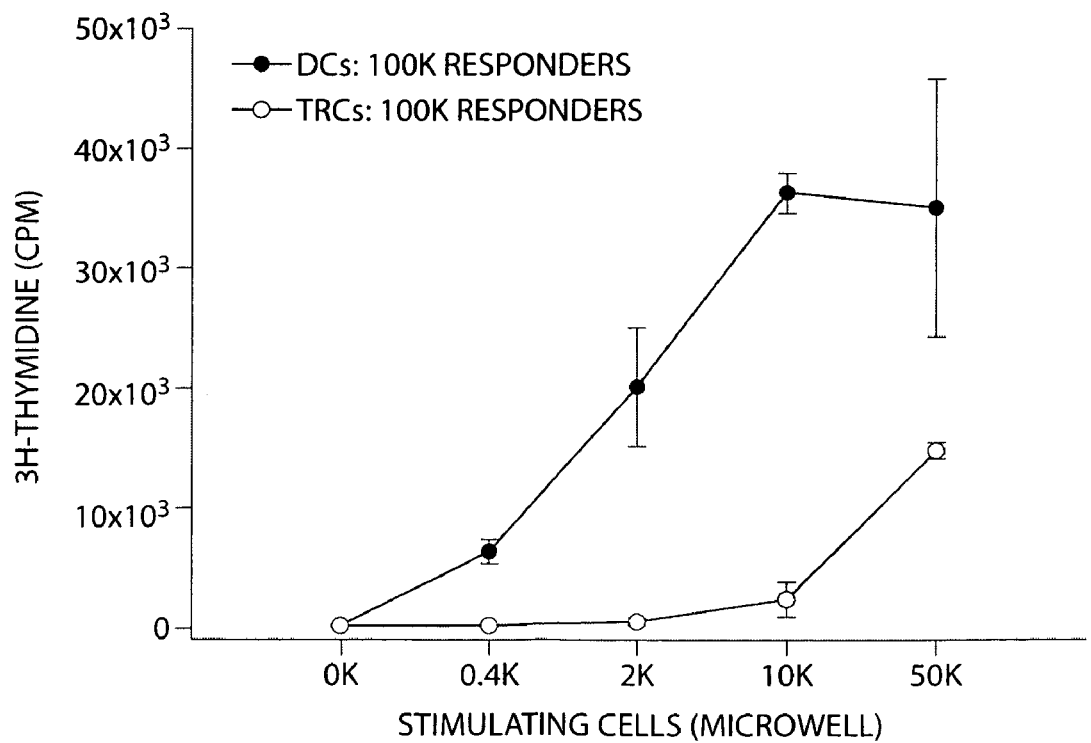
FIG. 29B is a graph showing $^3$H-thymidine incorporation in an allogeneic mixed leukocyte response (MLR) in the presence of allogeneic T-cells plus dendritic cells compared to TRCs.
Figure 34A:
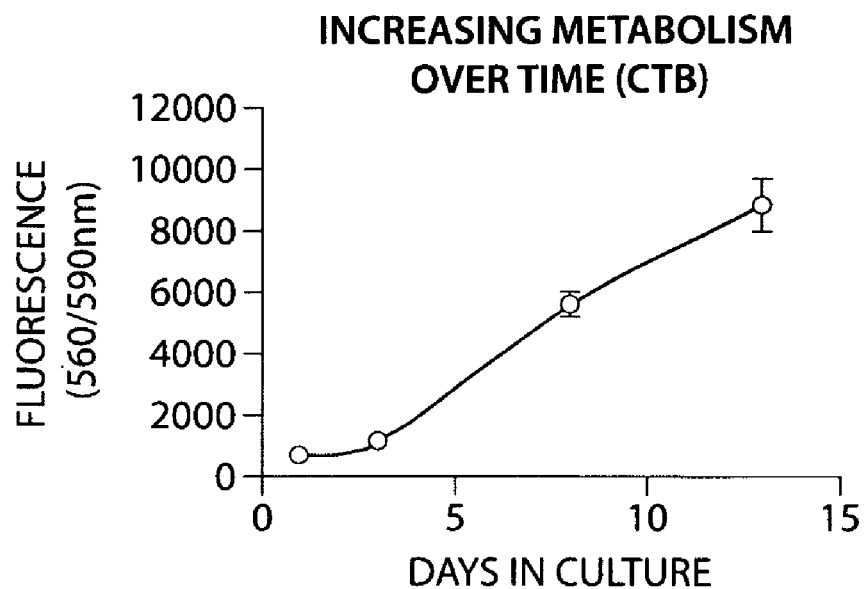
FIG. 34A is a graph showing that TRCs in the RC/DBM allograft are viable post mixing and proliferate over a two week period.
Figure 34B:
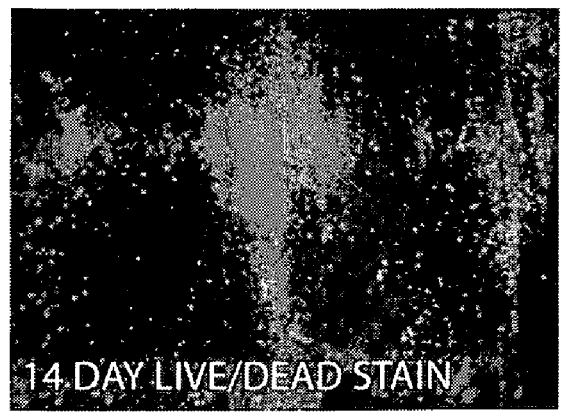
FIG. 34B is a photomicrograph of a 14 day live/dead stain of the TRC/DBM mixture at 4×.

FIG. 34A and B shows that the TRCs within the allograft/plasma mixture are viable post-mixing and capable of extensive proliferation as can be seen by the increasing metabolism over 2 weeks. Note the vast increase in cell density on the photomicrographs from day 1 (FIG. 29B above) to day 14 (FIG. 34B) (both at 4×).

FIG. 35 shows that TRCs remain functional within the DBM/plasma constructs maintain important cytokine secretion over a 2 week culture period.

Taken together, this set of clinical data with Cytomate® washed TRCs demonstrates the osteogenic, vasculo/angiogenic, and anti-inflammatory/Immunomodulatory aspects of the mixed cell product of TRCs. The new composition of matter providing cells of statistically higher viability and numbers, especially in the stem/progenitor/endothelial lineages will lead to a more functional clinical product. The new Wash Havest TRCs have been optimized for manufacturability and function, and have superior tissue repair properties previously used clinical cell products.

Example 5

TRCs Isolated Using the Wash-Harvest Method Include Regulatory T-Cells that Secrete the Anti-Inflammatory Cytokine IL-10

Figure 23B:
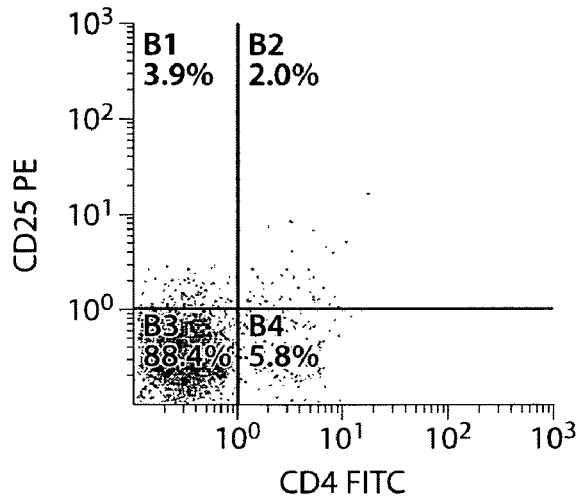
FIG. 23B shows a flow cytometric analysis of TRCs produced using the wash-harvest stained with specific fluorochrome-conjugated anti-CD25 plus anti-CD4 monoclonal antibodies (mAbs).

Tissue Repair Cells produced using the wash-harvest process were evaluated by flow cytometry. Harvested cells were stained for two-color analysis using irrelevant isotype-matched control mAbs (IgG1, IgG2a) (FIG. 23A) or specific fluorochrome-conjugated anti-CD25 plus anti-CD4 mAbs (FIG. 23B). As demonstrated in FIG. 23B (Quadrant B2) a distinct population of lymphocytes (2%) co-express the $CD4^+$ and $CD25^+$ markers, a surface phenotype associated with regulatory T-cells.

Figure 23C:
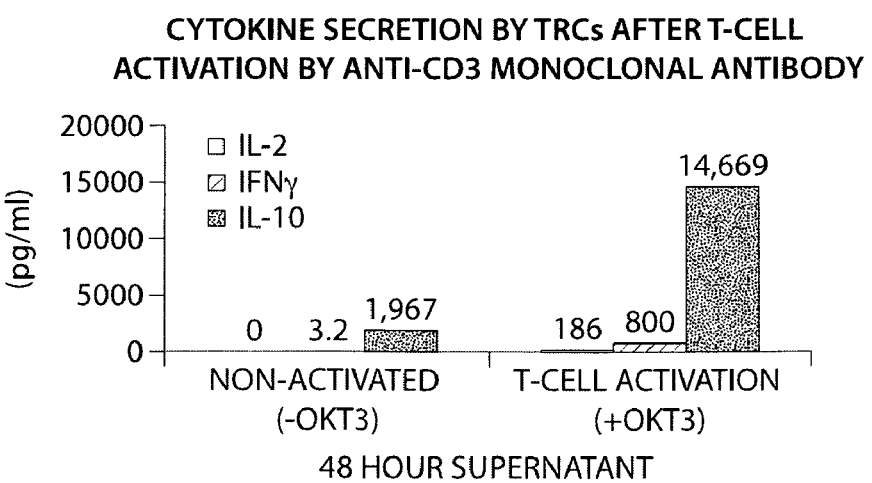
FIG. 23C is a bar graph showing the cytokine secretion profile of T-cells within the TRC mixture after specific activation with an anti-CD3 monoclonal antibody (mAb) designated OKT3. This monoclonal antibody cross-links the CD3-T-cell receptor (TCR) cell surface complex thus triggering cytokine release by T-cells. Luminex® analysis was used to evaluate IL-2, IFNγ and IL-10 release into the supernatant fluid collected 48 hours after T-cell activation using OKT3 mAb.

Similar experiments to evaluate cytokine production by T-cells within the TRC mixture are shown in FIG. 23C. TRCs were incubated alone or in the presence of plastic-immobilized anti-CD3 mAb (100 ng/ml) as a polyclonal stimulus for T-cell activation. Cytokine concentrations in 48-hour supernatant fluids were determined by Luminex multiplex analysis. Interestingly, these results demonstrate that IL-10 is the predominant cytokine (>14,669 pg/ml) produced by T-cells within the TRC mixture after activation by anti-CD3 monoclonal antibody. IL-10 is an immunomodulatory cytokine characteristically produced by regulatory T-cells and immunomodulatory macrophages.

Example 6

TRCs Release HGF, an Immunomodulatory and Angiogenic Cytokine

Hepatocyte growth factor (HGF) is a pivotal mesenchymal-derived immunomodulatory and angiogenic cytokine that mediates vascular formation, endothelialization and vascular maturation including migration and recruitment of perivascular cells such as smooth muscle cells and pericytes. HGF suppresses fibrosis after tissue injury. This cytokine drives differentiation of monocytes toward immunoregulatory and tolerogenic accessory cell function. Interestingly, HGF also has been show to reduce acute and chronic allograft rejection suggesting a potent anti-inflammatory mechanism.

Figure 26:
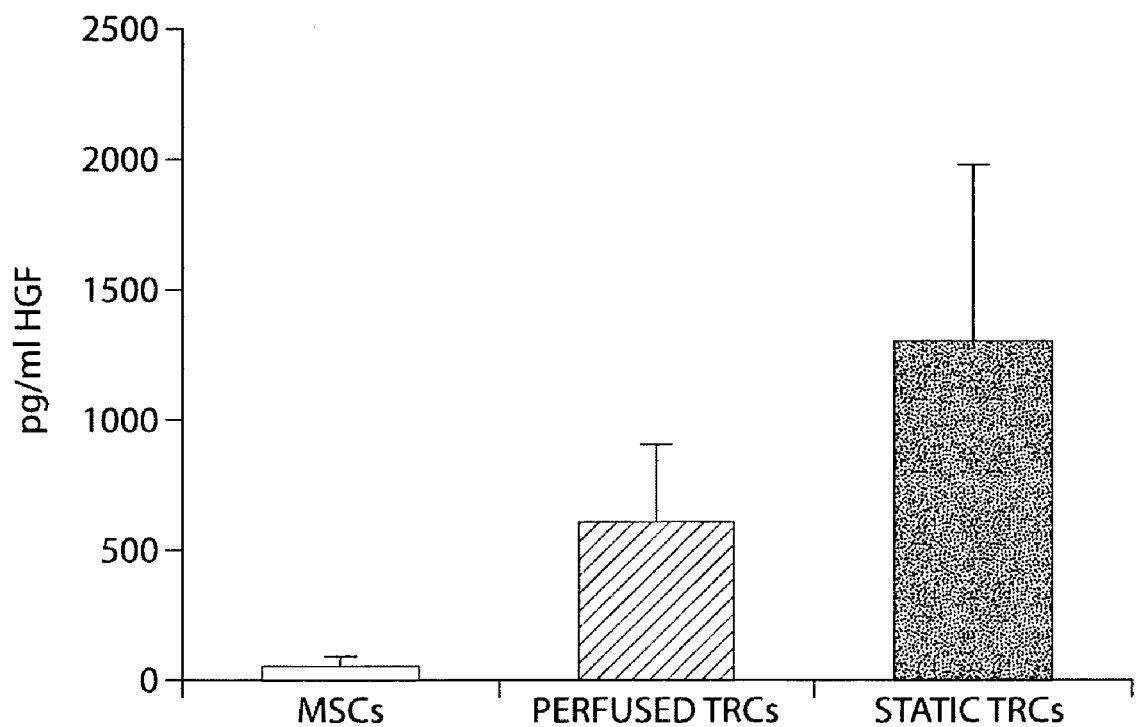
FIG. 26 is a bar graph showing HGF production by TRCs.

HGF production by TRCs was evaluated by acquisition of culture supernatant fluid from the waste port of the cell production system (see FIGS. 1-10) on day 12 of culture. These cultures were maintained under medium perfusion conditions or without medium exchange as a static culture at clinical scale. Mesenchymal stem cells (MSCs) from the same bone marrow donors were derived in parallel by repeated passage in tissue culture flasks (T-flasks) for comparison as a positive control for HGF secretion. Culture supernatant fluids from these cultures of TRCs and MSCs were evaluated for HGF by ELISA. The mean values (pg/ml) for n=6 experiments are shown in FIG. 26. These data demonstrate that TRCs consistently secrete high levels of HGF, a potent angiogenic and immunomodulatory mediator, regardless of the rate of medium perfusion when compared to conventionally derived MSCs.

Figure 27:
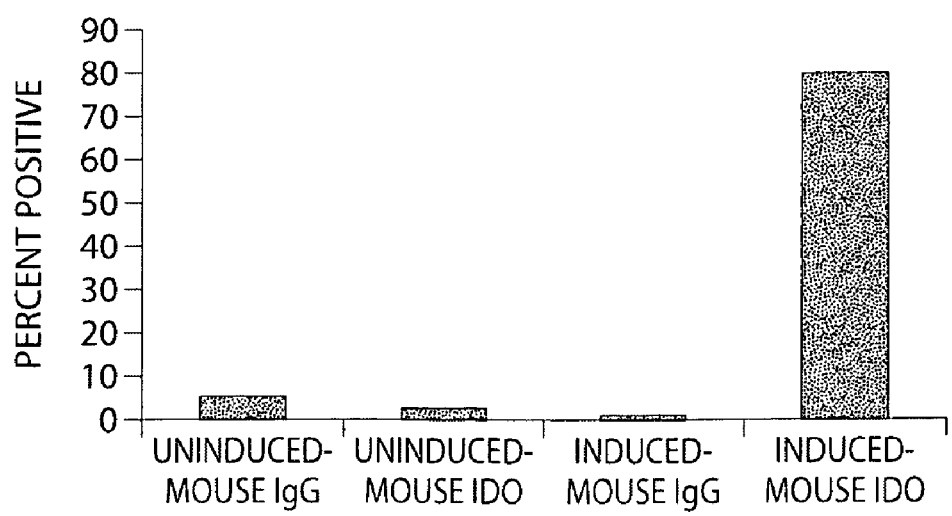
FIG. 27 is a bar graph showing the percent of IDO positive cells in IFNγ induced TRCs as determined by flow cytometry.
Figure 28:
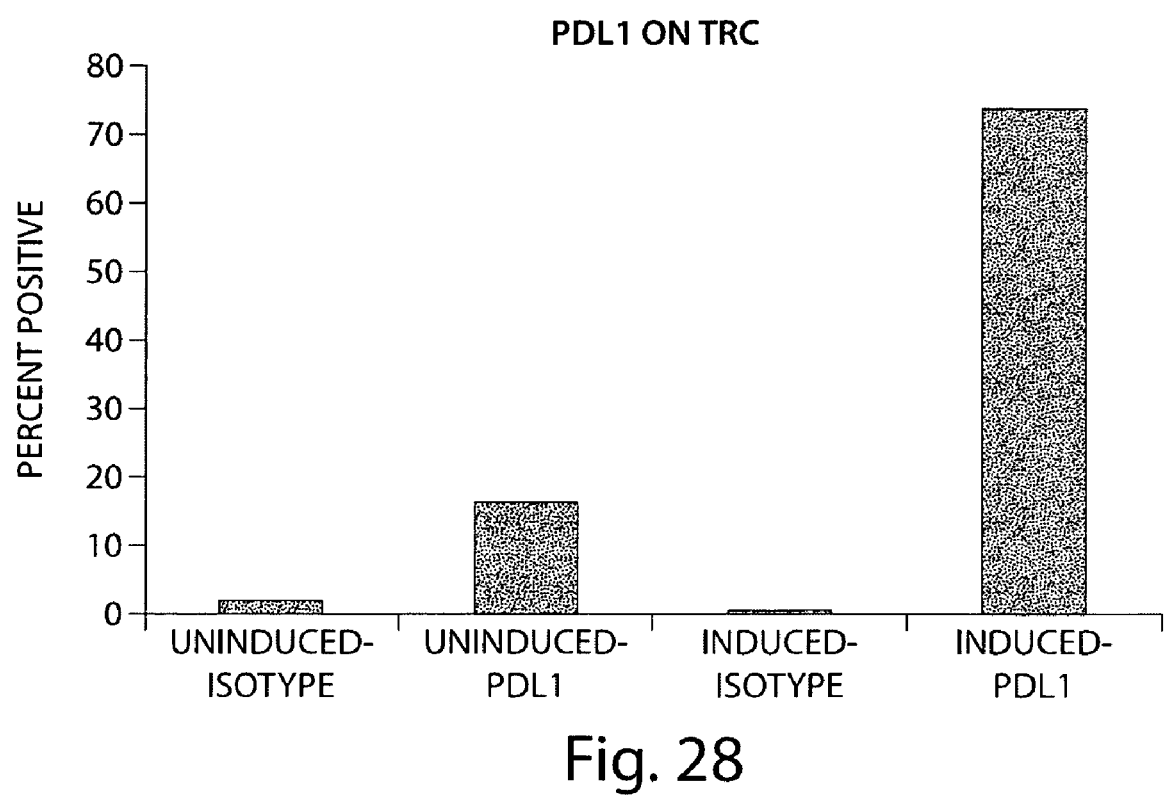
FIG. 28 is a bar graph showing the percent of PDL1 positive cells in IFNγ induced TRCs as determined by flow cytometric analysis.
Figure 30:
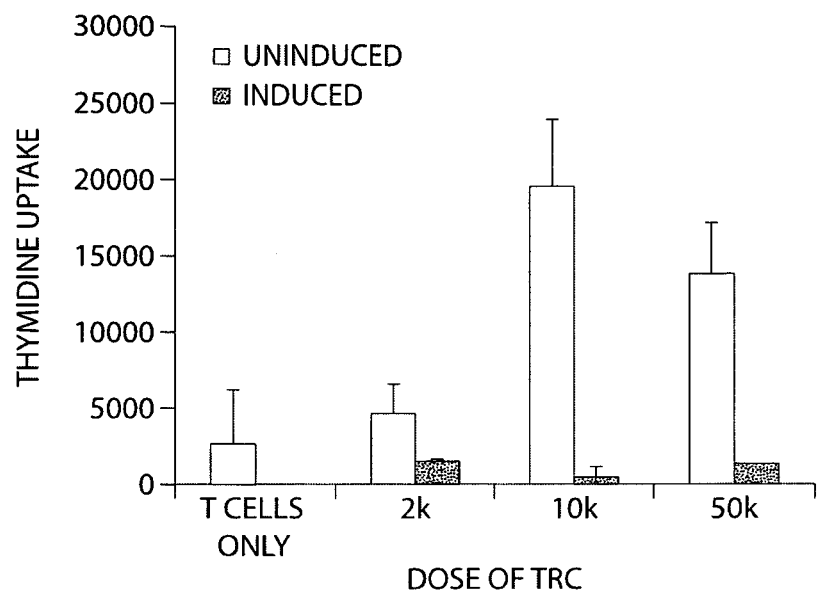
FIG. 30 is a bar graph showing $^3$H-thymidine incorporation in an allogeneic mixed leukocyte response (MLR) in the presence of allogeneic T-cells together with increasing doses of TRCs without (uninduced) or with (induced) exposure to IFNγ.

TRCs were evaluated in an allogeneic mixed leukocyte response (alloMLR) as a means to determine potential for activation of adaptive or T-cell mediated inflammatory responses (FIG. 30). Inflammatory mediators such as interferon-γ (IFN-γ) induce high expression by TRCs of immunomodulatory enzymes including IDO (FIGS. 24, 25, 27) and other immunoinhibitory ligands such as PD-L1 (FIG. 28).

Therefore, TRCs were incubated with (induced) or without (un-induced) 1000 units/ml recombinant human interferon for 24 hours prior to addition to the MLR. After exposure to IFN-γ, TRCs were irradiated (2000 Rads) and incubated in the MLR over a range of cell doses consisting of 2,000, 10,000 or 50,000 TRCs together with a fixed dose of $10^5$ responding allogeneic T-cells per microwell in triplicate cultures. T-cell proliferation was evaluated by $^3$H-Thymidine uptake as measured by counts per minute (cpm) on day 6 of culture. As shown in FIG. 30, TRCs demonstrated a striking reduction to background levels of T-cell stimulatory activity after brief exposure to inflammatory mediators such as IFN-γ. These data indicate a reduced or potentially inhibitory activity by TRCs against T-cell mediated inflammatory responses.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. An isolated cell composition for tissue repair comprising a mixed population of cells of hematopoietic, mesenchymal and endothelial lineage, wherein the cell composition is characterized as:
   a) being at least 80% viable;
   b) containing about 5-75% viable CD90$^+$ cells, with the remaining cells being CD45$^+$;
   c) containing less than 2 μg/mL of bovine serum albumin;
   d) containing less than 1 μg/mL of an enzymatically active harvest reagent; and
   e) being substantially free of mycoplasm, endotoxin, and microbial contamination.

2. The cell composition of claim 1, wherein said cells are in a pharmaceutical-grade electrolyte solution suitable for human administration.

3. The cell composition of claim 1, wherein said cells produce less than 10 pg/mL per 24 hour period per $10^5$ cells of one or more pro-inflammatory cytokines.

4. The cell composition of claim 1, wherein the cells express indoleamine-2,3-dioxygenase or PD-L1.

5. The cell composition of claim 1, wherein at least 10% of said CD90$^+$cells co-express CD15.

6. The cell composition of claim 1, wherein said CD45$^+$ cells co-express CD14, CD34 or VEGFR1.

7. The cell composition of claim 1, wherein said composition is further characterized as:
   f) being substantially free of horse serum and/or fetal bovine serum.

8. The cell composition of claim 1, wherein the total number of viable cells is 35 million to 300 million.

9. The cell composition of claim 8, wherein said composition has a volume of less than 15 milliliters.

10. The cell composition of claim 8, wherein said composition has a volume of less than 10 milliliters.

11. The cell composition of claim 8, wherein said composition has a volume of less than 7.5 milliliters.

* * * * *